(12) United States Patent
Mehta et al.

(10) Patent No.: US 8,073,008 B2
(45) Date of Patent: Dec. 6, 2011

(54) SUBNETWORK SYNCHRONIZATION AND VARIABLE TRANSMIT SYNCHRONIZATION TECHNIQUES FOR A WIRELESS MEDICAL DEVICE NETWORK

(75) Inventors: Kaezad J. Mehta, Chatsworth, CA (US); John J. Mika, III, Reseda, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1333 days.

(21) Appl. No.: 11/671,172

(22) Filed: Feb. 5, 2007

(65) Prior Publication Data
US 2007/0251835 A1 Nov. 1, 2007

Related U.S. Application Data

(63) Continuation-in-part of application No. 11/414,160, filed on Apr. 28, 2006.

(51) Int. Cl.
*H04J 3/22* (2006.01)
*H04J 3/06* (2006.01)
(52) U.S. Cl. .......................................... 370/468; 370/503
(58) Field of Classification Search .......... 370/464–468, 370/498, 503
See application file for complete search history.

(56) References Cited

U.S. PATENT DOCUMENTS

| | | | |
|---|---|---|---|
| 3,631,847 A | 1/1972 | Hobbs, II | |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |

(Continued)

FOREIGN PATENT DOCUMENTS

DE 4329229 3/1995

(Continued)

OTHER PUBLICATIONS

PCT Search Report (PCT/US02/03299), Oct. 31, 2002, Medtronic Minimed, Inc.

(Continued)

*Primary Examiner* — Aung S Moe
*Assistant Examiner* — Kerri Rose
(74) *Attorney, Agent, or Firm* — Ingrassia Fisher & Lorenz, P.C.

(57) ABSTRACT

A fluid infusion system as described herein includes a number of local "body network" devices, such as an infusion pump, a handheld monitor or controller, a physiological sensor, and a bedside or hospital monitor. The body network devices can be configured to support communication of status data, physiological information, alerts, control signals, and other information between one another. In addition, the body network devices can be configured to support networked communication of status data, physiological information, alerts, control signals, and other information between the body network devices and "external" devices, systems, or communication networks. The networked medical devices are configured to support a variety of wireless data communication protocols for efficient communication of data within the medical device network. In addition, the wireless medical devices may be configured to support a number of dynamically adjustable wireless data communication modes to react to current operating conditions, application-specific data content, or other criteria.

9 Claims, 27 Drawing Sheets

U.S. PATENT DOCUMENTS

| | | | |
|---|---|---|---|
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,319,363 A | 6/1994 | Welch et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,497,772 A | 3/1996 | Schulman et al. | |
| 5,543,326 A | 8/1996 | Heller et al. | |
| 5,558,638 A | 9/1996 | Evers et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,689,229 A | 11/1997 | Chaco et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,898,690 A | 4/1999 | Masashi | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,154,675 A | 11/2000 | Juran et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |
| 6,285,897 B1 | 9/2001 | Kilcoyne et al. | |
| 6,287,252 B1 | 9/2001 | Lugo | |
| 6,329,161 B1 | 12/2001 | Heller et al. | |
| 6,385,593 B2 | 5/2002 | Linberg | |
| 6,408,330 B1 | 6/2002 | DeLaHuerga | |
| 6,418,346 B1 | 7/2002 | Nelson et al. | |
| 6,424,847 B1 | 7/2002 | Mastrototaro et al. | |
| 6,438,603 B1 | 8/2002 | Ogus | |
| 6,442,432 B2 | 8/2002 | Lee | |
| 6,443,890 B1 | 9/2002 | Schulze et al. | |
| 6,472,122 B1 | 10/2002 | Schulman et al. | |
| 6,484,046 B1 | 11/2002 | Say et al. | |
| 6,484,221 B1 | 11/2002 | Lorinser et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,560,741 B1 | 5/2003 | Gerety et al. | |
| 6,564,104 B2 | 5/2003 | Nelson et al. | |
| 6,565,509 B1 | 5/2003 | Plante et al. | |
| 6,579,690 B1 | 6/2003 | Bonnecaze et al. | |
| 6,580,700 B1 | 6/2003 | Pinard et al. | |

| | | |
|---|---|---|
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Funderburk et al. |
| 6,763,269 B2 | 7/2004 | Cox |
| 6,809,653 B1 | 10/2004 | Mann et al. |
| 6,847,892 B2 | 1/2005 | Zhou et al. |
| 6,864,803 B2 | 3/2005 | Tang et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,002,944 B2 | 2/2006 | Kats et al. |
| 7,151,765 B2 | 12/2006 | Zhang et al. |
| 7,153,263 B2 | 12/2006 | Carter et al. |
| 7,153,289 B2 | 12/2006 | Vasko |
| 7,164,661 B2 * | 1/2007 | Kelly ............................. 370/323 |
| 7,184,449 B2 * | 2/2007 | Spalink ......................... 370/508 |
| 7,242,907 B2 * | 7/2007 | Garrison et al. ............. 455/63.1 |
| 7,294,105 B1 | 11/2007 | Islam |
| 7,327,705 B2 | 2/2008 | Fletcher et al. |
| 7,333,514 B2 | 2/2008 | Anehem et al. |
| 7,396,330 B2 | 7/2008 | Banet et al. |
| 7,647,237 B2 | 1/2010 | Malave et al. |
| 7,821,964 B2 * | 10/2010 | Ayyagari et al. .............. 370/254 |
| 2001/0044731 A1 | 11/2001 | Coffman et al. |
| 2002/0013518 A1 | 1/2002 | West et al. |
| 2002/0055857 A1 | 5/2002 | Mault |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2002/0181478 A1 * | 12/2002 | Shizume ....................... 370/401 |
| 2003/0025599 A1 | 2/2003 | Monroe |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0133422 A1 | 7/2003 | Bims |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0125776 A1 | 7/2004 | Haugli et al. |
| 2004/0167465 A1 | 8/2004 | Mihai et al. |
| 2004/0203362 A1 | 10/2004 | Pattabiraman et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0071190 A1 | 3/2005 | Herger et al. |
| 2005/0080403 A1 | 4/2005 | Takahashi |
| 2005/0119535 A1 | 6/2005 | Yanagihara et al. |
| 2005/0143671 A1 | 6/2005 | Hastings et al. |
| 2005/0154271 A1 | 7/2005 | Rasdal et al. |
| 2005/0192557 A1 | 9/2005 | Brauker et al. |
| 2005/0251552 A1 | 11/2005 | Champel et al. |
| 2006/0026296 A1 | 2/2006 | Nagaraj |
| 2006/0045134 A1 * | 3/2006 | Eldon et al. .................. 370/503 |
| 2006/0074462 A1 | 4/2006 | Verhoef |
| 2006/0229694 A1 | 10/2006 | Schulman et al. |
| 2006/0238333 A1 | 10/2006 | Welch et al. |
| 2006/0241392 A1 | 10/2006 | Feinstein et al. |
| 2006/0253300 A1 | 11/2006 | Somberg et al. |
| 2006/0293571 A1 | 12/2006 | Bao et al. |
| 2007/0030847 A1 | 2/2007 | Frei et al. |
| 2007/0088521 A1 | 4/2007 | Shmueli et al. |
| 2007/0118397 A1 | 5/2007 | Williams et al. |
| 2007/0135866 A1 | 6/2007 | Baker et al. |
| 2007/0223404 A1 | 9/2007 | Khan et al. |
| 2007/0233521 A1 | 10/2007 | Wehba et al. |
| 2007/0255111 A1 | 11/2007 | Baldus et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkami K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed• Technologies.

(Intensive Diabetes Management, 1995). Insulin Infusion Pump Therapy. pp. 66-78.

Disetronic My Choice™ D-TRON™ Insulin Pump Reference Manual. (no date).

Disetronic H-TRON® plus Quick Start Manual. (no date).

Disetronic My Choice H-TRONplus Insulin Pump Reference Manual. (no date).

Disetronic H-TRON® plus Reference Manual. (no date).

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.

(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(MiniMed Technologies, 1994). MiniMed 506 Insulin Pump User's Guide.

(MiniMed Technologies, 1994). MiniMed™ Dosage Calculator Initial Meal Bolus Guidelines / MiniMed™ Dosage Calculator Initial Basal Rate Guidelines Percentage Method. 4 pages.

(MiniMed, 1996). MiniMed™ 507 Insulin Pump User's Guide.

(MiniMed, 1997). MiniMed™ 507 Insulin Pump User's Guide.

(MiniMed, 1998). MiniMed 507C Insulin Pump User's Guide.

(MiniMed International, 1998). MiniMed 507C Insulin Pump for those who appreciate the difference.

(MiniMed Inc., 1999). MiniMed 508 Flipchart Guide to Insulin Pump Therapy.

(MiniMed Inc., 1999). Insulin Pump Comparison / Pump Therapy Will Change Your Life.

(MiniMed, 2000). MiniMed® 508 Users Guide.

(MiniMed Inc., 2000). MiniMed® Now [I] Can Meal Bolus Calculator/ MiniMed® Now [I] Can Correction Bolus Calculator.

(MiniMed Inc., 2000). Now [I] Can MiniMed Pump Therapy.

(MiniMed Inc., 2000). Now [I] Can MiniMed Diabetes Management.

(Medtronic MiniMed, 2002). The 508 insulin Pump a Tradition of Excellence.

(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.

Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.

Geise, Robert J., et al., "Electropolymerized 1,3-cliaminobenzene for the construction of a 1,1'-dimethylferrocene mediated glucose biosensor," Analytica Chimica Acta, 281, 1993, pp. 467-473.

Gernet, S., et al., "A Planar Glucose Enzyme Electrode," Sensors and Actuators, 17, 1989, pp. 537-540.

Gernet, S., et al., "Fabrication and Characterization of a Planar Electromechanical Cell and its Application as a Glucose Sensor," Sensors and Actuators, 18, 1989, pp. 59-70.

Gorton, L., et al., "Amperometric Biosensors Based on an Apparent Direct Electron Transfer Between Electrodes and Immobilized Peroxlases," Analyst, Aug. 1991, vol. 117, pp. 1235-1241.

Gorton, L., et al., "Amperometric Glucose Sensors Based on Immobilized Glucose-Oxidizing Enymes and Chemically Modified Electrodes," Analytica Chimica Acta, 249, 1991, pp. 43-54.

Gough, D. A., et al., "Two-Dimensional Enzyme Electrode Sensor for Glucose," Analytical Chemistry, vol. 57, No. 5, 1985, pp. 2351-2357.

Gregg, Brian A., et al., "Cross-Linked Redox Gels Containing Glucose Oxidase for Amperometric Biosensor Applications," Analytical Chemistry, 62, pp. 258-263.

Gregg, Brian A., et al., "Redox Polymer Films Containing Enzymes. 1. A Redox-Conducting Epoxy Cement Synthesis, Characterization, and Electrocatalytic Oxidation of Hydroquinone," The Journal of Physical Chemistry, vol. 95, No. 15, 1991, pp. 5970-5975.

Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Acc. Chem. Res., vol. 23, No. 5, May 1990, pp. 128-134.

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714.

Jönsson, G., et al., "An Electromechanical Sensor for Hydrogen Peroxide Based on Peroxidase Adsorbed on a Spectrographic Graphite Electrode," Electroanalysis, 1989, pp. 465-468.

Kanapieniene, J. J., et al., "Miniature Glucose Biosensor with Extended Linearity," Sensors and Actuators, B. 10, 1992, pp. 37-40.

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 525-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.

Poitout, V., et al., "A glucose monitoring system for on line estimation oh man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series Vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognition of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer caniers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

PCT Search Report for PCT/US07/067563, Nov. 18, 2008, Medtronic Minimed, Inc.

PCT Written Opinion for PCT/US07/067563, Nov. 18, 2008, Medtronic Minimed, Inc.

PCT Search Report for PCT/US07/067561, Dec. 20, 2007, Medtronic Minimed, Inc.

PCT Written Opinion for PCT/US07/067561, Dec. 20, 2007, Medtronic Minimed, Inc.

* cited by examiner

SUBNETWORK SYNCHRONIZATION AND VARIABLE TRANSMIT SYNCHRONIZATION TECHNIQUES FOR A WIRELESS MEDICAL DEVICE NETWORK

CROSS-REFERENCE TO RELATED APPLICATION(S)

This application is a continuation-in-part of U.S. patent application Ser. No. 11/414,160, filed Apr. 28, 2006.

TECHNICAL FIELD

Embodiments of the present invention relate generally to medical devices and medical device networks, such as infusion systems that deliver fluids into a patient's body. More particularly, embodiments of the present invention relate to systems and techniques related to wireless data communication protocols, and wireless data communication features suitable for use in a medical device network environment.

BACKGROUND

Portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

The prior art includes a number of insulin pump systems that are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's BG level in real time.

Insulin pumps and continuous glucose monitoring devices may also be configured to communicate with remote control devices, monitoring or display devices, BG meters, and other devices associated with such an infusion system. Individual devices within conventional infusion systems may be configured to support a limited amount of wired or wireless data communication to support the operation of the infusion system. For example, a continuous glucose monitoring sensor may include a wireless radio frequency ("RF") transmitter that communicates with a BG monitor device within the infusion system. As another example, the infusion system may include a handheld remote control that communicates with the infusion pump device using wireless techniques. Conventional infusion systems, however, operate in a somewhat isolated and local manner in that the routing of control signals, monitoring signals, patient status information, physiologic data, alerts, activation instructions, programming signals, and other data communication generally occurs within the limited short range and local operating environment of the infusion system itself. Moreover, many conventional infusion systems do not take advantage of certain protocols that facilitate efficient and effective wireless data communication between devices arranged in a network.

BRIEF SUMMARY

An embodiment of a medical device system as described here includes wireless devices that are configured to support a number of RF data communication protocols, techniques, and technologies that enable efficient routing of system data over wireless links. The medical device system includes a plurality of devices arranged in a wireless network topology (and/or in a wired network topology). Moreover, a wireless medical device in the "local" or "body" area network can be suitably configured to communicate with one or more external network devices, such as networked computers, cellular telephones, personal digital assistants, hospital monitoring equipment, pager devices, or the like. Wireless network communications within the medical device network may convey device status information, physiologic patient data, alerts, and/or alarms. Moreover, wireless network communications within the medical device network may convey data that originates from external devices outside the local system environment, such as device programming instructions, device actuation instructions, calibration parameters, alert/alarm enable or disable signals, and/or other control parameters to the local system devices.

A number of desirable RF operating features may be carried out by an embodiment of a medical device system having: a plurality of medical devices forming a medical device network; a first subnetwork in the medical device network, the first subnetwork including a first subset of the plurality of medical devices configured to communicate data between each other using a first synchronized timing scheme; and a second subnetwork in the medical device network, the second subnetwork including a second subset of the plurality of medical devices configured to communicate data between each other using a second synchronized timing scheme. The medical device network is configured to adjust the first synchronized timing scheme and the second synchronized timing scheme to enable concurrent operation of the first subnetwork and the second subnetwork.

A number of desirable RF operating features may also be carried out by an embodiment of a communication method for a medical device network having a first device and a second device configured to communicate data between each other using a synchronized data communication protocol. The method involves: the first device dynamically determining when a next data packet will be transmitted to the second device over a wireless data communication channel; and the first device transmitting a variable time indicator to the second device. The variable time indicator indicates when the next data packet will be transmitted over the wireless data communication channel, and the variable time indicator prompts the second device to configure itself to receive the next data packet as designated by the variable time indicator.

An embodiment of a medical device system may also employ wireless data communication signals. Desirable RF operating features may be achieved using an embodiment of a wireless data communication signal having data fields transmitted over a wireless data communication channel between a first device in a medical device system and a second device in the medical device system. The wireless data communication signal includes a data packet including data representing a variable time indicator that indicates when a next data packet will be transmitted over the wireless data communication channel.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
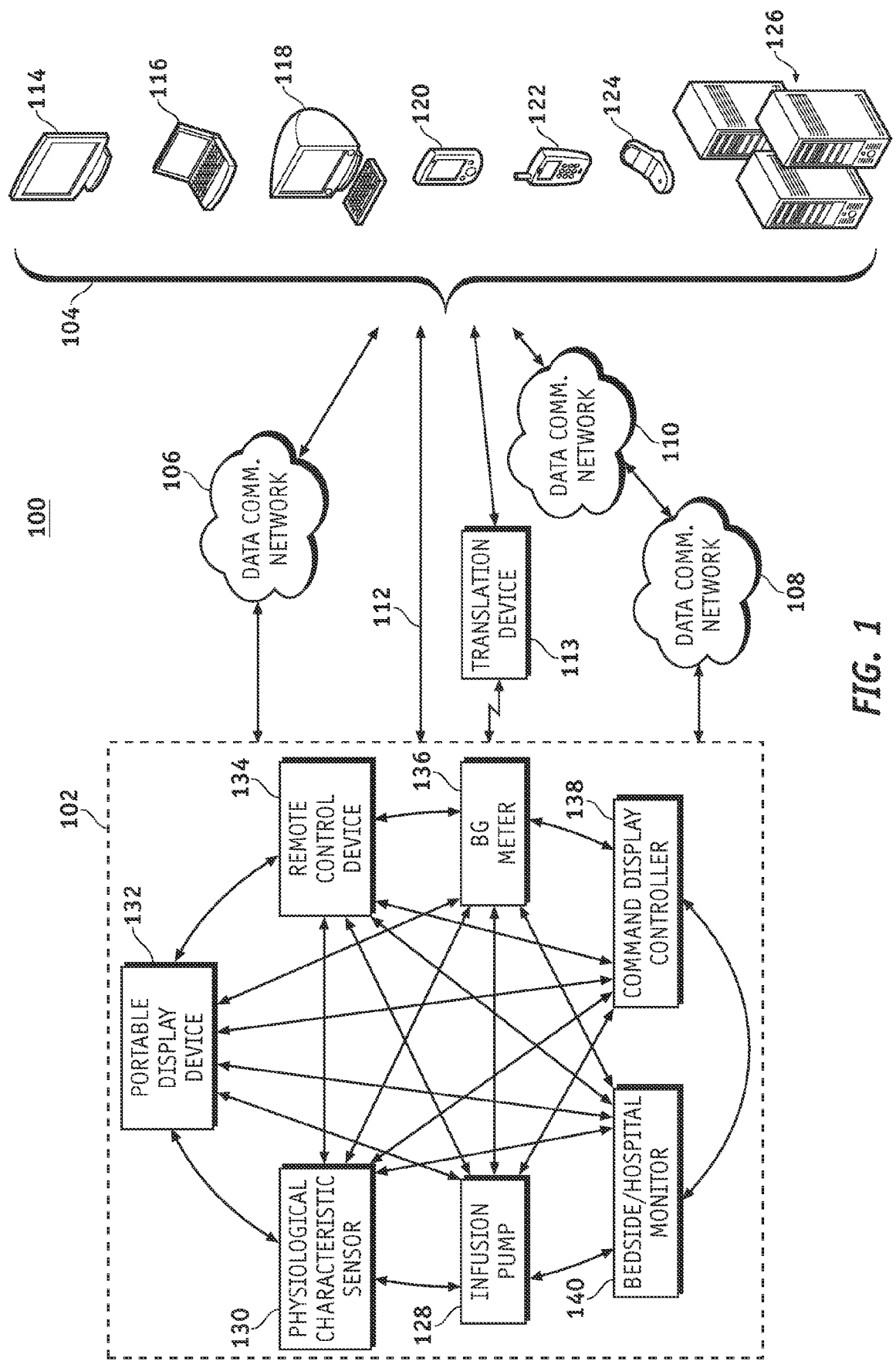
FIG. 1 is a schematic representation of a network-based infusion system configured in accordance with an example embodiment of the invention.

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Embodiments of the invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present invention may be practiced in conjunction with any number of data transmission protocols and that the system described herein is merely one example embodiment of the invention.

For the sake of brevity, conventional techniques related to infusion system operation, insulin pump and/or infusion set operation, blood glucose sensing and monitoring, signal processing, data transmission, signaling, network control, and other functional aspects of the systems (and the individual operating components of the systems) may not be described in detail here. Examples of infusion sets that may be used as a delivery device are described in, but not limited to, U.S. Pat. Nos. 4,723,947; 4,755,173; 5,176,662; 5,584,813; 6,056,718; 6,461,329; 6,475,195; 6,520,938; 6,585,695; 6,591,876; and 6,607,509, which are herein incorporated by reference. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices maybe be of the type described in, but not limited to, U.S. Pat. Nos. 6,484,045; 6,809,653; 6,892,085; and 6,895,263, which are herein incorporated by reference. Furthermore, the connecting lines shown in the various figures contained here are intended to represent example functional relationships and/or physical couplings between the various elements. It should be noted that many alternative or additional functional relationships or physical connections may be present in an embodiment.

The following description may refer to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although each of the schematic block diagrams depicts one example arrangement of elements, additional intervening elements, devices, features, or components may be present in an embodiment of a device, system, or network.

FIG. 1 is a schematic representation of a network-based medical device system 100 configured in accordance with an example embodiment of the invention. In this example, system 100 is an insulin infusion system that controls the infusion of insulin into the body of a user. Aspects of the invention, however, may also be utilized in the context of other medical device systems. Briefly, system 100 includes a local infusion system 102 having one or more local devices that communicate (unidirectional or bidirectional) with one or more network devices 104. As used here, network devices 104 are "external" to local infusion system 102 because they need not utilize the local data communication protocols and techniques employed within local infusion system 102, and because they need not be in close physical proximity to the local devices within local infusion system 102. The manner in which a given local device within local infusion system 102 communicates with a given network device 104 may vary depending upon the particular configuration of system 100, the characteristics of that local device, and the characteristics of that network device 104. For example, network communications may be routed using one data communication network 106, using a plurality of data communication networks 108/110, using a direct wireless or wired connection 112, or the like. In one example embodiment, data from wireless devices within local infusion system 102 (and/or data from wireless devices associated with different local infusion systems) may be collected by a wireless telemetry router device that serves as an interface to one or more network devices 104. One example wireless telemetry router device is described in more detail below in connection with FIG. 21.

Data communicated within local infusion system 102 and/or between devices within local infusion system 102 and network devices 104 may include or represent, without limitation: physiologic patient data, device status information, time and date information, alarm/alert status, and other information related to the operation, status, or condition of the patient, related to any of the devices within local infusion system 102, or related to local infusion system 102 itself. For example, such data may include or represent bolus information, basal information, or sensor information. Such data may also include or represent information entered by the patient, a caregiver, or another person having access to a local device or a network device 104, such as, without limitation: reminders; event markers (for meals, exercise, or the like); alarms; notifications; or the like.

In one embodiment, devices within local infusion system 102 can communicate with network devices 104 via a suitably configured translation device, system, or application 113. For example, such a translation device 113 may be configured to communicate with devices within local infusion system 102 using a suitable RF data communication protocol (which may be published or proprietary), while coupling to one or more network devices 104 via a standardized data communication interface such as USB, IEEE 1394, or the like. The translation device 113 may also be provisioned with flash memory capability such that patients or caregivers can save data received from a device in a portable storage device and physically transport the storage device to any compatible computing device, e.g., a personal computer at a doctor's office. One example translation device is described in more detail below in connection with FIGS. 18-20.

As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media. Communication hardware utilized by a data communication network may include a mechanically detachable unit such as an SDIO, a USB ready wireless module, or the like. For example, data communication network 106 may include, without limitation: a computer network such as a local area network or a wide area network; a pager network; a cellular telecommunication network; a cordless telephone system; an 802.11 network (WiFi); an 802.16 network (WiMAX); the Internet; IEEE P1901 BPL (Broadband over Power Lines); a hospital data communication network (WMTS or other); a home network, such as a home control network, a home security system, or a home alarm system; the public switched telephone network; a satellite communication network; or the like. In embodiments, network communications between local infusion system 102 and network devices 104 may be routed by two or more different types of data communication networks using known or proprietary network interfacing techniques.

The flexible nature of network-based infusion system 100 is illustrated in FIG. 1, which depicts local infusion system 102 in communication with a variety of external and remote network devices 104. In an embodiment, local devices within local infusion system 102 may be suitably configured to support the transmission of network communications to: a stationary monitor device 114, such as a bedside monitor or a piece of hospital monitoring equipment; a portable computer 116, such as a laptop PC, a palmtop PC, or a tablet PC; a stationary computer 118, such as a desktop PC; a personal digital assistant 120, which may also be a portable email device; a smart phone 122, which may also be a portable email device; a wireless phone 124, such as a cellular phone or a cordless phone; one or more additional computing devices or databases 126; or the like. As described in more detail below, these local devices need not communicate only via a local network interface and such devices may communicate using other means. The above list of possible network devices 104 is not exhaustive, and an implementation of system 100 can be designed to accommodate network communication with other network systems, equipment, computing devices, components, and elements that are external to local infusion system 102.

In one embodiment, local infusion system 102 is realized as an insulin infusion system that is locally controlled and monitored by the patient. In this example, local infusion system 102 includes at least an infusion pump 128. Local infusion system 102 may also include any of the following components, without limitation: a physiological characteristic sensor 130, such as a continuous glucose sensor (which may include a wireless transmitter); a portable display device 132; a remote control device 134; a BG meter 136 or other physiological characteristic meter; a command display controller 138 for infusion pump 128; and a monitor device 140, which may be realized as a bedside monitor or a hospital monitor. Each of these local devices is described in more detail below.

As depicted in FIG. 1, these local devices may be configured to transmit and receive local communications within local infusion system 102, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Local infusion system 102 may be flexibly configured such that any given local device can communicate with any other local device, and a communication link or path between two local devices may be unidirectional or bidirectional. FIG. 1 depicts an example embodiment where each communication link or path is bidirectional (represented by double headed arrows).

Infusion pump 128 is configured to deliver fluid, such as insulin, into the body of a user via, for example, an infusion set. In accordance with one example embodiment, infusion pump 128 serves as a central hub, and most of the processing logic and intelligence for local infusion system resides at infusion pump 128. In some embodiments, the local medical device system need not include infusion pump 128, for example, monitoring systems utilized in conjunction with traditional insulin injection therapy. Moreover, infusion pump 128 need not include a display. In an embodiment that lacks a display, portable display device 132, remote control device 134, command display controller 138, or any other device within local infusion system 102 may serve as a remote display for infusion pump 128. Other options for a remote display include, but are not limited to, any of the network devices 104 described above, e.g., wireless phone 124, monitor device 114, portable computer 116, or personal digital assistant 120.

In practice, operation of infusion pump 128 may be remotely controlled by command display controller 138 (which may be realized as a handheld monitor/controller for infusion pump 128), by remote control device 134, and/or by or monitor 140. In one example embodiment, BG meter 136 may include the functionality of a controller device such that both components share a single housing. One such BG meter is described in U.S. patent application Ser. No. 11/204,667, titled "Controller Device for an Infusion Pump," the content of which is incorporated by reference herein. Control of infusion pump 128 may also be possible via a suitably configured user interface located at infusion pump 128 itself.

Local infusion system 102 may also include physiologic characteristic sensor 130, which is suitably configured to measure a physiologic characteristic of the patient. In addition, sensor 130 may include processing and control logic that enables it to control the operation of infusion pump 128. Such control may be responsive to measurements obtained by sensor 130. In the example system described here, sensor 130 is a continuous BG sensor that measures the BG level of the patient in real time. Sensor 130 may include a wireless transmitter that facilitates transmission of physiologic data of the user to other devices within local infusion system 102. Alternatively, sensor 130 may be directly wired to a monitor/user interface. Sensor 130 may also be linked to monitor 140 so that monitoring and programming of medication delivery may be performed remotely. Alternatively sensor 130 may communicate directly with devices in the external network space, e.g., via Bluetooth, ZigBee or the like.

Local devices can process the received sensor data in an appropriate manner. For example, portable display device 132, remote control device 134, BG meter 136, command display controller 138, monitor 140, or infusion pump 128 may display the current BG level derived from the received sensor data and/or generate an alert or otherwise indicate low or high BG levels. As another example, BG meter 136 or infusion pump 128 may process the received sensor data for purposes of calibration. As yet another example, infusion pump 128 may be configured to activate its infusion mechanism in response to the received sensor data. Moreover, sensor data could be processed in one or more of the local devices and/or in one or more of network devices 104. In this regard, system 100 may utilize distributed processing techniques for the handling of sensor data.

Any of the devices within local infusion system 102 may include a display and related processing logic that facilitates the display of physiologic patient data, device status information, time and date information, alarm/alert status, and other information related to the operation, status, or condition of the patient, related to any of the devices within local infusion system 102, or related to local infusion system 102 itself. Portable display device 132 may be realized as a small device having limited functionality. In this regard, portable display device 132 may be incorporated into a key fob, a carabiner, a pendant, an insulin pen, a credit card display, or the like. Other local devices may have expanded display capabilities related to the specific functionality of such devices. For example, BG meter 136 may include display features that are specific to its metering functionality.

BG meter 136 is generally configured to measure the BG level of a user by analyzing a blood sample. For example, BG meter 136 may include a receptacle for receiving a blood sample test strip. In this regard, the user inserts a test strip into the BG meter 136, which analyzes the sample and displays a BG level corresponding to the test strip sample. BG meter 136 may be configured to generate a local communication, which conveys the measured BG level, for transmission to other local devices within local infusion system 102. Depending upon the specific application, BG meter 136 may also include the functionality of a monitoring device for infusion pump 128 and/or the functionality of a controller device for infusion pump 128.

Command display controller 138 is preferably realized as a handheld monitor/controller device that, although physically separate from infusion pump 128, enables the user to monitor and control the operation of infusion pump 128. This allows the user to operate infusion pump 128 without physically handling the device. As described in more detail below, command display controller 138 includes a communication module for transmitting local communications or commands to infusion pump 128. In further embodiments, command display controller 138 may receive local communications sent from infusion pump 128 or other components within local infusion system 102. In example embodiments, command display controller 138 also includes a network communication module for handling network communications to and from network devices that are external to local infusion system 102. Further, command display controller 138 may include one or more user input elements on its housing, such as keys, buttons, or the like, which accommodate user inputs. In embodiments, command display controller 138 includes a display on its housing, which may be configured to concurrently reproduce at least a portion of the information displayed on infusion pump 128.

Monitor 140, which may be realized as a bedside monitor for personal use or as a hospital monitor for caregiver use, enables remote monitoring of infusion pump 128 (and possibly other devices within local infusion system 102). Monitor 140 and other monitors described herein may be utilized in applications that do not utilize infusion pump 128; for example, applications that monitor patient data (such as glucose levels). In addition, monitor 140 may be suitably configured to enable remote programming and control of infusion pump 128 and/or other devices within local infusion system 102. In this regard, a "monitor" as used herein can generally refer to a monitor-only device or a monitor-controller device. In practice, monitor 140 is a relatively large device in comparison to portable or handheld devices of infusion system 102. In contrast to remote control device 134, portable display device 132, and command display controller 138, monitor 140 is intended to be somewhat stationary and not carried by the user. For example, a bedside monitor may be located on a nightstand beside the patient's bed, while a hospital monitor may be located on a medical equipment cart or stand in the patient's room. In contrast to the smaller portable devices of local infusion system 102, monitor 140 preferably includes a large and easy to read display element, which may be configured to concurrently reproduce at least a portion of the information displayed on infusion pump 128.

As described above in connection with command display controller 138, monitor 140 may also be configured to allow the user to remotely operate infusion pump 128. Monitor 140 may include a communication module for receiving and/or transmitting local communications within local infusion system 102. Moreover, monitor 140 may include a network communication module for handling network communications to and from network devices that are external to local infusion system 102. Further, monitor 140 may include one or more user input elements on its housing, such as keys, buttons, or the like, which accommodate user inputs.

As shown in FIG. 1, local infusion system 102 is capable of establishing many potential communication paths between the local devices. In embodiments, a controller device (e.g., remote control device 134, command display controller 138, or monitor 140) may serve as a translator between infusion pump 128 and the other components of local infusion system 102, such as BG meter 136. For example, the controller device may have the ability to determine how best to translate data received from infusion pump 128 for compatibility with the display requirements of a destination device within local infusion system 102. As depicted in FIG. 1, infusion pump 128 may communicate directly with BG meter 136. In some embodiments, local infusion system 102 may include multiple controllers that can communicate with infusion pump 128. In other embodiments, only one controller device can communicate with infusion pump 128 at any given moment. The controller device functionality may also be integrated into infusion pump 128 in some embodiments. In yet another embodiment, BG meter 136 may be integrated into the controller device such that both features share a single device housing.

Figure 2:
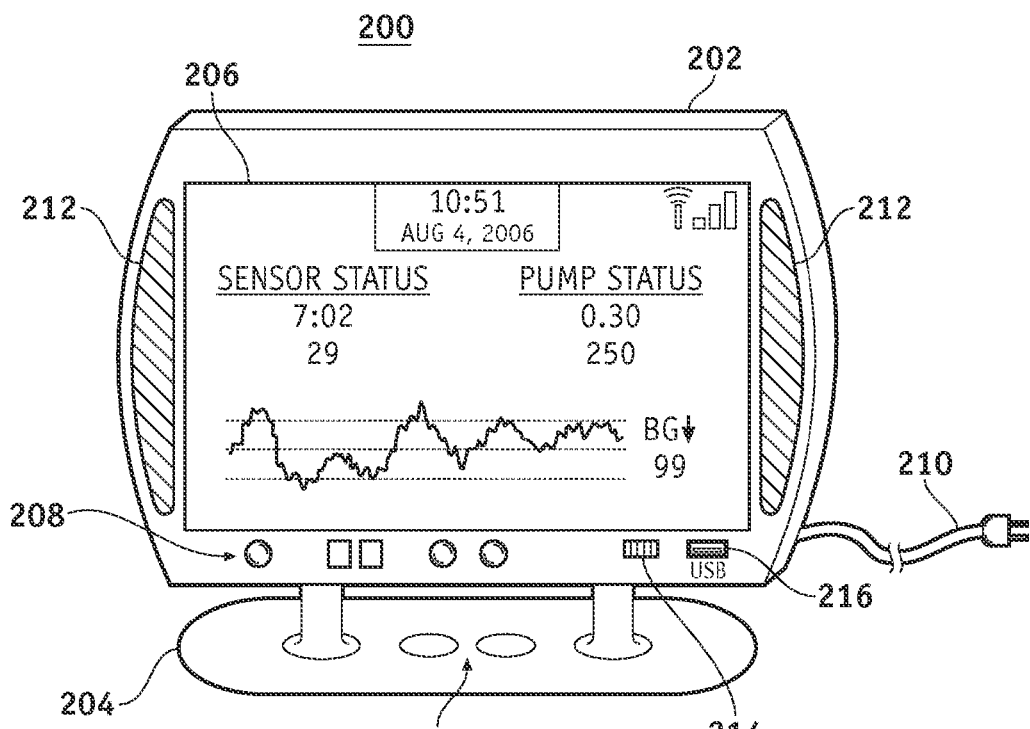
FIG. 2 is a front view of a bedside infusion system monitor configured in accordance with an example embodiment of the invention.

FIG. 2 is a front view of an example bedside monitor 200 configured in accordance with an example embodiment of the invention. Referring to FIG. 1, bedside monitor 200 may be deployed in local infusion system 102 (as monitor 140) and/or as a network device 104 (e.g., as monitor 114). Bedside monitor 200 may, but need not, be utilized to monitor the activity of an insulin infusion pump. Bedside monitor 200 generally includes a housing 202, a stand 204 that supports housing 202, a display element 206, and user interface features 208. Embodiments of bedside monitor 200 may include an AC power plug 210, one or more speakers 212, one or more local device interfaces 214, and one or more network interfaces 216.

As mentioned above, bedside monitor 200 is intended to be used as a somewhat stationary fixture placed in a suitable location, such as on the patient's nightstand. In other words, bedside monitor 200 is not designed to be a portable or handheld component. Therefore, housing 202 may be sized to accommodate a relatively large display element 206, which may utilize any known display technology (e.g., a cathode ray tube, an LCD panel, or a plasma panel). The size of display element 206 may vary to suit the needs of the particular application; typical sizes can range from 10 diagonal inches to 20 diagonal inches. Housing 202 may also be configured to accommodate integral speakers 212, which can be activated to generate alarm or alert notifications. Housing 202 may also be designed to accommodate user interface features 208 as shown in FIG. 2. Stand 204 is suitably configured to support housing 202 and to provide a stable mounting location for bedside monitor 200. In the example embodiment shown in FIG. 2, stand 204 is also configured to accommodate one or more user interface features 208. User interface features 208 may include a keypad, keys, buttons, switches, knobs, a touchpad, a joystick, a pointing device, a virtual writing tablet, or any device, component, or function that enables the user to select options, input information, or otherwise control the operation of bedside monitor 200.

Bedside monitor 200 may include processing logic, a display driver, and memory (not shown in FIG. 2) that is suitably configured to display information on display element 206. In embodiments, bedside monitor 200 functions to display information requested by the user, to display information related to an instructed act that was undertaken by the infusion pump, or to display status data for the infusion pump, such as, for example, BG levels, BG trends or graphs, or fluid delivery information. Bedside monitor 200 may be configured to display information conveyed in local communications received from an infusion pump or from any device within the local infusion system. At any moment, display element 206 may show substantially the same information as shown on the infusion pump; the two displays may mimic one another so that the user may choose to conveniently view the selected information from bedside monitor 200 rather than from the infusion pump, which is usually attached to the patient's body through an infusion set. Display element 206 may also include a backlight to facilitate viewing. The backlight may be a user programmable multi-color backlight that additionally performs the function of a visual indicator by flashing colors appropriate to the level of an alert or alarm. The backlight may also have variable intensity (automatic or manual) to accommodate user preferences and/or to indicate different alert or alarm status.

As described in more detail below, bedside monitor 200 may include one or more communication modules (not shown in FIG. 2) that facilitate data communication between bedside monitor 200 and other local devices within the local infusion system and/or data communication between bedside monitor 200 and network devices that are external to the local infusion system. For example, a local communication module may cooperate with a local device interface to receive local communications from local devices and/or to transmit local communications to local devices. The local communication module and local device interface may be configured to support wireless and/or wired data communication protocols. In an embodiment, local device interface 214 may represent a physical interface (such as a plug, a jack, a connector, a USB port, etc.) that facilitates connection to a data communication cable or any suitably configured physical component that establishes a communication link to a local device. As another example, a network communication module may cooperate with a network interface to receive network communications from network devices and/or to transmit network communications to network devices. The network communication module and network interface may be configured to support wireless and/or wired data communication protocols. In an embodiment, network interface 216 may represent a physical interface (such as a plug, a jack, a connector, a USB port, etc.) that accommodates a data communication cable or any suitably configured physical component that establishes a communication link to a network device. Bedside monitor 200 may also utilize one or more wireless local device interfaces and one or more wireless network interfaces, however, such wireless interfaces may not be visible from points outside housing 202.

Figure 3:
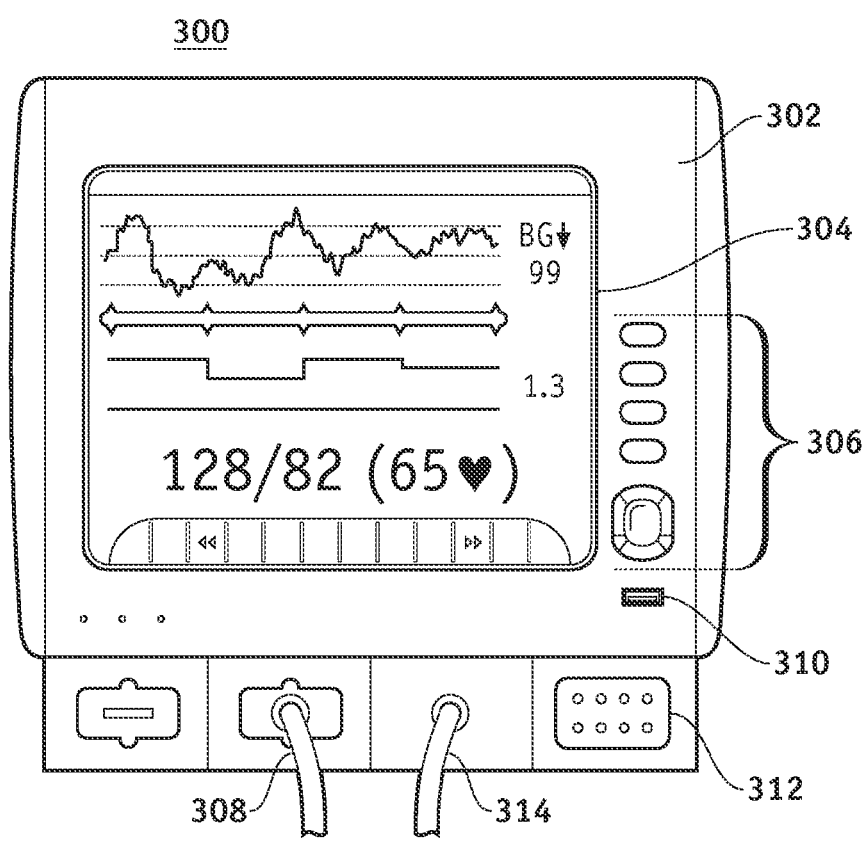
FIG. 3 is a front view of a hospital infusion system monitor configured in accordance with an example embodiment of the invention.

FIG. 3 is a front view of an example hospital monitor 300 configured in accordance with an example embodiment of the invention. Hospital monitor 300 is similar to bedside monitor 200, and both monitors include some shared features and functionality. For the sake of brevity, such common features and functions will not be redundantly described here. Hospital monitor 300 is generally configured to display and/or process information in an appropriate manner. Such information may be, for example, alarms, alerts, or any of the information or data types described above with respect to FIG. 1, regardless of the location or device that originally generated or processed such information/data. Generally, referring to FIG. 1, hospital monitor 300 may be deployed in local infusion system 102 (as monitor 140) and/or as a network device 104 (e.g., as monitor 114). Hospital monitor 300 generally includes a housing 302, a display element 304, user interface features 306, an AC power plug 308, one or more speakers (hidden from view in FIG. 3), one or more local device interfaces 310, and one or more network interfaces 312. In this example embodiment, hospital monitor 300 also includes an integrated infusion pump that delivers fluid to the patient via a delivery tube 314.

Hospital monitor 300 is intended to be used as a somewhat stationary fixture placed in a suitable location, such as on a cart or an equipment rack in the patient's room. In other words, hospital monitor 300 is not designed to be a portable or handheld component. Hospital monitor 300 is suitably configured to operate substantially as described above with respect to bedside monitor 200. In contrast to bedside monitor 200, however, hospital monitor 300 may include an infusion pump and control features related to the operation of the infusion pump. Moreover, hospital monitor 300 may employ a network communication module and a network interface that cooperate to receive network communications from hospital network devices and/or to transmit network communications to hospital network devices. As used here, a "hospital network" refers to any number of physical or logical components, including hardware, software, firmware, and/or processing logic configured to support data communication between an originating component and a destination component, where data communication is carried out in accordance with one or more communication protocols that are reserved for, or utilized in, hospital environments.

Figure 4A:
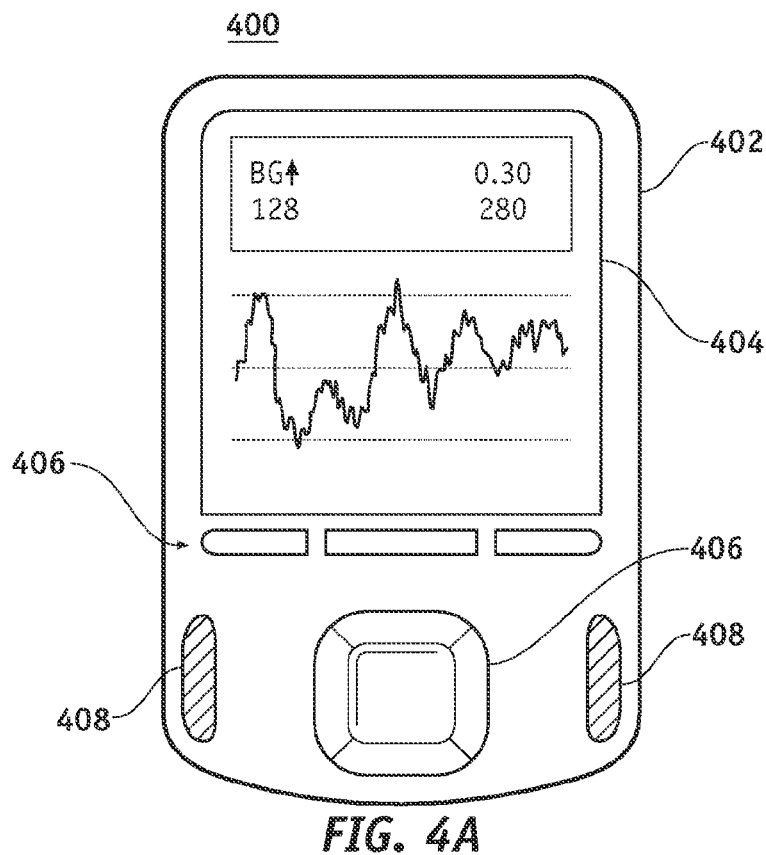
FIG. 4A is a front view of a handheld infusion system monitor/controller configured in accordance with example embodiment of the invention.

FIG. 4A is a front view of a handheld monitor/controller 400 configured in accordance with an example embodiment of the invention. Handheld monitor/controller 400 is similar to bedside monitor 200, and both monitors include some shared features and functionality. For the sake of brevity, such common features and functions will not be redundantly described here. Referring to FIG. 1, handheld monitor/controller 400 may be deployed in local infusion system 102 (as command display controller 138 or remote control device 134) and/or as a network device 104 (e.g., as personal digital assistant 120). Handheld monitor/controller 400 generally includes a housing 402, a display element 404, user interface features 406, one or more speakers 408, one or more local device interfaces (not shown), and one or more network interfaces (not shown).

Handheld monitor/controller 400 is intended to be used as a portable and mobile device that can be carried by the user. In particular embodiments, handheld monitor/controller 400 supports wireless communication with the patient's infusion pump, and the telemetry range of handheld monitor/controller 400 is localized. Handheld monitor/controller 400 is suitably configured to operate substantially as described above in connection with bedside monitor 200. Although the example embodiment utilizes a wireless local device interface and a wireless network interface, handheld monitor/controller 400 may also include wired interfaces to accommodate direct physical connections to other devices within the local infusion system and/or to network devices external to the local infusion system.

The power of handheld monitor/controller 400 (and of the other portable devices discussed here) may be provided by a battery. The battery may be a single use or a rechargeable battery. Where the battery is rechargeable, there may be a connector or other interface on handheld monitor/controller 400 for attaching the device to an electrical outlet, docking station, portable recharger, or so forth to recharge the battery while the battery remains in housing 402. It is also possible that a rechargeable battery may be removable from housing 402 for external recharging. In practice, however, the rechargeable battery may be sealed into housing 402 to create a more water resistant or waterproof component. In further embodiments, handheld monitor/controller 400 may be adapted to accommodate more than one type of battery. For example, handheld monitor/controller 400 may be configured to accommodate a rechargeable battery and (for backup or emergency purposes) a readily available battery type, such as a AA battery, a AAA battery, or a coin cell battery.

Figure 4B:
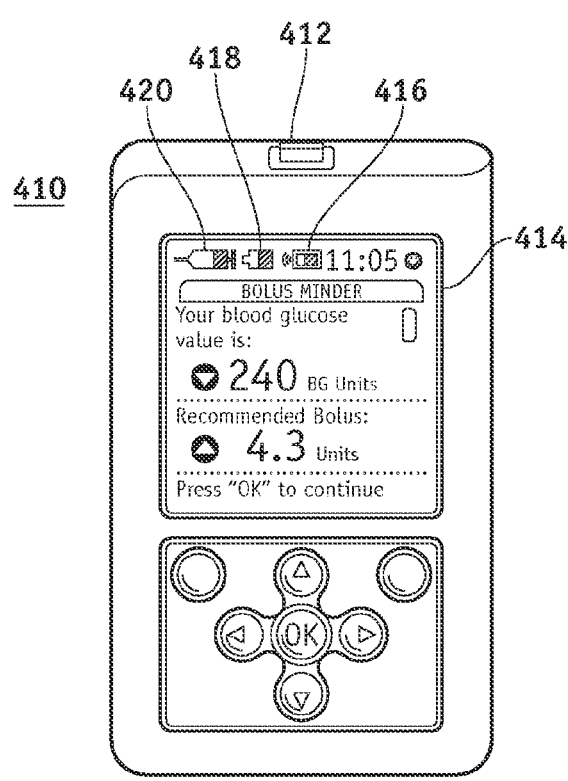
FIG. 4B is a front view of a handheld infusion system monitor/controller configured in accordance with another example embodiment of the invention.

FIG. 4B is a front view of a handheld monitor/controller 410 configured in accordance with another example embodiment of the invention. Handheld monitor/controller 410 is similar to handheld monitor/controller 400, and both devices include some shared features and functionality. For the sake of brevity, such common features and functions will not be redundantly described here.

Handheld monitor/controller 410 preferably includes wireless data communication functionality that enables it to handle wireless local communications and/or wireless network communications. In addition, handheld monitor/controller 410 may include a wired or cabled network interface 412, which may be realized as a cable connector, jack, plug, or receptacle. FIG. 4B depicts example content displayed on a display element 414 of handheld monitor/controller 410. This content represents one particular "screen shot" for handheld monitor/controller 410; in practice any number of different display screens can be generated to suit the intended functionality and features of the device. The example screen shot of FIG. 4B includes a clock display, an RF quality indicator 416, a battery indicator 418, a fluid level indicator 420 that represents the amount of fluid remaining in the infusion pump, a current BG value for the patient (240 in this example), and a recommended bolus (4.3 units in this example). Handheld monitor/controller 410 may also display one or more prompts that provide guidance or instruction to the user. In this example, display element 414 includes the prompt: "Press 'OK' to Continue". The user can press "OK" to display other options, such as an activation request that controls the infusion pump to administer the recommended bolus.

Figure 5:
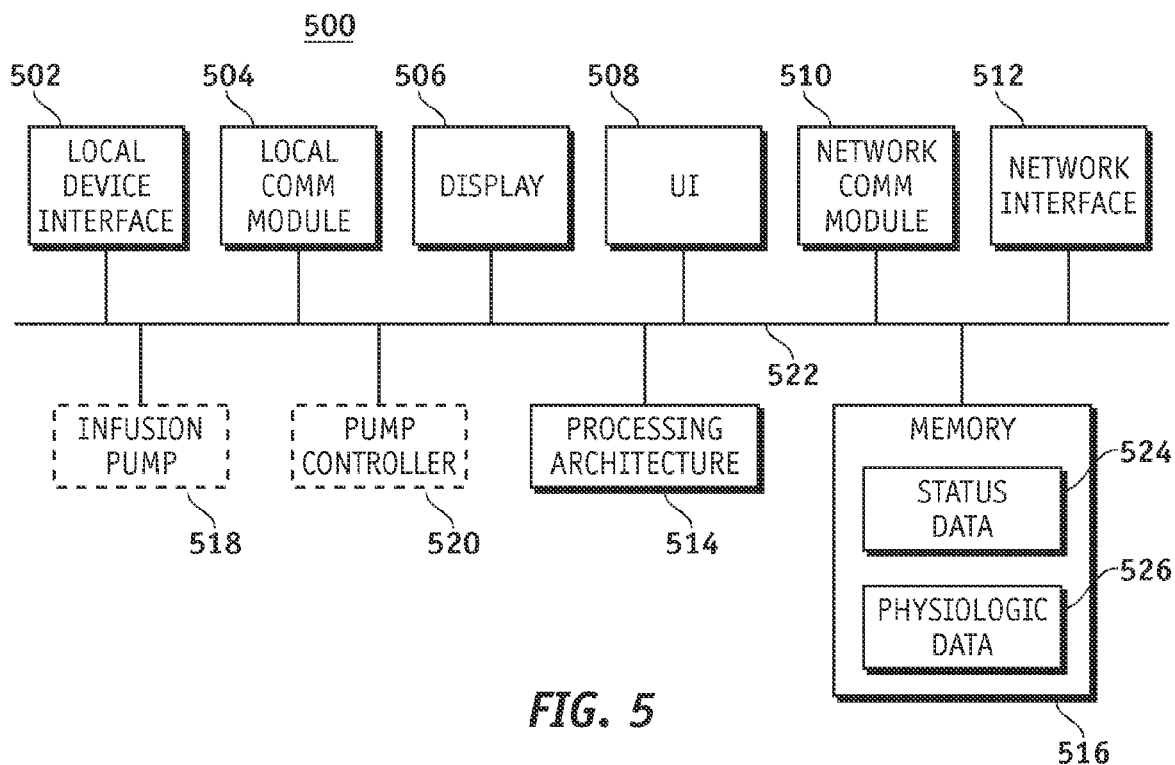
FIG. 5 is a schematic representation of an infusion system monitor configured in accordance with an example embodiment of the invention.

FIG. 5 is a schematic representation of a medical device system monitor 500 configured in accordance with an example embodiment of the invention. Monitor 500 represents a generalized embodiment that may be realized as a bedside monitor, a hospital monitor, or a handheld monitor/controller, depending upon its specific configuration. In this example, monitor 500 generally includes a local device interface 502, a local communication module 504, a display element 506, one or more user interface features 508, a network communication module 510, a network interface 512, a processing architecture 514, and a suitable amount of memory 516. If monitor 500 is implemented as a hospital monitor, then it may also include an infusion pump 518 and a pump controller 520 that controls the operation of infusion pump 518 (these elements are depicted in dashed lines to indicate their optional nature). The elements of monitor 500 may be coupled together via a bus 522 or any suitable interconnection architecture.

Those of skill in the art will understand that the various illustrative blocks, modules, circuits, and processing logic described in connection with monitor 500 (and other devices, elements, and components disclosed here) may be implemented in hardware, computer software, firmware, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, or software depends upon the particular application and design constraints imposed on the embodiment. Those familiar with the concepts described here may implement such functionality in a suitable manner for each particular application, but such implementation decisions should not be interpreted as causing a departure from the scope of the present invention.

Referring again to FIG. 5, display element 506 and user interface features 508 were described above in connection with bedside monitor 200, hospital monitor 300, and handheld monitor/controller 400. Briefly, display element 506 is suitably configured to enable monitor 500 to display physiologic patient data, local device status information, clock information, alarms, alerts, and any information/data received or processed by monitor 500. For example, display element 506 may be controlled to indicate an alert or alarm status when monitor 500 receives an incoming communication (from a local device within the infusion system or from a network device external to the infusion system) that conveys an alert signal or an alarm signal. User interface features 508 enable the user to control the operation of monitor 500. In one example embodiment, user interface features 508 enable the user to control the operation of one or more additional devices within the local infusion system, for example, an infusion pump. Moreover, monitor 500 may be configured such that user interface features 508 can be manipulated to control the operation of one or more network devices that are external to the local infusion system.

Processing architecture 514 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor may be realized as a microprocessor, a controller, a microcontroller, or a state machine. Moreover, a processor may be implemented as a combination of computing devices, e.g., a combination of a digital signal processor and a microprocessor, a plurality of microprocessors, one or more microprocessors in conjunction with a digital signal processor core, or any other such configuration.

In practice, processing architecture 514 may be suitably configured to interpret and process incoming information, data, and content that is conveyed in local communications received from a transmitting device within the local infusion system. Referring to FIG. 1, the transmitting device may be any of the devices within local infusion system 102, including another monitor device. Such incoming information may include, without limitation: physiologic data of the user, such as a BG level (a calibrated reading or a raw measured value); status information of the transmitting local device (e.g., a battery life indication, a power on/off status, a transmit signal power level, diagnostic information indicating results of self tests); an alert signal related to operation of the transmitting local device (e.g., a low battery alert, an out of range alert, a calibration reminder); a basal rate of fluid delivered to the user by an infusion pump; bolus information for a bolus of fluid delivered to the user by an infusion pump; advisory information for the patient (e.g., a notification to place an order for supplies, a reminder to schedule a doctor's appointment, a reminder to schedule or automatically execute a data download for analysis by a caregiver, a notification to perform routine diagnostics, either manually or remotely via a network connection); or the like.

Processing architecture 514 may also be configured to interpret and process incoming information, data, and content that is conveyed in network communications generated by an originating device that is external to the local infusion system. Referring to FIG. 1, the originating device may be any network device 104, including a networked monitor device. Such incoming network information may include, without limitation: programming data for a local device within the infusion system; an activation instruction for an infusion pump or another local device within the infusion system; a status request for a local device within the infusion system; a request for physiologic data of the user; an alert or alarm enable or disable instruction for a local device within the infusion system (which may be processed by monitor 500 and/or routed by monitor 500 to the appropriate local device); advisory information for the patient (e.g., a notification to place an order for supplies, a reminder to schedule a doctor's appointment, a reminder to schedule or automatically execute a data download for analysis by a caregiver, a notification to perform routine diagnostics, either manually or remotely via a network connection); or the like.

Memory 516 may be realized as RAM memory, flash memory, EPROM memory, EEPROM memory, registers, a hard disk, a removable disk, a CD-ROM, or any other form of storage medium known in the art. In this regard, memory 516 can be coupled to processing architecture 514 such that processing architecture 514 can read information from, and write information to, memory 516. In the alternative, memory 516 may be integral to processing architecture 514. As an example, processing architecture 514 and memory 516 may reside in an ASIC. In this example, memory 516 may be utilized to store device status data 524 and/or physiologic data 526 of the user, where such data is communicated to monitor 500 via local communications, network communications, or directly (for example, if monitor 500 is configured to receive BG data directly from a test strip or via direct user input).

Monitor 500 may be configured to communicate with a remote database or databank that is accessible via a network connection. Referring to FIG. 1, for example, a network device 104 in system 100 may be realized as a network database 126 that provides data to monitor 500. In such an embodiment, monitor 500 can download data from the remote database as necessary, store it in memory 516 if needed, or otherwise process the downloaded data in an appropriate manner.

An embodiment of monitor 500 may employ any number of local communication modules 504 and any number of local device interfaces 502. For simplicity, the example described here employs one local communication module 504 and one local device interface 502. Local communication module 504 and local device interface 502 are suitably configured to support local communications between monitor 500 and devices within the local infusion system (e.g., any of the devices in infusion system 102 shown in FIG. 1). Depending upon the particular implementation, local communication module 504 and local device interface 502 may be configured to support unidirectional communication from monitor 500 to one or more local devices, unidirectional communication from one or more local devices to monitor 500, or bidirectional communication between monitor 500 and one or more local devices. Thus, local device interface 502 may be configured to receive a local communication from a transmitting device within the local infusion system, and/or to transmit a local communication to a receiving device within the local infusion system. Moreover, depending upon the particular implementation, local communication module 504 and local device interface 502 may be configured to support wireless data communication, wired/cabled data communication, or both.

For wireless transmissions of local communications, local communication module 504 and local device interface 502 support one or more wireless data communication protocols that are also supported by the local device(s) communicating with monitor 500. Any number of suitable wireless data communication protocols, techniques, or methodologies may be supported by monitor 500, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In an embodiment, a wireless local device interface 502 may include or be realized as hardware, software, and/or firmware, such as an RF front end, a suitably configured radio module (which may be a stand alone module or integrated with other or all functions of the device), a wireless transmitter, a wireless receiver, a wireless transceiver, an infrared sensor, an electromagnetic transducer, or the like.

For transmissions of local communications over a cable, a wired connection, or other physical link, local communication module 504 and local device interface 502 support one or more wired/cabled data communication protocols that are also supported by the local device(s) communicating with monitor 500. Any number of suitable data communication protocols, techniques, or methodologies may be supported by monitor 500, including, without limitation: Ethernet; home network communication protocols; USB; IEEE 1394 (Firewire); hospital network communication protocols; and proprietary data communication protocols. In an embodiment, a wired/cabled local device interface 502 may include or be realized as hardware, software, and/or firmware, such as a suitably configured and formatted port, connector, jack, plug, receptacle, socket, adaptor, or the like.

An embodiment of monitor 500 may employ any number of network communication modules 510 and any number of network interfaces 512. For simplicity, the described example employs one network communication module 510 and one network interface 512. Network communication module 510 and network interface 512 are suitably configured to support network communications between monitor 500 and network devices that are external to the local infusion system (e.g., one or more of the network devices 104 shown in FIG. 1). Depending upon the particular implementation, network communication module 510 and network interface 512 may be configured to support unidirectional communication from monitor 500 to one or more network devices, unidirectional communication from one or more network devices to monitor 500, or bidirectional communication between monitor 500 and one or more network devices. Thus, network device interface 512 may be configured to receive an incoming network communication from an originating network device, and/or to enable transmission of an outgoing network communication to a receiving network device. Moreover, depending upon the particular implementation, network communication module 510 and network interface 512 may be configured to support wireless data communication, wired/cabled data communication, or both.

For wireless transmissions of network communications, network communication module 510 and network interface 512 support one or more wireless data communication protocols that are also supported by the network device(s) communicating with monitor 500. Any number of suitable wireless data communication protocols, techniques, or methodologies may be supported by monitor 500, including, without limitation, the wireless protocols listed above. In an embodiment, a wireless network interface 512 may include or be realized as hardware, software, and/or firmware, as described above for a wireless local device interface 502.

For transmissions of network communications over a cable, a wired connection, or other physical link, network communication module 510 and network interface 512 support one or more wired/cabled data communication protocols that are also supported by the network device(s) communicating with monitor 500. Any number of suitable data communication protocols, techniques, or methodologies may be supported by monitor 500, including, without limitation, the wired or cable based protocols listed above. In an embodiment, a wired/cabled network interface 512 may include or be realized as hardware, software, and/or firmware, as described above for a wired/cabled local device interface 502.

Figure 6:
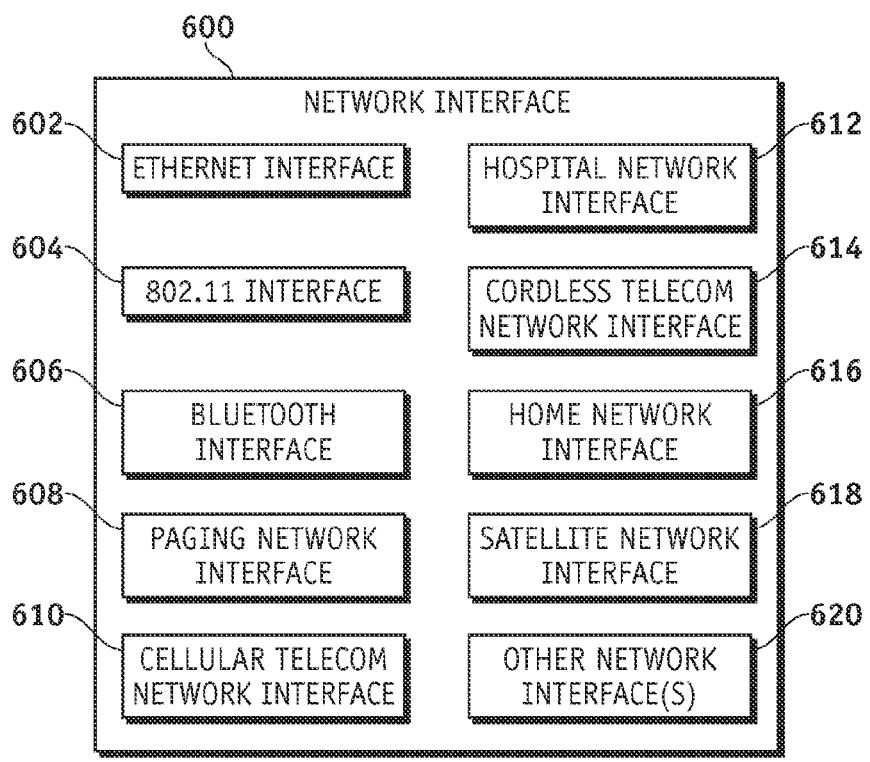
FIG. 6 is a schematic representation of a network interface suitable for use with the infusion system monitor depicted in FIG. 5.

FIG. 6 is a schematic representation of a generalized network interface 600 suitable for use with monitor 500. For ease of description, network interface 600 is depicted as a general interface that includes a number of wireless and wired/cabled data communication aspects. Network interface 600 need not include multiple interfaces as depicted in FIG. 6 and, indeed, an embodiment may utilize only one specific type of interface. Network interface 600 generally includes an Ethernet interface 602, an 802.11 interface 604, a Bluetooth interface 606, a paging network interface 608, a cellular telecommunication network interface 610, a hospital network interface 612, a cordless telecommunication network interface 614, a home network interface 616, a satellite network interface 618, and other network interfaces 620.

Ethernet interface 602 may include or be realized as hardware, software, and/or firmware that is suitably configured to cooperate with network communication module 510 to accommodate Ethernet compliant network data communications with one or more network devices. For example, Ethernet interface 602 may include a T-568A Ethernet connector, a T-568B Ethernet connector, an RJ-45 connector, or any connector that is compatible with Ethernet cables.

802.11 interface 604 may include or be realized as hardware, software, and/or firmware that is suitably configured to cooperate with network communication module 510 to accommodate 802.11 compliant network data communications with one or more network devices. For example, 802.11 interface 604 may include an appropriate radio module, an 802.11 transceiver card, an RF front end, an RF antenna, and/or 802.11 access point functionality.

Bluetooth interface 606 may include or be realized as hardware, software, and/or firmware that is suitably configured to cooperate with network communication module 510 to support Bluetooth compliant network data communications with one or more network devices. For example, Bluetooth interface 606 may include an appropriate radio module, a Bluetooth transceiver, an RF front end, and/or an RF antenna.

Paging network interface 608 may include or be realized as hardware, software, and/or firmware that is suitably configured to cooperate with network communication module 510 to support network communications in compliance with a paging network protocol. For example, paging network interface 608 may include an appropriate radio module, a transceiver card, an RF front end, and/or an RF antenna.

Cellular telecommunication network interface 610 may include or be realized as hardware, software, and/or firmware that is suitably configured to cooperate with network communication module 510 to accommodate network communications in compliance with a cellular telecommunication protocol (e.g., CDMA, GSM, or the like). For example, cellular telecommunication network interface 610 may include an appropriate radio module, a transceiver card, an RF front end, and/or an RF antenna.

Hospital network interface 612 may include or be realized as hardware, software, and/or firmware that is suitably configured to cooperate with network communication module 510 to support network communications in compliance with a hospital network protocol. In embodiments, the hospital network protocol may be a wireless data communication protocol or a wired/cabled data communication protocol. In this regard, a wireless hospital network interface 612 may include an appropriate radio module, a transceiver card, an RF front end, an RF antenna, an infrared transmitter, an infrared sensor, a magnetic induction transducer, or the like. Depending upon the particular deployment, a wireless hospital network interface 612 may be compliant with any of the other wireless/cordless data communication protocols described here. A wired/cabled hospital network interface 612 may include suitably configured connectors, sockets, jacks, plugs, or adaptors. Moreover, depending upon the particular application, a wired/cabled hospital network interface 612 may be compliant with any of the other wired/cabled data communication protocols described here.

Cordless telecommunication network interface 614 may include or be realized as hardware, software, and/or firmware that is suitably configured to cooperate with network communication module 510 to support network communications in compliance with a cordless telecommunication protocol. Such protocols are commonly used in household cordless telephone systems. In practice, cordless telecommunication network interface 614 may include an appropriate radio module, a cordless telephone base station, a transceiver card, an RF front end, and/or an RF antenna.

Home network interface 616 may include or be realized as hardware, software, and/or firmware that is suitably configured to cooperate with network communication module 510 to support network communications in compliance with a home network protocol. Such home network protocols may be utilized in the context of a home control system, a home computing network that leverages existing telephone wires or existing AC power lines, a home security or alarm system, a home entertainment system, or the like. In embodiments, the home network protocol may be a wireless data communication protocol or a wired/cabled data communication protocol. In this regard, a wireless home network interface 616 may include an appropriate radio module, a transceiver base station, a transceiver card, an RF front end, an RF antenna, an infrared transmitter, an infrared sensor, a magnetic induction transducer, or the like. Depending upon the particular deployment, a wireless home network interface 616 may be compliant with any of the other wireless/cordless data communication protocols described here. A wired/cabled home network interface 616 may include suitably configured connectors, sockets, jacks, plugs, or adaptors. Moreover, depending upon the particular application, a wired/cabled home network interface 616 may be compliant with any of the other wired/cabled data communication protocols described here.

Satellite network interface 618 may include or be realized as hardware, software, and/or firmware that is suitably configured to cooperate with network communication module 510 to accommodate network communications in compliance with a satellite data communication protocol. For example, satellite network interface 618 may include an appropriate radio module, a transceiver card, an RF front end, and/or an RF antenna. Alternatively (or additionally), satellite network interface 618 may include suitably configured connectors, sockets, jacks, plugs, or adaptors that facilitate wired/cabled connection to a separate piece of satellite network equipment, e.g., a satellite dish or a satellite transceiver module.

In practice, network interface 600 may utilize any number of network interfaces 620 other than the specific types described above. Such other network interfaces 620 can be suitably configured to support network communications in accordance with existing data communication protocols, whether publicly known or proprietary. Moreover, other network interfaces 620 enable network interface 600 to support wireless or wired data communication protocols that may be developed in the future.

Figure 7:
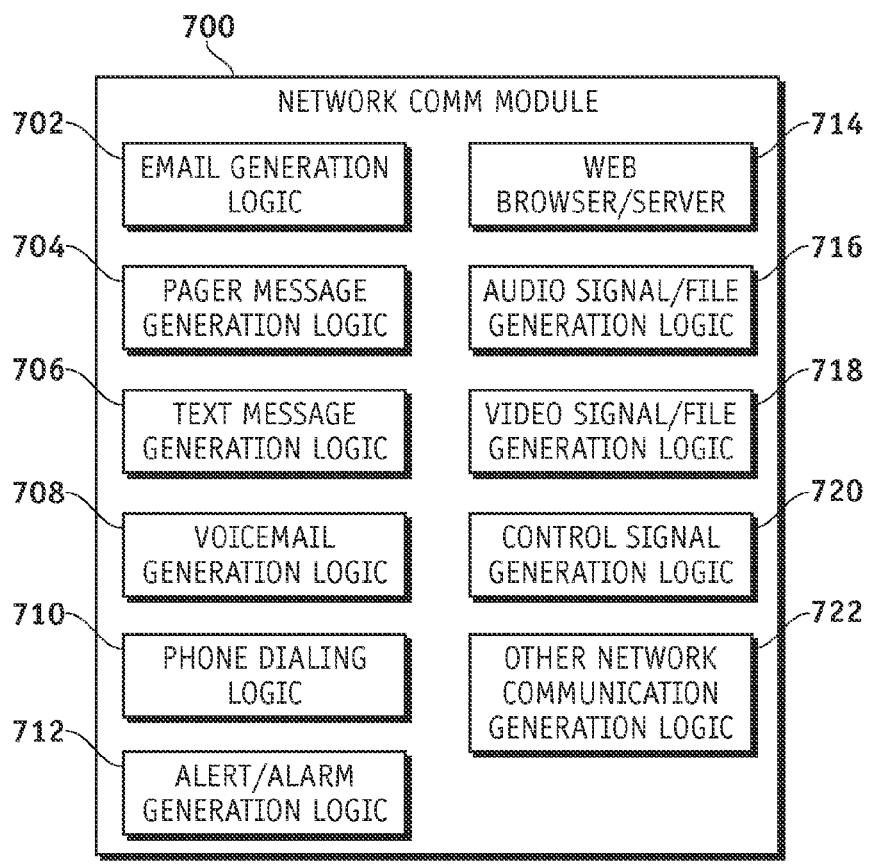
FIG. 7 is a schematic representation of a network communication module suitable for use with the infusion system monitor depicted in FIG. 5.

FIG. 7 is a schematic representation of a network communication module 700 suitable for use with monitor 500. For ease of description, network communication module 700 is depicted as a general module that includes processing logic for handling different types of network communications. In practice, network communication module 700 need not support different modes of network communications as depicted in FIG. 7 and, indeed, an embodiment may process only one specific network communication format or type. Network communication module 700 generally includes email generation logic 702, pager message generation logic 704, text message generation logic 706, voicemail generation logic 708, phone dialing logic 710, alert/alarm generation logic 712, a web browser/server 714, audio signal/file generation logic 716, video signal/file generation logic 718, control signal generation logic 720, and other network communication generation logic 722.

Email generation logic 702 may include or be realized as hardware, software, and/or firmware that is suitably configured to generate network communications as email. For example, email generation logic 702 may generate automatic or user-created email that conveys notifications, alerts, alarms, status reports, physiologic data, or other information that is intended for a destination network device. In embodiments, email generation logic 702 may be compatible with any suitable email system or technology, including web-based email systems.

Pager message generation logic 704 may include or be realized as hardware, software, and/or firmware that is suitably configured to generate network communications as pager messages. For example, pager message generation logic 704 may generate automatic or user-created pager messages that convey notifications, alerts, alarms, status reports, physiologic data, or other information that is intended for a pager device or any compatible destination network device. In embodiments, pager message generation logic 704 may be compatible with any suitable pager system or technology, including web-based paging systems.

Text message generation logic 706 may include or be realized as hardware, software, and/or firmware that is suitably configured to generate network communications as text messages. Such text messages may be carried over existing cellular telephone networks, existing pager networks, the Internet, local area networks, hospital networks, home networks, or the like. For example, text message generation logic 706 may generate automatic or user-created text messages that convey notifications, alerts, alarms, status reports, physiologic data, or other information that is intended for any compatible destination network device. In embodiments, text message generation logic 706 may be compatible with any suitable text messaging application or technology.

Voicemail generation logic 708 may include or be realized as hardware, software, and/or firmware that is suitably configured to generate network communications as voicemail messages. For example, voicemail message generation logic 708 may generate automatic or user-created voicemail messages that convey notifications, alerts, alarms, status reports, physiologic data, or other information that is intended for any compatible destination network device. In embodiments, such voicemail messages can be generated as audio files suitable for transmission as electronic attachments. Upon receipt, the destination network device can play the voicemail message using an appropriate playback mechanism, multimedia application, or the like. In embodiments, voicemail generation logic 708 may be compatible with any suitable voice messaging, telephone system, or multimedia application.

Phone dialing logic 710 may include or be realized as hardware, software, and/or firmware that is suitably configured to generate network communications as an outgoing telephone call. For example, phone dialing logic 710 may be configured to dial (automatically or in response to user interaction) an outgoing telephone number as needed to convey notifications, alerts, alarms, status reports, physiologic data, or other information that is intended for any compatible destination network device. Phone dialing logic 710 may also cooperate with one or more of the other logical components of network communication module 700, for example, voicemail generation logic 708, to facilitate transmission of certain network communications. In embodiments, phone dialing logic 710 may be compatible with any suitable telephone system or application.

Alert/alarm generation logic 712 may include or be realized as hardware, software, and/or firmware that is suitably configured to generate alerts and/or alarms intended for distribution to network devices. For example, alert/alarm generation logic 712 may generate automatic or user-created alerts or alarms that indicate any of the following, without limitation: battery status of a device within the local infusion system; when a physiologic characteristic of the patient crosses a predetermined threshold value; when a telemetered device within the local infusion system is out of range of the monitor; a scheduled calibration for a piece of equipment within the local infusion system; or any scheduled event related to the operation of the infusion system. In embodiments, alert/alarm generation logic 712 may cooperate with one or more of the other logical components of network communication module 700, for example, text message generation logic 706, to facilitate the formatting and network transmission of alerts and alarms. Upon receipt, the destination network device can generate an alert/alarm using an appropriate playback mechanism, multimedia application, an illuminating element, a speaker, or the like.

Web browser/server 714 represents a software application that is configured to generate network communications as markup language documents, e.g., HTML documents. Moreover, web browser/server 714 may include conventional web browsing capabilities that enable the monitor device to access web pages via the Internet. In this regard, web browser/server 714 may cooperate with one or more of the other logical components of network communication module 700, for example, email generation logic 702 or text message generation logic 706, to facilitate the transmission and receipt of certain network communications. Web browser applications and web server applications are well known and, therefore, will not be described in detail here.

Audio signal/file generation logic 716 may include or be realized as hardware, software, and/or firmware that is suitably configured to generate network communications as audio signals and/or audio files. The audio signals or files may be pre-programmed into the monitor device (or into the device that creates the audio signals or files). Alternatively, the audio signals or files may be created by a user of the monitor device (or by a user of the device in communication with the monitor device). For example, audio signal/file generation logic 716 may generate automatic or user-created audio signals or audio files that convey notifications, alerts, alarms, status reports, physiologic data, or other information that is intended for any compatible destination network device. Audio-based alerts/alarms may be automatically initiated by the monitor device or by a device in communication with the monitor device. Alternatively, audio-based alerts/alarms may be initiated by a user, patient, or caregiver at the monitor device or at a device in communication with the monitor device. Upon receipt, the destination network device can play the audio signals or audio files using an appropriate playback mechanism, multimedia application, or the like.

As used here, an audio signal may be a streaming audio signal, a broadcast radio signal, or a control signal that initiates the generation of audio at the destination network device, while an audio file represents a file that is received and interpreted by the destination network device (which then executes the audio file to generate audio). For example, audio signal/file generation logic 716 may be configured to generate MP3 audio files, WMA audio files, or the like. In this regard, audio signal/file generation logic 716 may cooperate with one or more of the other logical components of network communication module 700, for example, voicemail generation logic 708 or alert/alarm generation logic 712, to facilitate the transmission and receipt of certain network communications.

Video signal/file generation logic 718 may include or be realized as hardware, software, and/or firmware that is suitably configured to generate network communications as video signals and/or video files. The video signals or files may be pre-programmed into the monitor device (or into the device that creates the audio signals or files). Alternatively, the video signals or files may be created by a user of the monitor device (or by a user of the device in communication with the monitor device). For example, video signal/file generation logic 718 may generate automatic or user-created video signals or video files that convey notifications, alerts, alarms, status reports, physiologic data, or other information that is intended for any compatible destination network device. Video-based alerts/alarms may be automatically initiated by the monitor device or by a device in communication with the monitor device. Alternatively, video-based alerts/alarms may be initiated by a user, patient, or caregiver at the monitor device or at a device in communication with the monitor device. Upon receipt, the destination network device can play the video signals or video files using an appropriate playback mechanism, multimedia application, or the like.

As used here, a video signal may be a streaming video signal, a broadcast video signal, or a control signal that initiates the generation of video at the destination network device, while a video file represents a file that is received and interpreted by the destination network device (which then executes the video file to generate video). For example, video signal/file generation logic 718 may be configured to generate MPEG video files, JPG image files, or the like. In this regard, video signal/file generation logic 718 may cooperate with one or more of the other logical components of network communication module 700, for example, alert/alarm generation logic 712, to facilitate the transmission and receipt of certain network communications.

Control signal generation logic 720 may include or be realized as hardware, software, and/or firmware that is suitably configured to generate network communications as control signals for the receiving network device. For example, control signal generation logic 720 may generate automatic or user-created control signals that initiate the generation of notifications, alerts, alarms, displays, or otherwise control the operation of any compatible destination network device. Upon receipt of such a control signal, a destination network device will respond in a suitable manner—activating a display, activating a vibrating element, activating an illumination element, generating an audio or video response, or the like. In embodiments, control signal generation logic 720 may cooperate with one or more of the other logical components of network communication module 700, for example, alert/alarm generation logic 712, to facilitate the formatting and network transmission of control signals.

In practice, network communication module 700 may utilize other network communication generation logic 722 in lieu of, or in addition to, the specific types described above. Such other logical components can be suitably configured to generate network communications in various existing formats, whether publicly known or proprietary. Moreover, such other logical components enable network communication module 700 to support additional formats that may be developed in the future.

Figure 8:
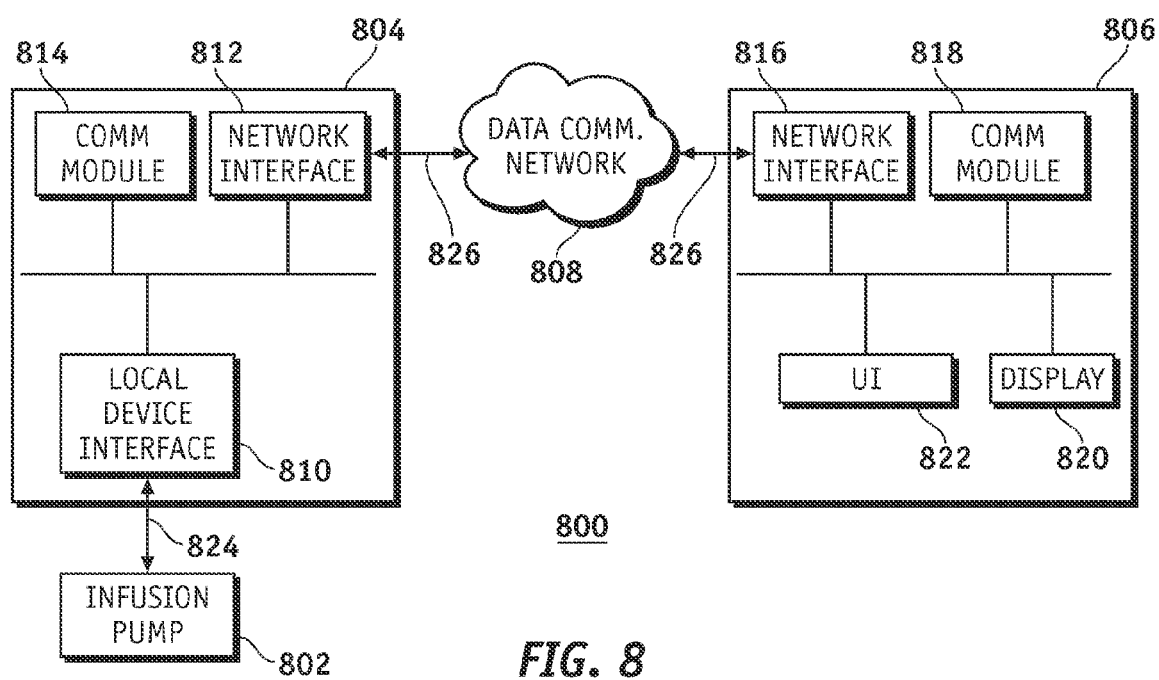
FIG. 8 is a schematic representation of a network-based infusion system configured in accordance with an example embodiment of the invention.

FIG. 8 is a schematic representation of a network-based medical device system 800 configured in accordance with an example embodiment of the invention. System 800 represents one simple implementation of a system that might utilize some of the devices, techniques, and methodologies described here. A vast number of alternative configurations may be constructed and operated within the scope of the invention. For example, although system 800 is described below in the context of an infusion pump, the infusion pump is not a requirement for embodiments of the invention.

Network-based infusion system 800 generally includes an infusion pump 802, a monitor device 804 (or any suitable local device that is defined to be within a local infusion system), and a network device 806. In this example embodiment, monitor device 804 and network device 806 communicate with each other via any number of network communication links established in a data communication network 808. Moreover, although not a requirement, FIG. 8 depicts bidirectional communications between monitor device 804 and network device 806. Network device 806 may be, for example, a network-based monitor, a networked computer, a cellular telephone or other mobile computing device, any network device 104 described in connection with FIG. 1, or any network-based device described elsewhere. Data communication network 808 may be (or include), for example, the Internet, a cellular telecommunication network, a paging system network, a local or wide area network, any wireless or wired network described in connection with FIG. 1, or any network described elsewhere.

As described in more detail in connection with FIG. 5, monitor 804 may include a local device interface 810, a network interface 812, and one or more suitable communication modules 814 (e.g., a local communication module and/or a network communication module). Network device 806 may include a network interface 816, which is configured for compatibility with network interface 812, one or more suitably configured communication modules 818, a display element 820, and user interface features 822. Network interface 816 may be configured as described above in connection with network interface 512 and in connection with network interface 600. Communication module(s) 818 may be configured as described above in connection with network communication module 510 and in connection with network communication module 700. Communication module(s) 818 are configured to enable network device 806 to receive, process, and interpret network communications received from monitor device 804. In addition, communication module(s) 818 may be configured to enable network device 806 to process, generate, and transmit outgoing network communications intended for monitor device 804. User interface features 822 and display element 820 enable a user of network device 806 to remotely view data that might be displayed at infusion pump 802 or monitor device 804, remotely control monitor device 804 or infusion pump 802, and/or remotely program or modify operating parameters of monitor device 804 or infusion pump 802.

In some embodiments of network-based infusion system 800, infusion pump 802 and monitor device 804 communicate using a first data communication protocol, while monitor device 804 and network device 806 communicate using a second data communication protocol (or a combination of protocols). Local communications between infusion pump 802 and monitor device 804 are carried over one or more local communication links 824, which may be wireless or wired. Network communications between monitor device 804 and network device 806 are carried over one or more network communication links 826, which may be wireless or wired. For example, infusion pump 802 may transmit local communications (such as pump status information) to monitor device 804, where the local communications are transmitted in accordance with a Bluetooth data communication protocol. Moreover, infusion pump 802 may receive incoming data from monitor device 804 using the same Bluetooth protocol. In contrast, monitor device 804 may transmit network communications (such as pump status information, alerts, or patient data) to network device 806, where the network communications are transmitted in accordance with a cellular telecommunication protocol such as CDMA. Similarly, monitor device 804 may receive incoming data from network device 806 using the same CDMA protocol.

Figure 9:
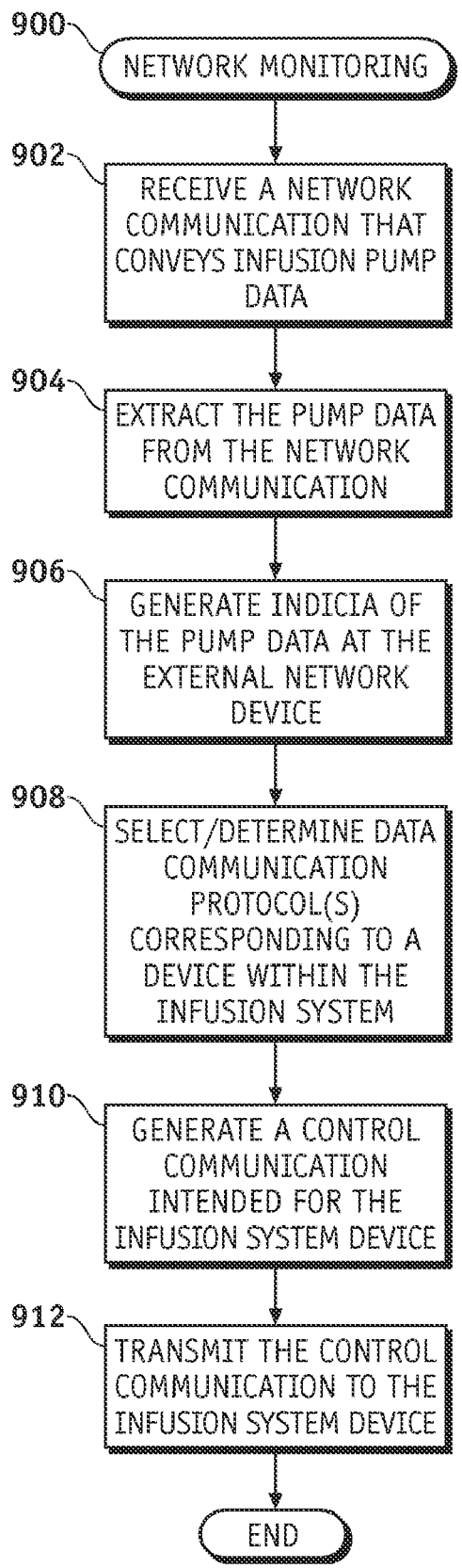
FIG. 9 is a flow chart that depicts an example network-based infusion system monitoring process.

FIG. 9 is a flow chart that depicts an example network-based medical device system monitoring process 900. The various tasks performed in connection with process 900 may be performed by software, hardware, firmware, or any combination. For illustrative purposes, the following description of process 900 may refer to elements mentioned above in connection with FIGS. 1-8. In embodiments, portions of process 900 may be performed by different elements of the described system, e.g., a network device or a functional element or operating component. It should be appreciated that process 900 may include any number of additional or alternative tasks, the tasks shown in FIG. 9 need not be performed in the illustrated order, and process 900 may be incorporated into a more comprehensive procedure or process having additional functionality not described in detail here.

Monitoring process 900 may be performed by a network device that is external to a local infusion system having an infusion pump that controls the infusion of fluid into the body of a user. Process 900 may begin when the network device receives (task 902) a network communication that conveys pump data associated with the local infusion pump. The network communication may be generated by (or originate at) any transmitting device within the local infusion system, such as a bedside monitor device, a hospital monitor device, a physiological characteristic meter, a remote controller, a handheld monitor/controller, the infusion pump itself, or the like. The pump data may include any information or content related to the operation, control, programming, or status of the infusion pump and/or the transmitting device, including, without limitation: physiologic data of the user/patient, alarms, alerts, graph or chart data, a basal rate of fluid delivered by the infusion pump, bolus information for a bolus of fluid delivered by the infusion pump, or any suitably formatted text, audio, or visual information. As described above in connection with FIG. 5 and FIG. 6, the network device may receive the network communication in compliance with one or more appropriate data communication protocols, including, without limitation: an Ethernet protocol, an IEEE 802.11 protocol (any variant), a Bluetooth protocol, a paging network protocol, a cellular telecommunication protocol (e.g., CDMA or GSM), a cordless telecommunication protocol, a home network data communication protocol, a satellite data communication protocol, a hospital network protocol, or any suitable wireless or wired/cabled data communication protocol that enables the network device to receive network communications via a wireless, cabled, and/or wired communication link.

In practice, the network device processes the received network communication and extracts (task 904) the pump data from the network communication. Task 904 may be performed by a suitably configured communication module and/or a suitably configured processing architecture resident at the network device. In response to such processing, the network device may generate (task 906) indicia of the pump data for display, playback, broadcast, or rendering at the network device. In connection with task 906, the network device may: generate indicia of received physiologic data; generate indicia of local device status information; generate indicia of an alert or an alarm; generate indicia of a basal rate of fluid delivery; generate indicia of bolus information; or the like. In embodiments, the network device may generate indicia of the pump data in any suitable manner, including, without limitation: generating an audible representation of the pump data, such as an audible alarm, alert, recording, or audio signal; generating a visual representation of the pump data, such as a graph or a text display; activating an illumination element of the network device, e.g., an indicator light or a flashing display screen; or activating a vibration element of the network device.

Monitoring process 900 assumes that the network device can transmit network communications back to a device within the local infusion system. In this regard, process 900 may select or determine (task 908) one or more data communication protocols corresponding to a local device within the infusion system. Task 908 may be performed to ensure that the network device utilizes an appropriate protocol for compatible communication with the local device. The network device may also obtain or generate an instruction or programming parameter intended for the infusion pump or another local device within the infusion system. Such instructions or programming parameters may be generated by the network device or obtained from an operator of the network device. The network device may be configured to generate (task 910) a suitably configured control communication that conveys the instruction or programming parameter. Depending upon the particular system deployment and the specific operating conditions, an example control communication may include, without limitation: an alert disable instruction; an activation instruction for the infusion pump or any local device; a programming parameter for the infusion pump or any local device; or the upload of software programs (main application code or auxiliary function code such as motor control, RF telemetry code, or the like). Eventually, the network device can transmit (task 912) the control communication in an appropriate format and in compliance with the particular data communication protocol utilized for the communication session with the local device. Upon receipt, the receiving local device can process the control communication in an appropriate manner.

In alternate embodiments of the invention, monitoring process 900 can be modified for use in connection with a medical device system that does not include an infusion pump. For example, the tasks of process 900 may be performed in an equivalent manner to receive and process a network communication that conveys patient data, monitor data, or other medical device information that might originate at a device within the local system, and such data need not include pump data.

Figure 10:
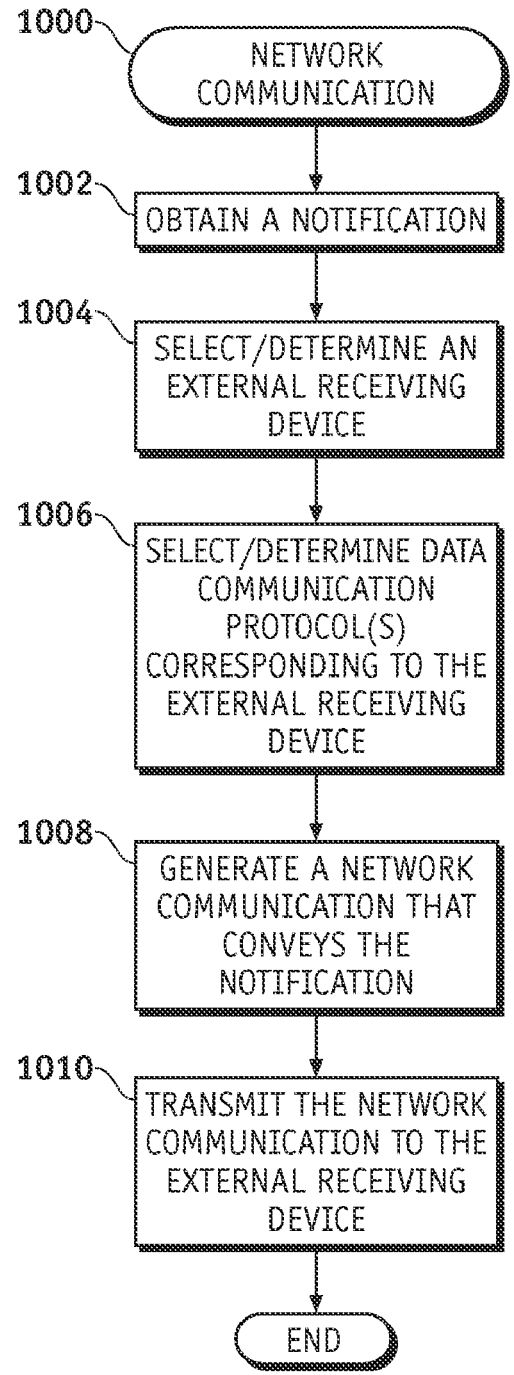
FIG. 10 is a flow chart that depicts an example network-based infusion system communication process.

FIG. 10 is a flow chart that depicts an example network-based medical device system communication process 1000. The various tasks performed in connection with process 1000 may be performed by software, hardware, firmware, or any combination of these. For illustrative purposes, the following description of process 1000 may refer to elements mentioned above in connection with FIGS. 1-8. In embodiments, portions of process 1000 may be performed by different elements of the described system, e.g., a local device within an infusion system or a functional element or operating component. It should be appreciated that process 1000 may include any number of additional or alternative tasks, the tasks shown in FIG. 10 need not be performed in the illustrated order, and process 1000 may be incorporated into a more comprehensive procedure or process having additional functionality not described in detail here.

Network communication process 1000 may be performed by a transmitting device that is within a local medical device system, e.g., an infusion system having an infusion pump that controls the infusion of fluid into the body of a user. For example, the transmitting device may be any local device within the local infusion system, such as a bedside monitor device, a hospital monitor device, a physiological characteristic meter, a physiological characteristic sensor transmitter, a remote controller, a handheld monitor/controller, the infusion pump itself, or the like. Process 1000 may begin when the transmitting device obtains (either internally, from another device, or from a user) or generates a notification (task 1002) related to the operation of the infusion pump and/or related to the operation of another local device. As used here, a notification may be any signal, alert, alarm, content, data, or information that is intended to be forwarded to another device, or is utilized as a prompt or a trigger to invoke a response by the transmitting device.

Network communication process 1000 may select or determine (task 1004) an external receiving device, which will be a network device in this example, that represents the intended recipient of the notification. In addition, process 1000 may select or determine (task 1006) one or more data communication protocols corresponding to the intended external receiving device. Task 1006 may be performed to ensure that the local transmitting device utilizes an appropriate protocol for compatible communication with the network device. As described above in connection with FIG. 5 and FIG. 6, the local device may transmit network communications in compliance with one or more appropriate data communication protocols, including, without limitation: an Ethernet protocol, an IEEE 802.11 protocol (any variant), a Bluetooth protocol, a paging network protocol, a cellular telecommunication protocol (e.g., CDMA or GSM), a cordless telecommunication protocol, a home network data communication protocol, a satellite data communication protocol, a hospital network protocol, or any suitable wireless or wired/cabled data communication protocol that enables the local device to transmit network communications via a wireless, cabled, and/or wired communication link.

The local transmitting device may then generate (task 1008) a network communication that conveys the notification, where the network communication is compatible with the selected data communication protocol. In accordance with embodiments, the network communication may include any information or content related to the operation, control, programming, or status of the infusion pump and/or the transmitting device, including, without limitation: physiologic data of the user/patient, alarms, alerts, graph or chart data, a basal rate of fluid delivered by the infusion pump, bolus information for a bolus of fluid delivered by the infusion pump, or any suitably formatted text, audio, or visual information. As described above in connection with FIG. 7, the network communication may be formatted as (or include) different message types, file types, or signal types, including, without limitation: an email message; a pager message; a text message; a voicemail message; an outgoing telephone call to the receiving network device; a markup language document, such as a web page; an audio signal; an audio file; a video signal; or a video file.

Eventually, the local transmitting device transmits (task 1010) the network communication to the external receiving device. The local device transmits the network communication in accordance with the network data communication protocol selected during task 1006. In one example, the network communication is conveyed in an outgoing telephone call, and the local transmitting devices transmits the network communication by initiating an outgoing telephone call to the destination network device. In other example embodiments, task 1010 represents the transmission of a message, file, and/or signal having a specified type and format. Upon receipt of the network communication, the destination network device can process the notification in an appropriate manner.

In alternate embodiments of the invention, process 1000 can be modified for use in connection with a medical device system that does not include an infusion pump. For example, the tasks of process 1000 may be performed in an equivalent manner to process and transmit a network communication that conveys patient data, monitor data, or other medical device information that might originate at a device within the local system, and such information need not include pump data.

Figure 11:
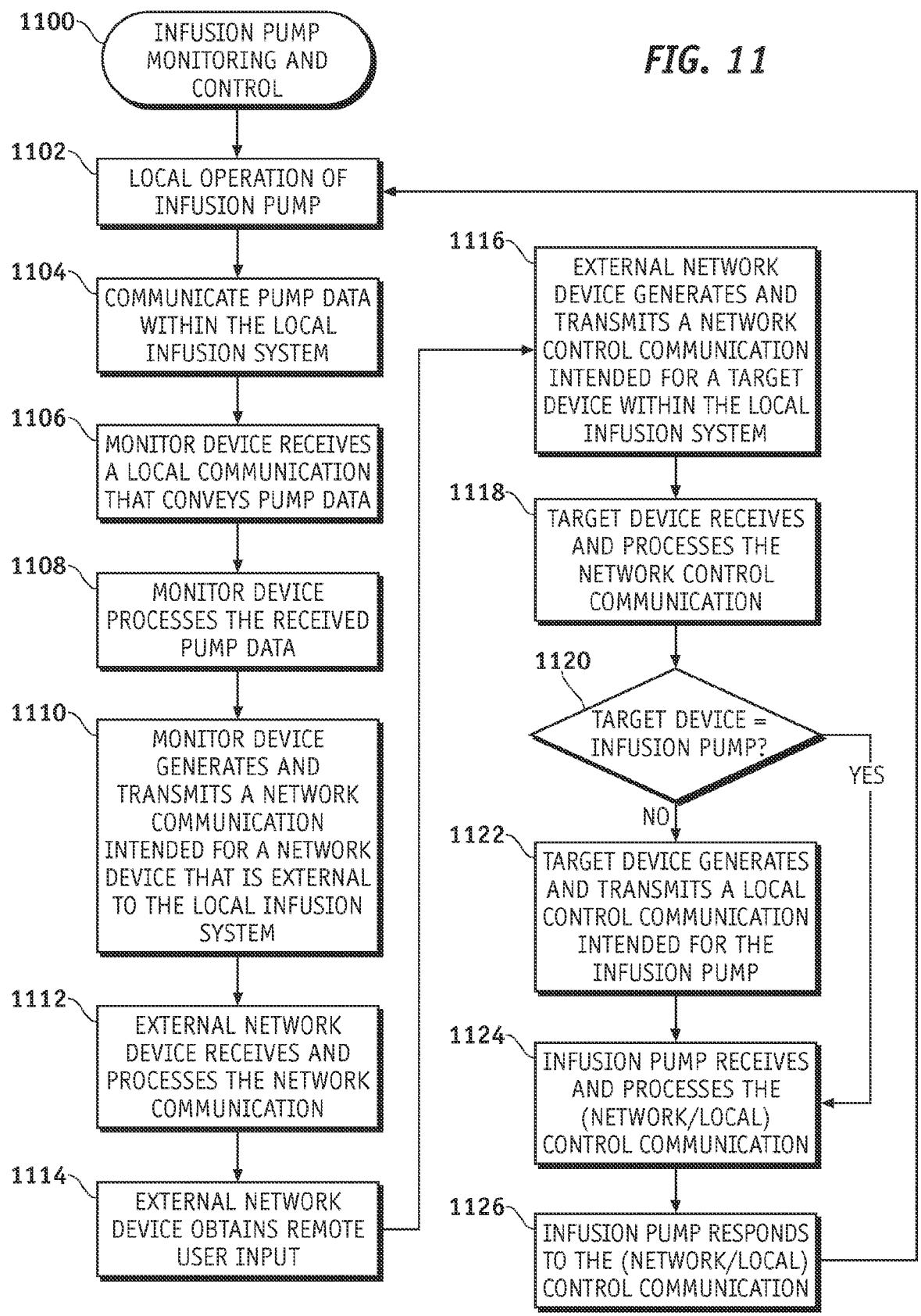
FIG. 11 is a flow chart that depicts an example network-based infusion pump monitoring and control process.

FIG. 11 is a flow chart that depicts an example network-based infusion pump monitoring and control process 1100. Process 1100 represents one example technique for operating a network-based infusion pump system. A system may be able to support any number of alternative techniques and methodologies, and the following description of process 1100 is not intended to limit the scope or application of the invention in any way. The various tasks performed in connection with process 1100 may be performed by software, hardware, firmware, or any combination. For illustrative purposes, the following description of process 1100 may refer to elements mentioned above in connection with FIGS. 1-8. In embodiments, portions of process 1100 may be performed by different elements of the described system, e.g., a local device, an infusion pump, a network device or any functional element or operating component. It should be appreciated that process 1100 may include any number of additional or alternative tasks, the tasks shown in FIG. 11 need not be performed in the illustrated order, and process 1100 may be incorporated into a more comprehensive procedure or process having additional functionality not described in detail here.

Infusion pump monitoring and control process 1100 is performed in conjunction with the normal local operation of an infusion pump (task 1102). Process 1100 preferably supports the communication of pump data within the local infusion system (task 1104), as described in detail above. In particular, task 1104 may correspond to the transmission of pump data from the infusion pump to a monitor device within the local infusion system, the transmission of pump data between local devices other than the infusion pump, or the like. In this example, a local monitor device receives a local communication that conveys pump data (task 1106). The local monitor device may be a bedside monitor, a hospital monitor, a handheld monitor/controller, or any suitably configured local device as described above. If necessary, the local monitor device processes the received pump data (task 1108) to determine how best to respond.

In this example, the local monitor device generates and transmits a network communication in response to the received pump data (task 1110). The network communication may be intended for any compatible network device that is external to the local infusion system. As described above, the network communication is preferably generated in accordance with a selected network data communication protocol that is also supported by the destination network device. Infusion pump monitoring and control process 1100 assumes that the external network device receives and processes (task 1112) the network communication in an appropriate manner. For example, the network device may generate an alert or an alarm that originated at the infusion pump.

In response to the network communication (e.g., an alert in this example), the network device may obtain a remote user input (task 1114). In this regard, a remote user input may correspond to manipulation of user interface features located at the network device. For example, the user of the network device may elect to disable the alert by engaging a "DISABLE" button on the network device. As another example, the user of the network device may elect to remotely administer a bolus by engaging an "ACTIVATE" button on the network device. In response to the remote user input, the network device may generate and transmit (task 1116) a suitably configured network control communication that is intended for a target device within the local infusion system. This control communication is formatted for compliance with a particular data communication protocol that is also supported by the target device. The target device may, but need not be, the same local device that transmitted (or originated) the local communication received during task 1106.

Infusion pump monitoring and control process 1100 assumes that the intended target device receives and processes (task 1118) the network control communication in an appropriate manner. Generally, the target device processes the received control communication to determine how best to respond. If the target device is the infusion pump, then process 1100 may proceed to a task 1124. If not, then process 1100 may proceed to a task 1122. During task 1122, the target device may generate and transmit a local control communication that is intended for the infusion pump. The target device generates and transmits the local control communication in accordance with a data communication protocol that is supported within the local infusion system. As an example, task 1122 can be performed when the target device is a local monitor device that locally communicates with the infusion device. Eventually, the infusion pump receives and processes (task 1124) the network or local control communication in an appropriate manner. In this regard, task 1124 is performed in response to the remote user input obtained at the network device during task 1114. In embodiments, the local infusion pump will respond to the control communication (task 1126) in a suitable manner. For example, the infusion pump may react in the following manner, without limitation: disable an alarm or an alert; update its software or firmware; modify its basal rate; activate its pump to administer a bolus; generate a local alert/alarm; perform a calibration routine; or the like.

In this example embodiment, infusion pump monitoring and control process 1100 enables continuous or periodic monitoring and control of the infusion pump. Accordingly, FIG. 11 depicts process 1100 as a loop, where task 1126 leads back to task 1102 for purposes of continued local operation of the infusion pump.

FIGS. 12-17 are screen shots that may be generated by monitor devices, controller devices, network devices, display devices, and/or other infusion system devices configured in accordance with example embodiments of the invention. For example, the content of these screen shots may be displayed by bedside monitor 200 (see FIG. 2), by hospital monitor 300 (see FIG. 3), by handheld monitor/controllers 400 and 410 (see FIG. 4), by any of the local devices within local infusion system 102 (see FIG. 1), and/or by any of the network devices 104 utilized by network-based infusion system 100 (see FIG. 1).

Figure 12:
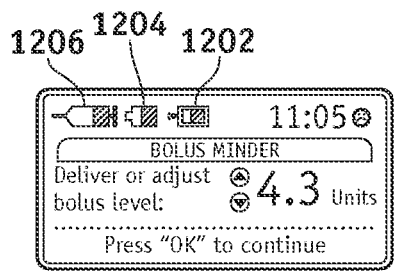
FIGS. 12-17 are screen shots that may be generated by monitor devices, controller devices, network devices, display devices, and/or other infusion system devices configured in accordance with example embodiments of the invention.

FIG. 12 is a screen shot that is suitable for use with a relatively small device, such as a handheld monitor, a personal digital assistant, a wireless phone, a key fob remote control, or the like. This screen shot includes a clock display, an RF quality indicator 1202, a battery indicator 1204, a fluid level indicator 1206 that represents the amount of fluid remaining in the infusion pump, and a recommended bolus (4.3 units in this example). This screen shot also includes the prompt: "Press 'OK' to Continue". The user can press "OK" to display other options, such as an activation request that controls the infusion pump to administer the recommended bolus.

Figure 13:
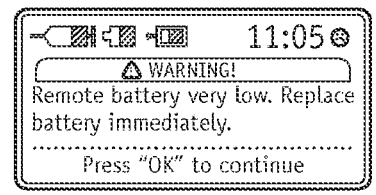

FIG. 13 is another screen shot that is suitable for use with a relatively small device. This screen shot includes a warning display, which may be accompanied by a suitably generated alert or alarm. Here, the warning includes text that indicates a low battery condition and a reminder to replace the battery. In example embodiments of the invention, such a warning may be associated with the battery in the device that actually displays the warning, or it may be associated with the battery in a remote device being monitored by the device that actually displays the warning. In this regard, this screen shot may be displayed at a network monitor device, where the low battery warning indicates that the battery in the local infusion pump device is low.

Figure 14:
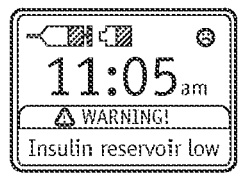

FIG. 14 is a screen shot that is suitable for use with a small form factor device, such as a remote control, a watch sized monitor, a portable display-only device, or the like. This screen shot includes a clock display, which is proportionately large for readability. This screen shot also includes a warning display, which may be accompanied by a suitably generated alert or alarm. Here, the warning includes text that indicates a low insulin reservoir condition for the monitored infusion pump. In example embodiments, this screen shot can be displayed on the infusion pump itself, on a remote device within the local infusion system, and/or on a network-based monitoring device.

Figure 15:
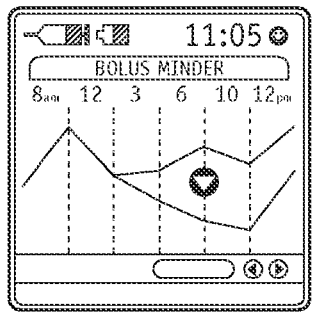
Figure 16:
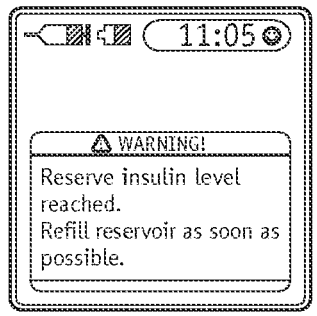
Figure 17:
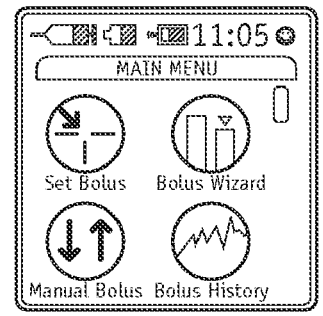

FIGS. 15-17 are various screen shots that are suitable for use with a relatively small device, such as a personal digital assistant, a wireless phone, or a pager device. The example screen shot of FIG. 15 includes historical BG data for the patient, rendered in a graph format, and a clock display. The screen shot of FIG. 16 includes a warning related to a low level in the insulin reservoir of the insulin pump, along with a clock display. The screen shot of FIG. 17 represents a "Main Menu" display for the device, where the menu includes a number of options for the user. For example, the device may display selectable menu icons, including, without limitation: a "Set Bolus" icon; a "Bolus Wizard" icon; a "Manual Bolus" icon; and a "Bolus History" icon. Selection of a given icon may cause the device to generate a new display screen that provides additional information or options related to the selected feature or function. For example, the "Set Bolus" icon enables the user to program the device for a specific bolus value or values that can be activated during use; the default values could be assigned to correspond to various meal carbohydrate values commonly consumed by the user, the "Bolus Wizard" icon launches a feature that enables the user to calculate a bolus of insulin that is appropriate for the patient's current condition, the "Manual Bolus" icon enables the user to deviate from the default bolus value(s), and the "Bolus History" icon launches a display (such as a graph, a chart, or a report) of past bolus deliveries by the infusion pump.

Again, the specific display formats, screen shot contents, display menu trees, and other display characteristics and features may vary depending upon the particular device configuration, whether the device is a network device or a local device within the infusion system, and/or whether the device is a wireless device. The example screen shots depicted in the various figures are not intended to limit or restrict the scope or application of any embodiment of the invention.

Figure 18:
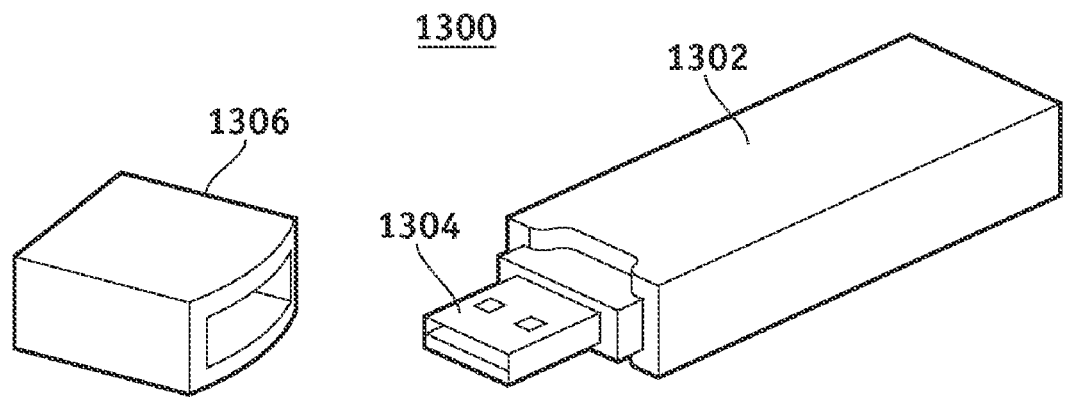
FIG. 18 is a perspective view of a data communication translation device configured in accordance with an example embodiment of the invention.

As mentioned above with regard to network-based infusion system 100 (see FIG. 1), a data communication translation device 113 may be utilized to facilitate communication between a wireless local device and a network device 104, such as a personal computer, a networked hospital computer, a caregiver office computer, or the like. FIG. 18 is a perspective view of a data communication translation device 1300 configured in accordance with one possible embodiment of the invention. In this embodiment, translation device 1300 is a relatively small and portable device that provides wireless bridge and memory storage functionality. Translation device 1300 may be conveniently sized such that it can be easily carried by a patient or a caregiver. In certain embodiments, translation device 1300 is small enough to be carried in a pocket.

Translation device 1300 includes a housing 1302 that encloses a number of functional components that are described in more detail below. This example embodiment includes a universal serial bus ("USB") connector 1304 that serves as a network interface port for translation device 1300. The network interface port can alternately be a IEEE 1394 port, a serial port, a parallel port, or the like. USB connector 1304 is configured for physical and electrical compliance with known USB specifications; such specifications will not be described in detail herein. Alternate embodiments may utilize different network interface configurations and, therefore, different network interface connectors, ports, couplers, or the like. USB connector 1304 is merely one suitable implementation of such a network interface, and embodiments of the invention are not limited to USB deployments.

Translation device 1300 may also include a removable cover 1306 that protects USB connector 1304 when translation device 1300 is not connected to a network device. Cover 1306 may be designed to snap onto USB connector 1304 and/or housing 1302 in a manner that allows the user to remove and replace cover 1306 by hand.

Figure 19:
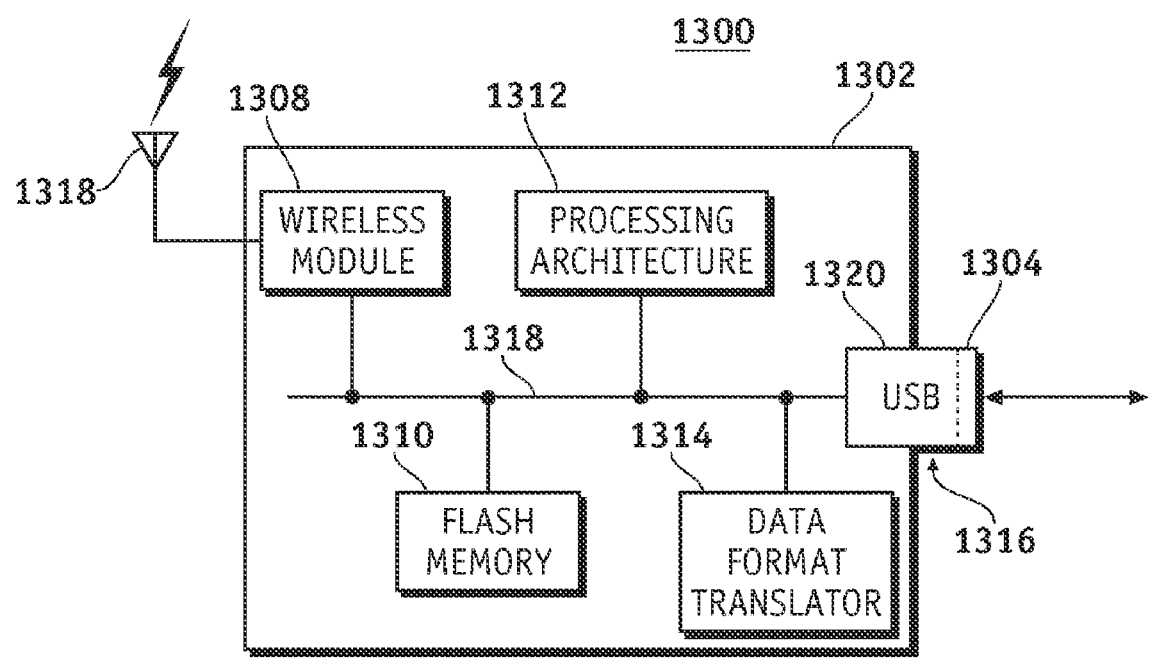
FIG. 19 is a schematic representation of a data communication translation device configured in accordance with an example embodiment of the invention.

FIG. 19 is a schematic representation of one example embodiment of translation device 1300. In this example, translation device 1300 generally includes housing 1302, a network interface port (e.g., USB connector 1304), a wireless communication module 1308, a memory element 1310, a processing architecture 1312, a data format translator 1314, and a network interface 1316 (e.g., a USB interface). The elements of translation device 1300 may be coupled together via a bus 1318 or any suitable interconnection architecture. In example embodiments, housing 1302 encloses wireless communication module 1308, memory element 1310, processing architecture 1312, and data format translator 1314. Depending upon the particular implementation, housing 1302 may also enclose at least a portion of network interface 1316.

Processing architecture 1312 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor may be realized as a microprocessor, a controller, a microcontroller, or a state machine. Moreover, a processor may be implemented as a combination of computing devices, e.g., a combination of a digital signal processor and a microprocessor, a plurality of microprocessors, one or more microprocessors in conjunction with a digital signal processor core, or any other such configuration. In an example embodiment of translation device 1300, data format translator 1314 may be implemented in processing architecture 1312 (even though FIG. 19 depicts the two as separate logical elements).

In practice, processing architecture 1312 is configured to support the various tasks, functions, and operations of translation device 1300. For example, processing architecture 1312 may be suitably configured to interpret and process incoming information, data, and content that is conveyed in local communications received from a transmitting device within the local infusion system. Likewise, processing architecture 1312 may be suitably configured to interpret and process incoming information, data, and content that is conveyed in network communications received from a network device external to the local infusion system. Processing architecture 1312 may also be configured to manage storage and retrieval of data in memory element 1310. Moreover, processing architecture 1312 may be configured to process data in response to instructions received from a network device via network interface 1316 and/or in response to instructions received from a local device via wireless communication module 1308.

In one embodiment, memory element 1310 can be a powered memory arrangement that utilizes a backup battery to maintain its storage ability. In the example embodiment, memory element 1310 is realized as nonvolatile flash memory having a suitable amount of storage capacity. The design and configuration of flash memory, its selection circuitry, and its program/erase control circuitry are generally known, and such conventional aspects of memory element 1310 will not be described in detail here. In alternate embodiments, memory element 1310 may utilize EEPROM memory, random access memory, registers, a small scale hard disk, a removable media, or the like. In this regard, memory element 1310 can be coupled to processing architecture 1312 such that processing architecture 1312 can read information from, and write information to, memory element 1310. In the alternative, memory element 1312 and processing architecture 1312 may be realized as an integrated unit. As an example, processing architecture 1312 and memory element 1310 may reside in an ASIC. As described in more detail below, memory element 1310 can be utilized to store data conveyed in wireless signals received from a local device within an infusion system. In addition, memory element 1310 can be utilized to store data conveyed in network communication signals received from a network device external to the infusion system. Such data may include local device status data, physiologic data of the user, sensor data, alerts/alarms, control data from the network device, operating instructions for translation device 1300, any of the local data types or content described herein, and/or any of the network data types or content described herein.

Wireless communication module 1308 is suitably configured to support wireless data communication with a device within an infusion system, e.g., any of the local devices mentioned in the above description of infusion system 100 (see FIG. 1). For example, the local device may be an infusion pump or a monitor device for an infusion pump. Depending upon the particular implementation, wireless communication module 1308 may be configured to support unidirectional communication from local devices, or bidirectional communication between translation device 1300 and local devices. Thus, wireless communication module 1308 may be configured to receive local communication signals from a transmitting device within the local infusion system, and/or to transmit local communication signals to a receiving device within the local infusion system.

Wireless communication module 1308 may include or be realized as a radio module that supports one or more wireless data communication protocols and one or more wireless data transmission schemes. In an embodiment, wireless communication module 1308 may include or be realized as hardware, software, and/or firmware, such as an RF front end, a suitably configured radio module (which may be a stand alone module or integrated with other or all functions of translation device 1300), a wireless transmitter, a wireless receiver, a wireless transceiver, an infrared sensor, an electromagnetic transducer, or the like. In this example, translation device 1300 includes an antenna 1318 coupled to wireless communication module 1308. Antenna 1318, which may be located inside or outside of housing 1302 (or partially inside and partially outside of housing 1302), is appropriately configured in accordance with the particular design of wireless communication module 1308.

For wireless transmissions of local communications, wireless communication module 1308 supports one or more wireless data communication protocols that are also supported by the local device(s) communicating with translation device 1300. Any number of suitable wireless data communication protocols, techniques, or methodologies may be supported by wireless communication module 1308 and translation device 1300, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB.

Network interface 1316 is generally configured to support transmission of network communications between translation device 1300 and one or more network devices. Network interface 1316 may include interface logic 1320 and network interface port 1304. Interface logic 1320 may be implemented in processing architecture 1312 (even though FIG. 19 depicts the two as separate logical elements). In this example embodiment, network interface 1316 is a USB interface, interface logic 1320 is compatible with USB specifications and requirements, and network interface port 1304 is a USB port or connector. As mentioned above, however, alternate embodiments may utilize different network interface configurations (for example, IEEE 1394) and, therefore, different network interface connectors, ports, couplers, or the like.

Network interface 1316 is suitably configured to support data communication with a device external to the infusion system, e.g., any of the network devices 104 mentioned in the above description of infusion system 100 (see FIG. 1). For example, the network device may be a personal computer having a suitable host application that can be manipulated to manage communication with translation device 1300. The personal computer may be owned by the patient, located in a caregiver facility, located in a hospital, located in a device manufacturer facility, or elsewhere. In example embodiments, the host application may be realized as software that is designed to provide monitoring, diagnostic services, patient data analysis, medical device programming, and/or other functions associated with one or more devices within the local infusion system. Depending upon the particular implementation, network interface 1316 may be configured to support unidirectional communication from translation device 1300, or bidirectional communication between translation device 1300 and network devices. Thus, network interface 1316 may be configured to receive network communication signals from a transmitting network device, and/or to transmit network communication signals to a receiving network device.

For transmission of network communication signals over a cable, a wired connection, a direct connection, or other physical link, network interface 1316 supports one or more wired/cabled data communication protocols that are also supported by the network device(s) communicating with translation device 1300. Any number of suitable data communication protocols, techniques, or methodologies may be supported by network interface 1316 and translation device 1300, including, without limitation: Ethernet; home network communication protocols; USB; IEEE 1394 (Firewire); hospital network communication protocols; and proprietary data communication protocols.

For wireless transmission of network communication signals, network interface 1316 supports one or more wireless data communication protocols that are also supported by the network device(s) communicating with translation device 1300. Any number of suitable wireless data communication protocols, techniques, or methodologies may be supported by network interface 1316 and translation device 1300, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB.

In connection with wireless data transmissions, translation device 1300 may be configured to perform dynamic frequency hopping to optimize its operation, to conserve battery life for battery-powered wireless devices, and/or to provide flexibility in the complexity of the devices with which it communicates. For example, wireless communication module 1308 may be designed to dynamically accommodate 5-channel (low power) devices and 50-channel (high power) devices. In this context, translation device 1300 may utilize a low power mode to conserve battery power when a high quality wireless link has been established. On the other hand, translation device 1300 may switch to a high power mode in response to increased packet loss, increased collision, or a generally poor quality of service.

In connection with wireless data transmissions, translation device 1300 may also be configured to support a retry periodicity for synchronous links having a designated transmission periodicity. For example, during normal operation, a synchronous wireless link may communicate one packet per minute. Translation device 1300 can be configured to initiate a retry procedure in response to a missed packet. In this regard, translation device 1300 can support retry transmissions (i.e., retransmission of the missed packet) that occur at a higher rate than the normal operating mode. For example, retry packet transmissions may occur every 20 seconds rather than once a minute. In practice, translation device 1300 and the wireless device may adapt their frequency hopping scheme to accommodate the retry packets, and resume their normal frequency hopping scheme thereafter.

Data format translator 1314, which may be realized as hardware, software, firmware, or any combination thereof, is suitably configured to reformat data between wireless communication module 1308 and network interface 1316. Depending upon the particular implementation, such reformatting may occur for data received via wireless communication module 1308, for data received via network interface 1316, or both. For example, it may be desirable for translation device 1300 to receive a wireless communication signal at wireless communication module 1308, extract data from the wireless communication signal, and process the extracted data in an appropriate manner such that the extracted data can be conveyed in a network communication signal to be provided by network interface 1316. Likewise, it may be desirable for translation device 1300 to receive a network communication signal at network interface 1316, extract data from the network communication signal, and process the extracted data in an appropriate manner such that the extracted data can be conveyed in a wireless communication signal to be provided by wireless communication module 1308.

Translation device 1300 may be configured to encrypt data between wireless communication module 1308 and network interface 1316. Encrypting data may be desirable for ensure that confidential or sensitive information remains protected. In this example, data format translator 1314 may be configured to perform data encryption using one or more known or proprietary encryption schemes. Alternatively, translation device 1300 may include a separate encryption engine or module that performs the data encryption. Depending upon the specific implementation, data encryption may be applied to the extracted data (or any portion thereof), to the sensitive/confidential data (or any portion thereof), and/or to the entire communication signal (or any portion thereof).

Translation device 1300 provides a wireless bridge between a local device and a network device, and translation device 1300 can support a range of data transmission and data storage features. In this regard, FIG. 20 is a flow chart that depicts an example data storage and translation process 1400 that may be supported by translation device 1300. The various tasks performed in connection with process 1400 may be performed by software, hardware, firmware, or any combination. For illustrative purposes, the following description of process 1400 may refer to elements mentioned above in connection with FIGS. 18 and 19. In practice, portions of process 1400 may be performed by different elements of the described system, e.g., wireless communication module 1308, memory element 1310, processing architecture 1312, or network interface 1316. It should be appreciated that process 1400 may include any number of additional or alternative tasks, the tasks shown in FIG. 20 need not be performed in the illustrated order, and process 1400 may be incorporated into a more comprehensive procedure or process having additional functionality not described in detail here.

Data storage and translation process 1400 may begin when the translation device is attached to a network device via the network interface of the translation device (task 1402). In this example, task 1402 is associated with the coupling of a USB-compatible translation device to a personal computer via the USB interface of the translation device. In response to this attachment, process 1400 powers the translation device and initializes the wireless communication module (task 1404). In accordance with conventional methodologies, the USB interface provides operating power from the computer to the translation device, and such operating power may be utilized to energize the wireless communication module and other functional elements of the translation device. In this example, the computer detects the mounting of the translation device and responds by automatically launching its host application (task 1406). Alternatively, the computer may prompt the user to manually launch the host application.

The translation device may be configured to support an auto-detect or standby mode, during which the translation device "listens" for compatible local devices that come within wireless transmission range. Such an auto device detection mode may be desirable to enable the system to accommodate intermittent or unreliable links by delaying wireless transmission of data until a link of sufficient strength is established. Such an auto device detection mode may also be desirable in a caregiver office environment to enable the system to download data (automatically or upon patient approval) whenever a patient enters the waiting room. Alternatively, the auto device detection mode may also be desirable in a user's home or other such environment to enable the system to automatically, or upon patient approval, download data directly into a central depository or into a temporary holding area, such as a PC, and then transfer the data to a central depository, such as a web server, or a hospital database. If the auto device detection mode is active (query task 1408), then the translation device may check to determine whether a local device has been detected (query task 1410). If the translation device detects a local device within range, then data storage and translation process 1400 may continue as described below. Otherwise, the translation device may idle until it detects a local device within range, or process 1400 may be re-entered at query task 1408. If the auto device detection mode is inactive, or if the translation device does not support the auto device detection mode, then query task 1408 may lead to a query task 1412.

Data storage and translation process 1400 may perform query task 1412 to determine whether a user of the host application has assumed control over the translation device. If host control is not initiated, then process 1400 may be re-entered at query task 1408. Alternatively, if host control is not initiated, then process 1400 may idle until host control occurs. If, however, host control is initiated, then process 1400 may continue as described below.

Figure 20A:
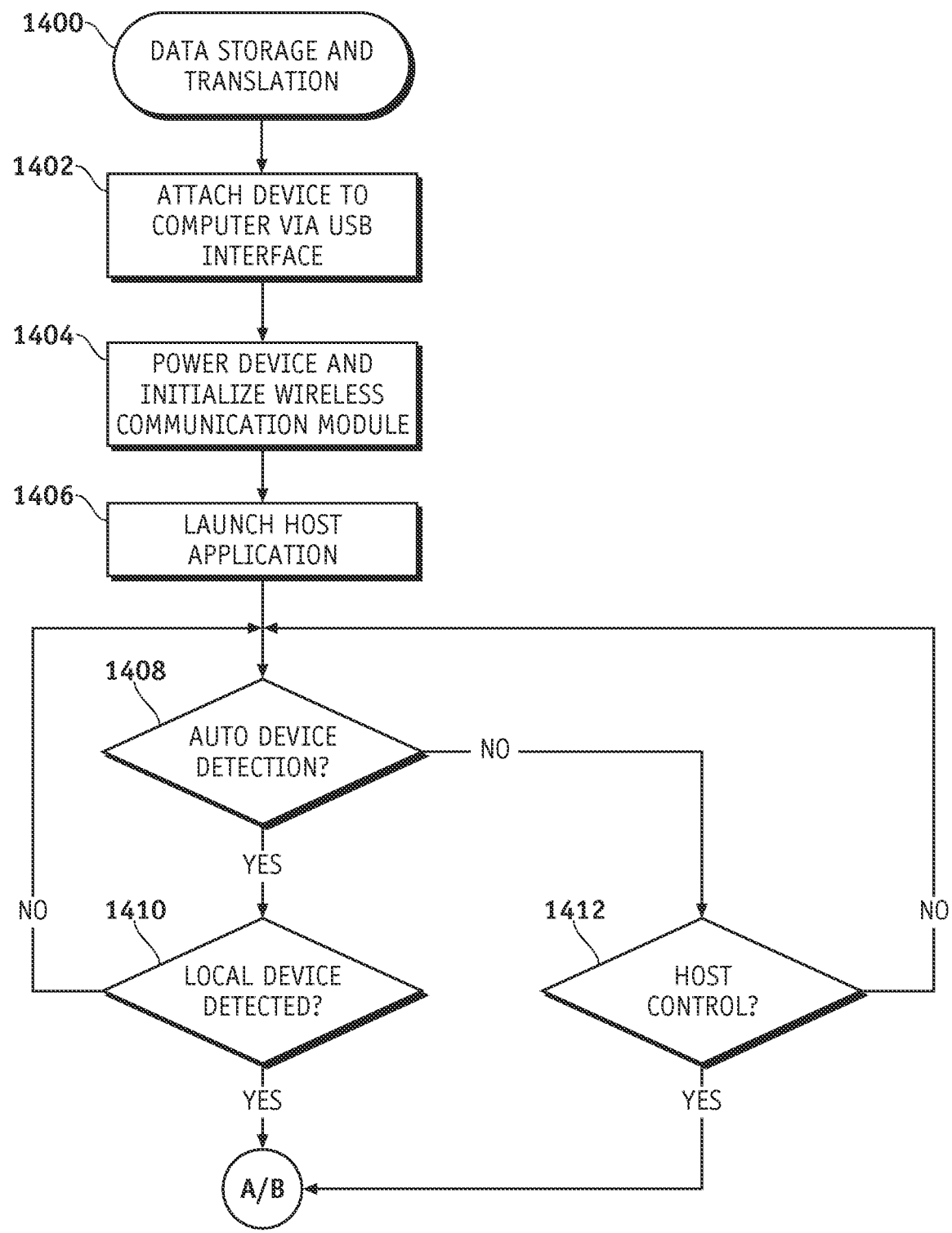
FIG. 20 is a flow chart that depicts an example data storage and translation process.
Figure 20B:
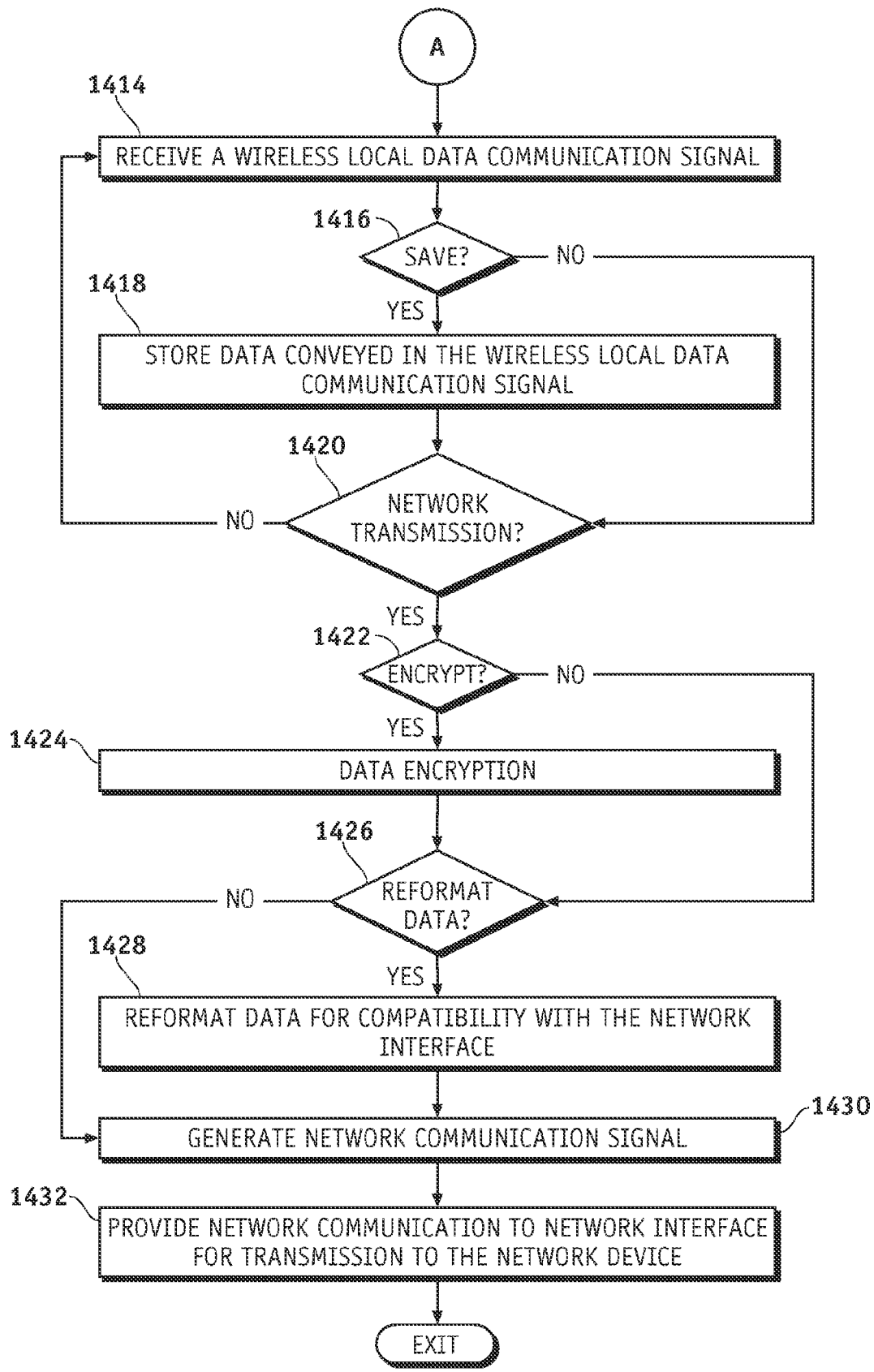
Figure 20C:
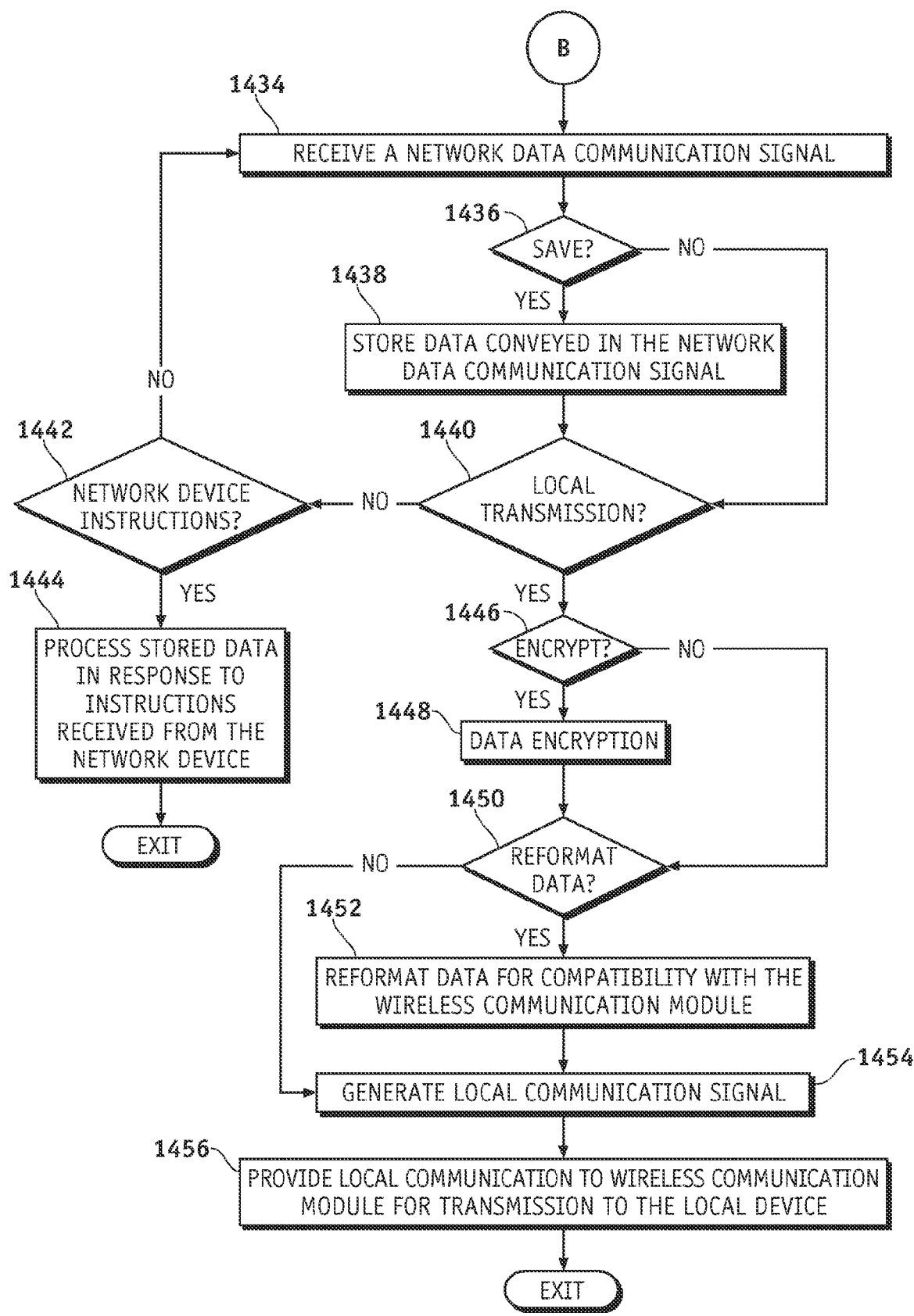

Depending upon the implementation and the application, the translation device may receive and process data from a wireless local device and/or receive and process data from a network device. For ease of description, data storage and translation process 1400 is arbitrarily and artificially separated into sub-process A (relating to the handling of incoming wireless communication signals) and sub-process B (relating to the handling of incoming network communication signals). An embodiment of the translation device may be suitably configured to carry out both sub-processes concurrently or in a synchronous manner that avoids transmit/receive clashes. Either or both of these sub-processes may follow query task 1410 or query task 1412, as indicated in FIG. 20A.

Referring to sub-process A (see FIG. 20B), the translation device may receive a wireless local data communication signal from a local device within the infusion system (task 1414). In one example embodiment, during an initial handshaking or packet exchange routine, the device initiating contact indicates whether the transmission is a one-time packet (which could be sent as often as required) or a synchronous-link packet that requires time synchronization of packets sent and received between the two communicating devices. If data conveyed in the received wireless local data communication signal is to be saved (query task 1416), then the translation device may extract and store the data in its resident memory element (task 1418). Following the data storage of task 1418, data storage and translation process 1400 may proceed to a query task 1420. If data conveyed in the wireless local data communication signal is not to be saved, then process 1400 may bypass task 1418 and proceed to query task 1420.

Query task 1420 may determine whether the translation device is to perform network transmission of data. The translation device may be suitably configured to support network transmission of data stored in the memory element and/or network transmission of data that need not be stored in the memory element. For example, the translation device may be configured to process data stored in the memory element for transmission to a network device that is external to the infusion system. In this example, such network transmission corresponds to transmission of data from the translation device to the host computer via the USB interface. If network transmission has not been initiated, then data storage and translation process 1400 may be re-entered at task 1414 to allow the translation device to continue receiving wireless communication signals. If, however, network transmission has been initiated, then process 1400 may proceed to a query task 1422.

Query task 1422 determines whether the translation device is to perform data encryption. The translation device may be suitably configured to encrypt data conveyed in wireless local data communication signals, to encrypt data conveyed in network communication signals, and/or to encrypt data stored in the memory element. For example, the translation device may encrypt data stored in the memory element for encrypted transmission to the network device, which is compatibly configured to decrypt the data. If encryption is to be performed, then data storage and translation process 1400 performs data encryption (task 1424) using any suitable data encryption technique. After process 1400 performs encryption, it may lead to a query task 1426. If the data will not be encrypted, then process 1400 may bypass task 1424 and proceed to query task 1426.

Query task 1426 determines whether the translation device is to reformat data for transmission to the network device. For example, data storage and translation process 1400 may reformat data conveyed in the wireless local data communication signal for compatibility with the network interface (task 1428). Process 1400 may additionally (or alternatively) reformat data that has been stored in the memory element. Such reformatting may be desirable to enable the network interface to provide network communications to the network device, where the network communications convey the reformatted data. After reformatting data in a desired manner, the translation device can generate a network communication signal (task 1430). Task 1430 may also be performed if query task 1426 determines that reformatting is unnecessary or undesired. In this example, the network communication signal includes data that was conveyed in the wireless local data communication signal and/or data retrieved from the memory element.

Eventually, data storage and translation process 1400 provides the network communication signal (generated during task 1430) to the network interface for transmission to the network device (task 1432). In the example embodiment, task 1432 results in the transmission of data to the host computer via the USB interface. Following task 1432, process 1400 may exit or it may be re-entered at a designated point, such as query task 1408.

Referring to sub-process B (see FIG. 20C), the translation device may receive a network data communication signal from a network device that is external to the infusion system (task 1434). In one example embodiment, during an initial handshaking or packet exchange routine, the device initiating contact indicates whether the transmission is a one-time packet (which could be sent as often as required) or a synchronous-link packet that requires time synchronization of packets sent and received between the two communicating devices. If data conveyed in the network data communication signal is to be saved (query task 1436), then the translation device may extract and store the data in its resident memory element (task 1438). Thereafter, data storage and translation process 1400 may proceed to a query task 1440. If data conveyed in the network data communication signal is not to be saved, then process 1400 may bypass task 1438 and proceed to query task 1440.

Query task 1440 may determine whether the translation device is to perform local transmission of data. The translation device may be suitably configured to support local transmission of data stored in the memory element and/or local transmission of data that need not be stored in the memory element. For example, the translation device may be configured to process data stored in the memory element for transmission to a local device within the infusion system. In this example, such local transmission corresponds to transmission of data from the translation device to a local device via the wireless communication module. If local transmission has not been initiated, then data storage and translation process 1400 may check whether the received network data communication signal conveys operating or control instructions from the network device (query task 1442). If so, then the translation device may process data stored in the memory element in response to such instructions (task 1444). These instructions may include or indicate a request for certain data stored at the translation device, a request for the translation device to obtain data from a local device, programming or configuration data for the translation device and/or a local device, or the like. Following task 1444, process 1400 may exit or it may be re-entered at a designated point, such as task 1434 or query task 1408.

If query task 1440 determines that local transmission has been initiated, then data storage and translation process 1400 may proceed to a query task 1446. Query task 1446 determines whether the translation device is to perform data encryption as described previously. For example, the translation device may encrypt data conveyed in the received network data communication signal and/or data stored in the memory element for encrypted transmission to the wireless local device, which is compatibly configured to decrypt the data. If encryption is to be performed, then process 1400 performs data encryption (task 1448) using any suitable data encryption technique. After process 1400 encrypts the data, it may proceed to a query task 1450. If the data will not be encrypted, then process 1400 may bypass task 1448 and proceed to query task 1450.

Query task 1450 determines whether the translation device is to reformat data for transmission to the wireless local device. For example, data storage and translation process 1400 may reformat data conveyed in the network data communication signal for compatibility with the wireless data communication module (task 1452). Process 1400 may additionally (or alternatively) reformat data that has been stored in the memory element. Such reformatting may be desirable to enable the wireless communication module to provide local wireless communication signals to the local device(s), where the wireless signals convey the reformatted data. After reformatting data in a desired manner, the translation device can generate a local communication signal (task 1454). Task 1454 may also be performed if query task 1450 determines that reformatting is unnecessary or undesired. In this example, the local communication signal is a wireless signal that includes data that was conveyed in the network data communication signal and/or data retrieved from the memory element.

Eventually, data storage and translation process 1400 provides the local communication signal (generated during task 1454) to the wireless communication module for transmission to the local device (task 1456). In the example embodiment, task 1456 results in the wireless transmission of data to a local device via the wireless communication module. Following task 1456, process 1400 may exit or it may be re-entered at a designated point, such as query task 1408.

Translation device 1300, data storage and translation process 1400, and other processes supported by translation device 1300 provide added flexibility and convenience for users of the infusion system. For example, translation device 1300 can support the downloading of history data from an infusion pump or an infusion pump monitor with automatic storage to its internal flash memory. Such downloading may be driven by the host application—the host computer can command translation device 1300 to download data to the flash memory—for retrieval and analysis at a later date by the patient's caregiver. Patient history data may be encrypted such that only an authorized caregiver computer system can access the history files. Alternatively, the history files could be read-only by the patient, with read/write access provided to the caregiver. In example embodiments, the host application may be configured to detect whether the patient or a caregiver is communicating with the local device via translation device 1300. Consequently, translation device 1300 may be configured to support patient-specific and/or caregiver-specific functions and operations if so desired.

Figure 21:
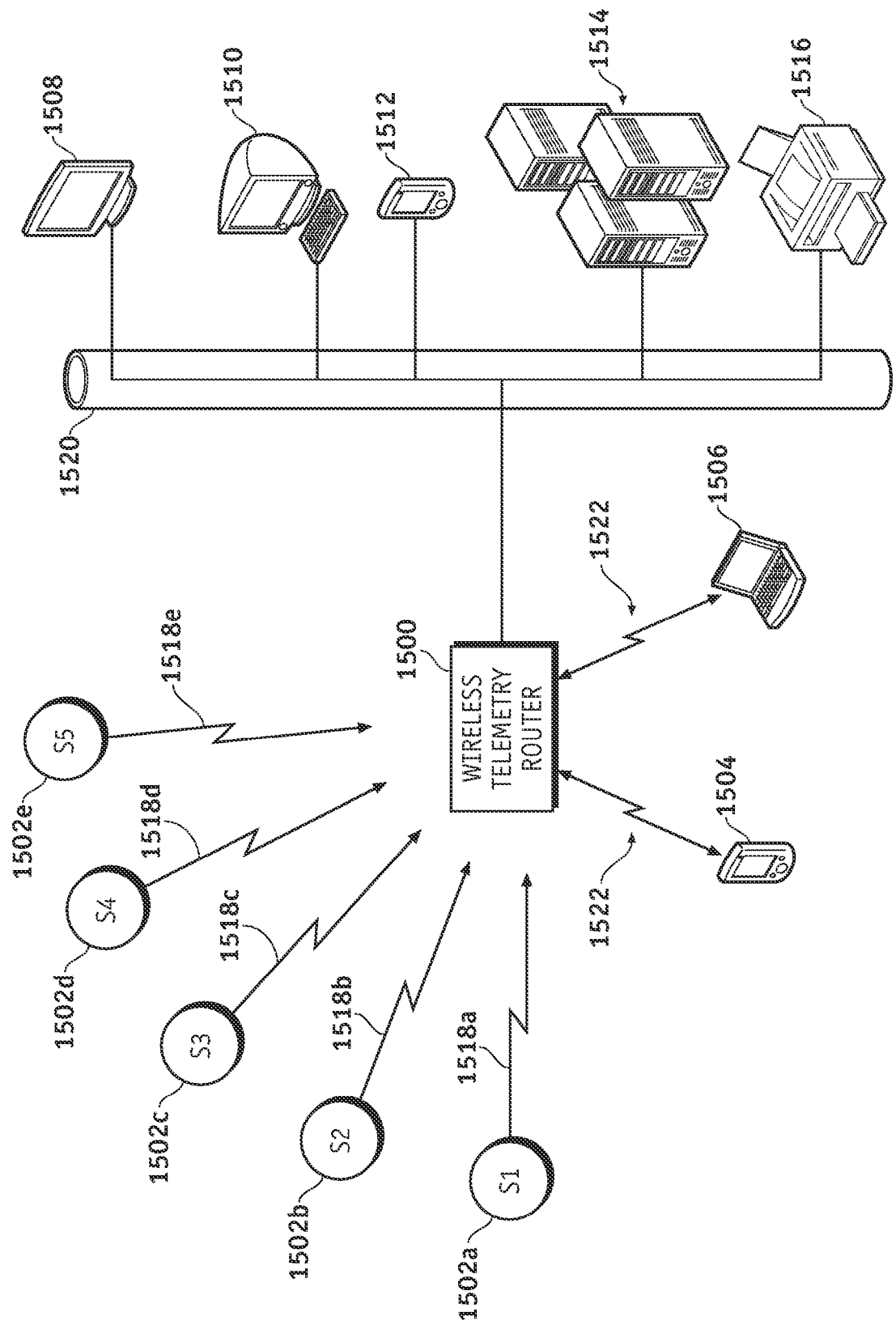
FIG. 21 is a schematic representation of an example network deployment of a wireless telemetry router configured in accordance with an example embodiment of the invention.

Depending upon the given deployment of an infusion system, it may be desirable to collect data from a plurality of local devices such that the collected data can be stored, processed, routed, or otherwise managed in an controlled manner. In this regard, FIG. 21 is a schematic representation of an example network deployment of a wireless telemetry router 1500 configured in accordance with an example embodiment of the invention. Wireless telemetry router 1500 may be deployed in a medical device system such as network-based infusion system 100 (see FIG. 1). Wireless telemetry router 1500 is suitably configured to communicate with a plurality of wireless devices within a local medical device system, such as a local infusion system. Wireless telemetry router 1500 is also configured to communicate with one or more network devices, which may be external to the local medical device system. For example, wireless telemetry router 1500 may communicate with network devices coupled to wireless telemetry router 1500 via an Ethernet connection and/or via wireless links.

The flexible nature of the example environment is depicted in FIG. 21, which depicts wireless telemetry router 1500 in communication with a variety of devices. In an example embodiment, wireless telemetry router 1500 may be suitably configured to communicate with one or more of the following devices, without limitation: a plurality of physiological characteristic sensor transmitters 1502, a wireless personal digital assistant 1504, a wireless laptop computer 1506, a network monitor 1508, a network computer 1510, a network personal digital assistant 1512, a network hospital management system 1514, and a network printer 1516. Wireless telemetry router 1500 may also be configured to support communication with the various local devices and network devices mentioned in the above description of infusion system 100.

Although FIG. 21 depicts five physiological characteristic sensor transmitters 1502, wireless telemetry router 1500 can support any number of sensor transmitters (limited only by practical operating restrictions such as bandwidth, available power, transmission range, etc.). Each physiological characteristic sensor transmitter 1502 is suitably configured to measure a physiologic characteristic of a patient. In the example infusion system described here, each sensor transmitter 1502 is a continuous glucose (e.g., blood glucose) sensor transmitter that measures the glucose level of a patient in real time. Each sensor transmitter 1502 may be realized in a form that is intended to be worn by the patient, attached to the patient's skin, implanted within the patient's body, or the like. Each sensor transmitter 1502 includes a wireless transmitter that facilitates transmission of physiologic sensor data of the user to wireless telemetry router 1500 and possibly other devices within the local infusion system.

Wireless telemetry router 1500 may be deployed in any environment where physiological characteristic sensor transmitters 1502 might come in range. Wireless telemetry router 1500 can support a system where a plurality of sensor transmitters 1502 are used by one person and/or a system that contemplates more than one person (each using only one sensor transmitter 1502). Moreover, wireless telemetry router 1500 can be suitably configured to support different types of sensor transmitters, and the example environment depicted in FIG. 21 need not be limited to an insulin infusion system or any specific type of medical device system. Example applications of wireless telemetry router 1500 include the following, without limitation: one patient having multiple sensor transmitters 1502, each being configured to provide data indicative of a different physiologic characteristic; a home deployment where more than one member of a family uses a sensor transmitter 1502; a school deployment where it may be desirable to monitor the physiologic data for any number of students; a hospital deployment where it may be desirable to monitor physiologic data for any number of patients; or a caregiver office environment where it may be desirable to identify specific sensor transmitters 1502 for purposes of patient identification and/or to obtain data from sensor transmitters 1502.

Physiological characteristic sensor transmitters 1502 and wireless telemetry router 1500 are suitably configured to support wireless data communication via respective wireless links 1518, which may be unidirectional (as shown) or bidirectional, depending upon the particular system and/or the specific type of sensor transmitters 1502. Accordingly, wireless telemetry router 1500 includes a suitably configured wireless communication module that is capable of supporting multiple sensor transmitters 1502.

Although not a requirement of the system, wireless links 1518 may be established using the same wireless data communication protocol and wireless data transmission scheme. Wireless telemetry router 1500 may utilize any number of suitable wireless data communication protocols, techniques, or methodologies for wireless links 1518, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In the example embodiment, wireless links 1518 are carried over the 900-930 MHz band that is reserved for industrial, scientific, and medical equipment use. As another example, wireless links 1518 in a hospital implementation may utilize the WMTS bands that are reserved for hospital applications. Packaging of sensor data, error detection, security, sensor transmitter identification, and other sensor data processing techniques may be governed by known or proprietary protocols.

Wireless telemetry router 1500 may be configured to communicate with network devices via Ethernet connectivity (or via any suitable data communication methodology). FIG. 21 depicts an Ethernet data communication architecture 1520 that links wireless telemetry router 1500 to network monitor 1508, network computer 1510, network personal digital assistant 1512, network hospital management system 1514, and network printer 1516. Of course, these example network devices are not exhaustive, and embodiments of the invention are not limited to these examples. A given link between wireless telemetry router 1500 and a network device may be unidirectional (in either direction) or bidirectional, depending upon the particular system and/or the specific type of network device. For example, the link from wireless telemetry router 1500 to network printer 1516 may be unidirectional, the link from wireless telemetry router 1500 to network monitor 1508 may be unidirectional, and other links may be bidirectional.

Wireless telemetry router 1500 may be configured to support wireless communication with compatible wireless devices, such as wireless personal digital assistant 1504 and wireless laptop computer 1506. Accordingly, wireless telemetry router 1500 includes a suitably configured wireless communication module, which may (but need not) be distinct from the wireless communication module that receives wireless links 1518. In this regard, FIG. 21 depicts wireless links 1522 between wireless telemetry router 1500 and these wireless devices. A given wireless link 1522 between wireless telemetry router and a wireless device may be unidirectional in either direction or bidirectional (as shown in FIG. 21), depending upon the particular system and/or the specific type of wireless device. In practice, wireless links 1522 enable wireless telemetry router 1500 to communicate directly with wireless devices while bypassing the network (i.e., without having to traverse Ethernet data communication architecture 1520).

Although not a requirement of the system, wireless links 1522 may be established using the same wireless data communication protocol and wireless data transmission scheme. In this example, wireless telemetry router 1500 utilizes one wireless data communication technique for wireless links 1522 and a different wireless data communication technique for wireless links 1518. Wireless telemetry router 1500 may utilize any number of suitable wireless data communication protocols, techniques, or methodologies for wireless links 1522, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Packaging of data, error detection, security, and other data processing techniques may be governed by known or proprietary protocols.

In one example embodiment, wireless telemetry router 1500 includes an HTML-based setup, management, and control interface that can be accessed via any authorized computer or device having HTML browser capabilities and connectivity to wireless telemetry router 1500. For example, an administrator may be able to access wireless telemetry router 1500 via the Internet and a conventional web browser application residing on wireless personal digital assistant 1504, wireless laptop computer 1506, network computer 1510, or network personal digital assistant 1512. The control interface may be provided as one or more HTML pages that reside in the firmware/software of wireless telemetry router 1500. The control interface can be accessed using an IP address and/or a network interface card that is unique to that particular wireless telemetry router 1500. Password and firewall protection may be implemented to provide protection against external misuse or data theft.

In connection with a setup procedure, wireless telemetry router 1500 may be provided with sensor identifiers for the respective physiological characteristic sensor transmitters 1502. The sensor identifiers may be, for example, the serial numbers of sensor transmitters 1502 or any information that uniquely distinguishes the different sensor transmitters 1502 within the operating environment. In example embodiments, wireless communication signals generated by an originating sensor transmitter 1502 conveys the corresponding sensor identifier. Wireless telemetry router 1500 can then process the sensor identifiers in a suitable manner. For example, wireless telemetry router 1500 may receive a wireless communication signal from an originating sensor transmitter 1502, obtain or extract the sensor identifier for that wireless communication signal, and process the sensor data conveyed in that wireless communication signal in a manner that is determined, governed, or dictated by the particular sensor identifier. This technique enables wireless telemetry router 1500 to identify the originating sensor transmitter 1502, the originating patient, the sensor transmitter type, or other pertinent information. Wireless telemetry router 1500 may then process, store, and/or route the sensor data in an appropriate manner. As another example, wireless telemetry router 1500 may receive a first wireless communication signal from a first sensor transmitter 1502a, receive a second wireless communication signal from a second sensor transmitter 1502b, obtain or extract the two respective sensor identifiers (which should be different), and process the sensor data conveyed in the two wireless communication signals in a synchronized manner that is determined, governed, or dictated by the sensor identifiers. This technique enables wireless telemetry router 1500 to prioritize the receipt, processing, storage, and/or transmission of sensor data depending upon the originating source.

In connection with a setup procedure, wireless telemetry router 1500 may be provided with network identifiers (e.g., IP addresses or network interface card identifiers) for the various destination network devices. Such network identifiers enable wireless telemetry router 1500 to determine how to process, handle, store, or route the received sensor data. In this regard, wireless telemetry router 1500 may, for example, maintain or access a lookup table (or any suitable memory or database structure) that contains the different sensor identifiers and a corresponding list of destination network identifiers for each sensor identifier. This lookup table may also include corresponding processing instructions for each sensor identifier.

Wireless telemetry router 1500 is generally configured to receive sensor data and route the sensor data to one or more destination network devices. In this example, wireless telemetry router 1500 receives a plurality of wireless communication signals from a plurality of physiological characteristic sensor transmitters 1502, where each wireless communication signal conveys sensor data generated by a respective sensor transmitter 1502. As mentioned above, each wireless communication signal may also convey a sensor identifier that uniquely identifies the originating sensor transmitter 1502. Wireless telemetry router 1500 can then process the received information in an appropriate manner, depending upon the particular application and the identity of the originating sensor transmitter 1502.

Wireless telemetry router 1500 may perform one or more operations on the received sensor data, including, without limitation: storing at least some of the sensor data (at wireless telemetry router 1500 itself or at a network device that is coupled to wireless telemetry router 1500); forward at least some of the sensor data to a destination network device; reformat data conveyed in the wireless communication signals for compatibility with a designated network data communication protocol; or process at least some of the sensor data. In example embodiments, wireless telemetry router 1500 may include some functionality and processing intelligence that might normally be found elsewhere in the system environment. For example, wireless telemetry router 1500 may be configured to receive uncalibrated physiologic characteristic data, such as an uncalibrated patient glucose level, and calibrate the data before routing it to the destination network device.

In connection with its routing function, wireless telemetry router 1500 may generate a network communication that complies with a specified network data communication protocol. The network communication conveys sensor data, which may include stored sensor data, real-time sensor data that is being immediately routed, or a combination thereof. Wireless telemetry router 1500 can then transmit the network communication to one or more network devices. Wireless telemetry router 1500 transmits the network communication in accordance with the selected network data communication protocol and in accordance with the selected data transmission technique. For example, wireless telemetry router 1500 may function as a translation device between data received on wireless links 1518 (using one protocol and transmission scheme combination) and data transmitted over Ethernet data communication architecture 1520 (using another protocol and transmission scheme combination). As another example, wireless telemetry router 1500 may function as a translation device between data received on wireless links 1518 (using one protocol and transmission scheme combination) and data transmitted over wireless links 1522 (using another protocol and transmission scheme combination).

Wireless telemetry router 1500 may also be configured to generate warning, error, alarm, and alert information ("diagnostic information"), which may be routed using the techniques described above. The diagnostic information may be displayed or rendered at wireless telemetry router 1500 itself and/or routed for display or rendering at a network device. The diagnostic information may include, without limitation: information related to the operation or status of wireless telemetry router 1500; information related to the operation or status of physiological characteristic sensor transmitters 1502; information related to the operation or status of a network device; or any of the notifications, alerts, alarms, or status reports described in more detail above.

Wireless Medical Device Network Protocols and Features

Medical devices, including any of the devices described above, may be suitably configured to support wireless data communication within a network environment. Unless otherwise specified, the following examples assume that wireless data is transferred between the medical devices using suitably formatted data packets, and that communication between the medical devices is bi-directional (half-duplex or full-duplex). Generally, a network of medical devices includes any number (N) of devices, and a subnetwork of medical devices within the network includes any subset of the N devices. A given device within the network may be common to more than one subnetwork, i.e., subnetworks need not be mutually exclusive.

Figure 22:
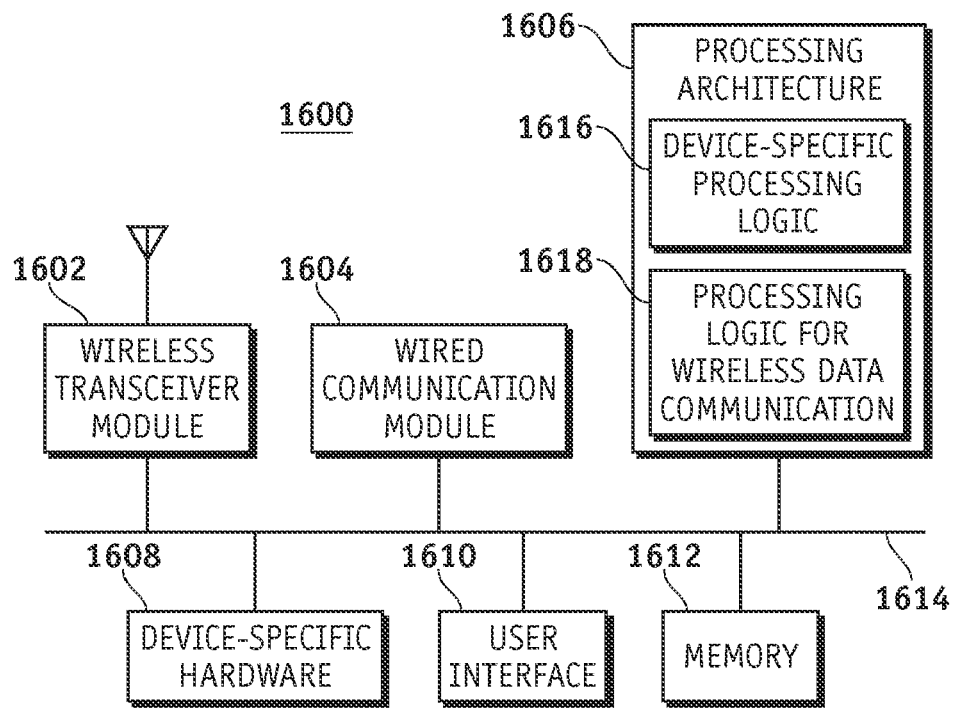
FIG. 22 is a schematic and generalized representation of a medical device having wireless data communication and wireless networking capabilities.

As described above, a fluid infusion system is one example of a medical device network having wireless medical devices, where a network device may be, without limitation: an infusion pump; a physiological characteristic sensor transmitter; a portable display device; a remote controller; a physiological characteristic meter; a controller; a monitor device; a data translation device; a wireless telemetry router; or the like. FIG. 22 is a schematic and generalized representation of a medical device 1600 having wireless data communication and wireless networking capabilities. Device 1600 may represent any of the wireless medical devices described above. Accordingly, device 1600 may include a number of additional and/or alternative components that are specific to its particular application and functionality. Generally, device 1600 may include a wireless transceiver module 1602, a wired communication module 1604, a processing architecture 1606, device-specific hardware 1608, a user interface 1610, and an appropriate amount of memory 1612. The elements of device 1600 may be coupled together via a bus 1614 or any suitable interconnection architecture.

Figure 23:
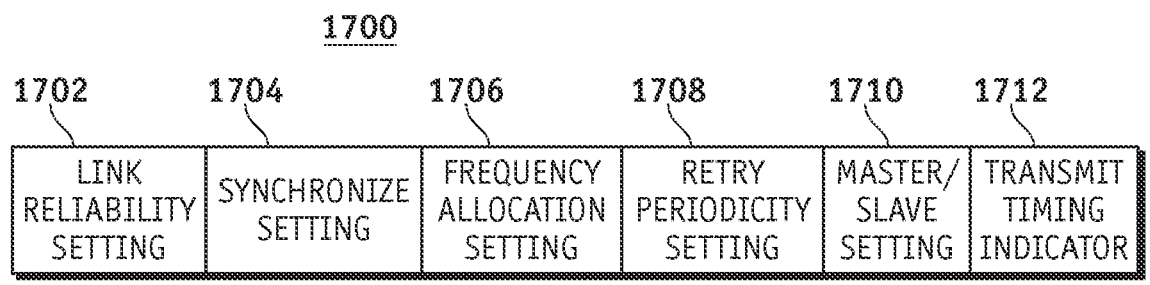
FIG. 23 is a diagram of a portion of a data packet that contains data fields representing different dynamic link parameters corresponding to supported wireless data communication modes.

Wireless transceiver module 1602 is suitably configured to transmit and receive wireless data communication signals using appropriate wireless data communication links. The wireless signals include data fields that include data representing the desired information to be transferred within the medical device network. In certain embodiments, the wireless signals convey data packets that include the desired data fields. In this regard, FIG. 23 is a diagram of a portion of a data packet 1700 that contains data fields representing different dynamic link parameters corresponding to supported wireless data communication modes. An embodiment of medical device 1600 may be configured to process dynamic link parameters related to: a link reliability setting 1702; a synchronize setting 1704; a frequency allocation setting 1706; a retry periodicity setting 1708; a master/slave setting 1710; and/or a transmit timing indicator 1712. Any of these link parameters can be dynamically updated during a wireless data communication session. Moreover, data packet 1700 need not convey all of these dynamic link parameters; FIG. 23 depicts a full-featured version for ease of description. Each of these link parameters is described in more detail below.

Wireless transceiver module 1602 can transmit (and/or receive) wireless signals over wireless communication channels established between medical device 1600 and other compatible medical devices in the medical device network. Wireless transceiver module 1602 may include a wireless receiver module and a wireless transmitter module integrated together as a wireless (RF) radio module. Alternatively, medical device 1600 may utilize distinct wireless receiver and wireless transmitter modules. Wireless transceiver module 1602 may be configured as described above for wireless module 1308 (see FIG. 19).

Medical device 1600 may also be capable of supporting data communication via a wired or cabled link using wired communication module 1604. Accordingly, wired communication module 1604 may utilize hardware, software, firmware, processing logic, or any combination thereof, to provide the desired wired interface for medical device 1600. Wired communication module 1604 may be suitably configured to support any of the wired data communication protocols described above (see, for example, the description of monitor 500).

Processing architecture 1606 is generally configured as described above (see, for example, the description of processing architecture 514). For this generalized medical device 1600, processing architecture 1606 may include device-specific processing logic 1616 and processing logic 1618 for the particular wireless data communication modes supported by device 1600. The device-specific processing logic 1616 represents the processing capabilities that relate to the operation and functionality of device 1600. For example, if device 1600 is an infusion pump, then device-specific processing logic 1616 will include instructions related to pump operations. On the other hand, if device 1600 is a patient monitor, then device-specific processing logic 1616 will include instructions related to monitor operations. Processing logic 1618 represents various instructions, control logic, and processing capabilities related to the different wireless data communication protocols, wireless data transmission protocols, and dynamic wireless link parameters described here. In practice, some of the processing logic 1618 may (but need not) also be device-specific.

Device-specific hardware 1608 represents hardware and/or firmware that relate to the particular operation and functionality of medical device 1600. For example, if device 1600 is an infusion pump, then device-specific hardware 1608 will include the pump mechanism. On the other hand, if device 1600 is a BG meter, then device-specific hardware 1608 may include a receptacle for a blood sample strip or stick.

User interface 1610 may include any number of features that allow user interaction with medical device 1600. User interface 1610 may include any of the user interface elements described previously (see, for example, the description of user interface 208).

Memory 1612 may be realized as described above for memory 516. Memory 1612 can be coupled to processing architecture 1606 such that processing architecture 1606 can read information from, and write information to, memory 1612. In the alternative, memory 1612 may be integral to processing architecture 1606. As an example, processing architecture 1606 and memory 1612 may reside in an ASIC. Memory 1612 is generally configured to store device-specific data and any data necessary to support the different wireless data communication modes described in more detail below.

Medical device 1600 (and/or a network of medical devices 1600) is suitably configured to perform the various processes described here. A given process may be performed by software, hardware, firmware, or any combination. In embodiments, portions of a given process may be performed by different elements of the described system or device. Moreover, it should be appreciated that a described process may include any number of additional or alternative tasks, the tasks shown in the figures need not be performed in the illustrated order, and a described process may be incorporated into a more comprehensive procedure or process having additional functionality not described in detail here.

Figure 24:
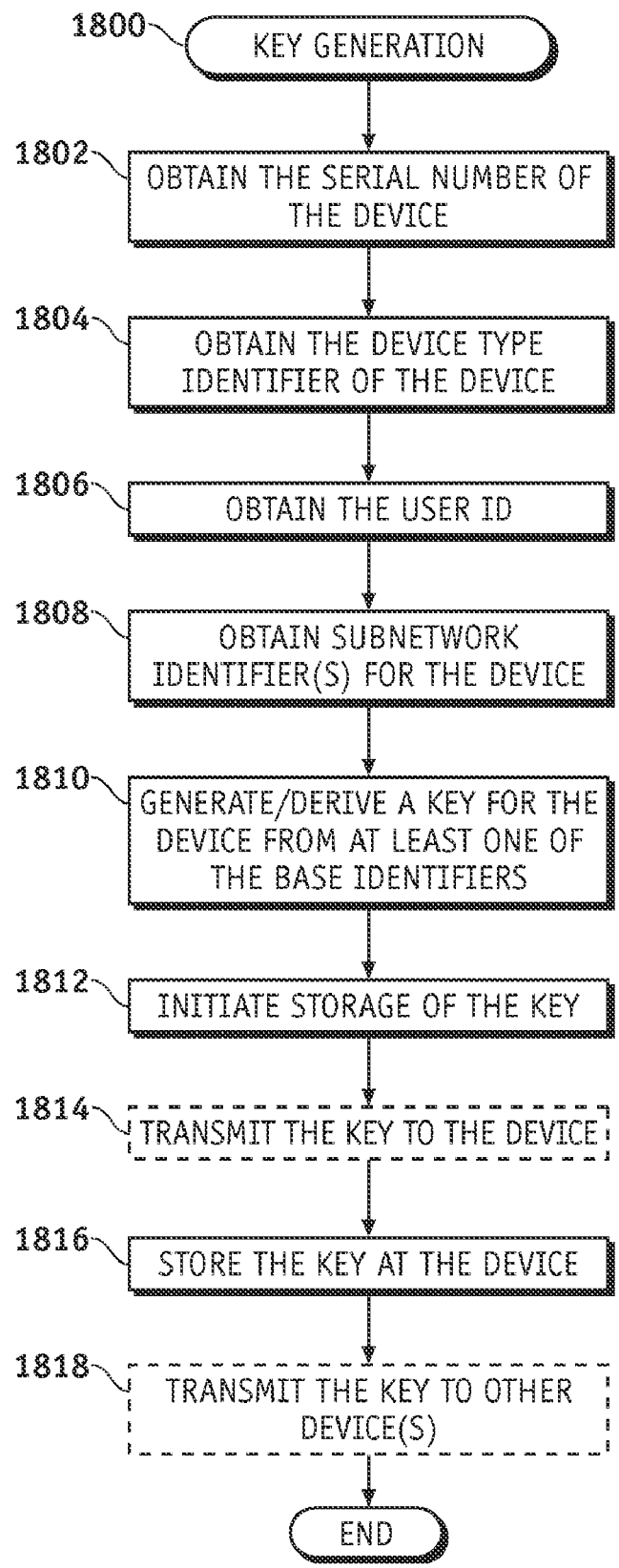
FIG. 24 is a flow chart that illustrates an exemplary key generation process.

A medical device network as described herein includes any number of wireless medical devices configured to communicate with each other using wireless data communication links. To facilitate such data transfer, each device in the network is identified using a key that is unique within the network environment (and possibly unique beyond the network environment). In this regard, FIG. 24 is a flow chart that illustrates an exemplary key generation process 1800 that can be used to derive the keys for the devices. Once a key is generated for a device, that device is configured, initialized, or set up for operation in the medical device network using its unique key.

Key generation process 1800 can be utilized to generate device keys from at least one base identifier for the device, where a "base identifier" is any value, quantity, bit string, or character string that is associated with the device and/or with characteristics of deployment of the device within the medical device network. Accordingly, process 1800 may begin by obtaining one or more of such base identifiers (tasks 1802, 1804, 1806, 1808). In an embodiment where the device itself generates the key, a base identifier may be obtained from the memory of the device itself, via a user interface of the device, or it may be received from another device in the medical device network. In an embodiment where a programming device generates the key, a base identifier may be obtained from the medical device, from the memory of the programming device, or from another device in the medical device network.

The serial number of the medical device may be used as one base identifier in key generation process 1800. Accordingly, process 1800 may obtain a serial number for the device (task 1802). In practice, a serial number may or may not be unique across different device types, however, it should be unique for a given device type. As used here, a "device type" represents a grouping or categorization of medical devices that might be used in a medical device network. For example, the device type may identify the primary function of a device: infusion pumps may be a first device type; BG sensor transmitters may be a second device type; BG meters may be a third device type; etc. The device type may be used as another base identifier in process 1800. Accordingly, process 1800 may obtain a device type identifier for the device (task 1804).

Yet another suitable base identifier is a user identifier for the user of the device, where the user identifier may identify a patient-user of the device, a caregiver-user of the device, a parent-user of the device, or the like. Accordingly, key generation process 1800 may obtain a user identifier for a user of the device (task 1806). In practice, the user identifier can be employed to distinguish different user classes from one another (for example, a patient-user may have different access rights than a caregiver-user). The user identifier could be identical to (or derived from) a customer ID that is assigned when an order for the medical device is placed. Alternatively, the user identifier could be programmed by the patient as a personalized ID. One application of this user identifier could be to provide limited access to a caregiver for certain functions such as data downloads. Since it would be used in conjunction with the device serial number, the user identifier may be realized as a relatively small string to differentiate between the different user classes. For example, in the case of a patient versus caregiver scenario, one bit would be sufficient to distinguish between the two user classes.

Yet another suitable base identifier could be one that distinguishes subnetworks within the medical device network. Subnetworks may be established to restrict the amount of wireless transmissions in the network; devices may be configured such that they only communicate with other devices within a designated subnetwork. For this example, a particular subnetwork identifier will be common to a subset of devices in the medical device network. For a network of N medical devices, the subnetwork identifier should be large enough to accommodate N–1 different subnetworks. Accordingly, key generation process 1800 may obtain one or more subnetwork identifiers for the device (task 1808). Of course, if the network does not support subnetworks, then task 1808 will be omitted.

After the base identifier(s) have been obtained, the key for the device can be generated/derived from one or more of the base identifiers (task 1810). In certain embodiments, task 1810 derives the key from a plurality of base identifiers. The base identifiers may serve as inputs to a suitably designed algorithm that generates the unique key as an output. In practical embodiments, a key is realized as a string of bits having an appropriate length. The number of bits assigned to the various base identifiers and to the computed key would be sufficiently large to accommodate the number of systems expected to be produced over time, thus ensuring uniqueness. Keys remain fixed once they are generated unless otherwise updated to reflect a change in one or more of the base identifiers or to reflect a network or device reconfiguration.

Key generation process 1800 may also initiate storage of the key at the device (task 1812). In an embodiment where the device itself generates the key, task 1812 will be performed by the device. In an embodiment where a programming device generates the key, task 1812 will be performed by the programming device. In such an embodiment, process 1800 may transmit the key from the programming device to the device (task 1814) for storage at the device. Task 1814 is depicted in dashed lines to indicate its optional nature. In response to task 1812, the device stores the key in its internal memory (task 1816). In certain embodiments, process 1800 may also transmit the key to one or more other devices in the medical device network (task 1818). Task 1818 is depicted in dashed lines to indicate its optional nature. Depending upon the embodiment, task 1818 may be performed by the device itself and/or by a programming device. For example, task 1818 may transmit the key to all other devices in the network. As an alternative example, task 1818 may transmit the key to a designated master device in the network.

In various embodiments, each medical device would have the capability of being programmed with the keys of other devices in the network. A device may also be capable of receiving one or more of the base identifiers from another device in the network. The programming can be performed manually using a suitably equipped computer device (e.g., a personal computer), via local or portable memory storage, using network access, using a wireless PDA, or using any device having the desired functionality and user interface features. Indeed, any device within the network may be configured to support such programming features. Alternatively, keys and/or base identifiers can be preloaded into a device at the factory or at a caregiver office.

Keys and/or base identifiers may be exchanged by wireless medical devices in the network using an appropriate "marrying" function. For example, a marrying function may be manually initialized such that a first device queries a second device for data; the first device can store the data after it receives it. This marrying function may be initialized via capacitive sensing between the two devices. Once the marrying function is initialized, the data can be exchanged via: the capacitive connection itself; RFID transmissions; proprietary or other RF transmissions per a network communication protocol; or some other RF data communication protocol such as Bluetooth, ZigBee, etc.

The two devices in question could also connect via magnetic sensing and then trade information as described in the preceding paragraph. The data may also be transferred using the magnetic connection. The two devices in question could also connect via optical sensing (e.g., IR) and then trade data as described in the preceding paragraph. The data may also be transferred using the optical connection.

A wireless medical device network can handle wireless network communications using different protocols to suit the needs of the particular application, network topology, operating conditions, or the like. Moreover, the medical devices may utilize device keys when processing wireless data packets within the medical device network. The device keys may serve as identifiers to distinguish different protocols, device features, and/or other variable characteristics (described in more detail below). For example, the keys may be used in connection with the various processes depicted in FIGS. 25-30.

Figure 25:
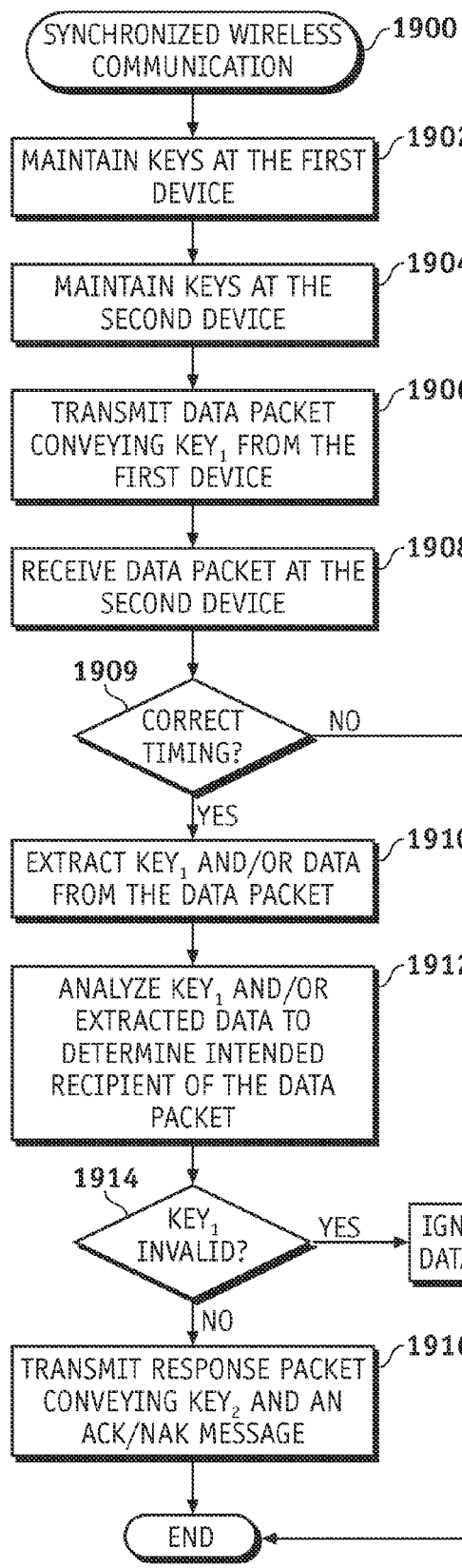
FIG. 25 is a flow chart that illustrates a synchronized wireless communication process suitable for use in a wireless medical device network.
Figure 26:
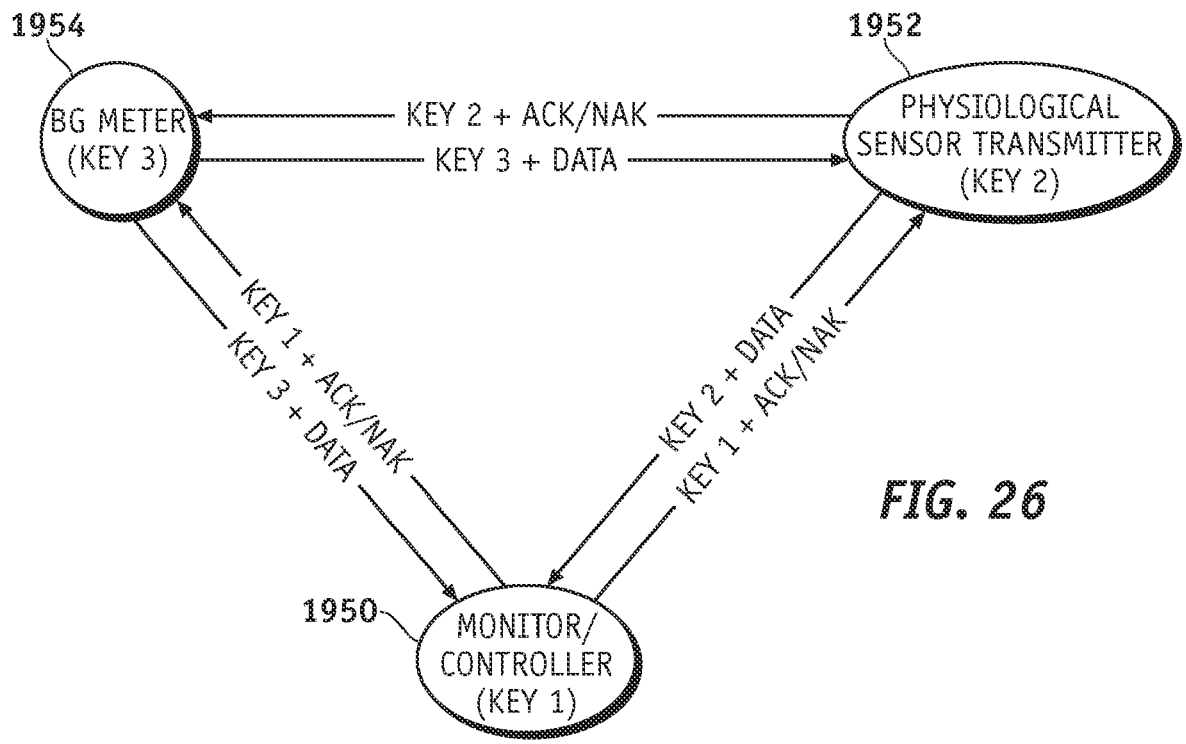
FIG. 26 is a diagram that depicts data packet exchanges in accordance with the process shown in FIG. 25.

FIG. 25 is a flow chart that illustrates a synchronized wireless communication process 1900 suitable for use in a wireless medical device network, and FIG. 26 is a diagram that depicts data packet exchanges in accordance with process 1900. This example assumes that each wireless medical device in the network has knowledge of the keys of the other devices. In this regard, each device may store a table of the keys utilized within the medical device network. Moreover, this example assumes that the devices communicate wireless data packets using a synchronized data communication protocol. The simple example shown in FIG. 26 includes three medical devices configured to operate in a wireless network topology: a monitor/controller 1950 that is identified by KEY1; a physiological sensor transmitter 1952 that is identified by KEY2; and a BG meter 1954 that is identified by KEY3. In practice, any device may be capable of sending data to another device and, in response, receiving an acknowledgement or a negative acknowledgement. The following example has been simplified for ease of description.

In connection with synchronized wireless communication process 1900, all of the device keys are maintained at a first device (task 1902), which serves as the transmitting device in this example, and all of the device keys are maintained at a second device (task 1904), which serves as the receiving device in this example. In practice, each data packet transmitted by a device in the network will include the key of the transmitting device. Thus, the first device transmits a data packet intended for the second device (task 1906), and that data packet conveys a quantity of data along with the key for the first device, i.e., the "first key." The quantity of data represents any non-overhead data of interest. During normal operation, the first device will transmit packets according to a negotiated synchronous transmit schedule such that the second device will expect to receive packets from the first device at certain designated times.

The data packet transmitted at task 1906 is received by the second device (task 1908), and the second device determines whether the timing of the received data packet is in accordance with the particular synchronization settings (query task 1909). In other words, the second device checks whether the timing and synchronization of the received data packet is correct or as anticipated. If so, then the received data packet was actually intended for the second device. If not, then the received data packet can be ignored (task 1918). If the timing characteristics of the received data packet are correct, then the second device processes the received packet to extract the first key and/or to extract the non-overhead data (task 1910). The second device can then analyze the extracted key and/or the extracted non-overhead data to determine whether the data packet was intended for the second device (task 1912). As mentioned above, the devices exchange data in a synchronous manner. Therefore, the second device will expect to receive data from the first device (and possibly other devices in the network) in accordance with a designated time schedule. If the extracted key does not match the anticipated key (the first key in this example), then the second device will determine that the received packet was not intended for it. In practice, two things need to happen for the second device to either ACK or NAK. First, the time the message was received must correspond to the synchronized setting. If not, the second device should not be "listening" for the message and no NAK will be sent. Second, if the message is intended for the second device based on the synchronized timing but the data is corrupted or is valid data that is meant for another device, then a NAK will be sent. Thus, a NAK is generated in response to corrupt or invalid data if the timing is correct. If the timing is not correct, then the received message can be ignored. Additionally or alternatively, if the extracted non-overhead data has unexpected characteristics, then the second device will determine that the received packet was not intended for it. Under normal conditions, the non-overhead data may have certain trending characteristics that do not change very rapidly. If the extracted non-overhead data has unusually abrupt transitions or unintelligible content, then the second device might assume that the received packet was erroneously received.

In some embodiments, medical devices in the network may designate certain devices keys as invalid keys, where an invalid key corresponds to an unsupported or blocked device. For example, if the second device designates the first key as a valid key (query task 1914), then the second device can support wireless data communication with the first device. Accordingly, the second device can generate and transmit a suitable response packet (task 1916) intended for the first device. The response packet conveys the key for the second device, i.e., the "second key," along with an acknowledgement message (ACK) or a negative acknowledgement message (NAK). If, for example, the second device determines that the received packet was not actually intended for it, then the response packet may include a NAK. If, however, query task 1914 determines that the first key is an invalid key, then the second device may simply ignore the received packet (task 1918) without taking any further action.

Referring to FIG. 26, BG meter 1954 transmits a packet containing KEY3 and a data payload to monitor/controller 1950, which then responds with a packet containing KEY1 and an ACK or a NAK message. A similar transmit/response scheme may be followed for a data payload transmitted from physiological sensor transmitter 1952 to monitor/controller 1950, and for a data payload transmitted from BG meter 1954 to physiological sensor transmitter 1952. The timing of the transmit and response packets between the various medical devices is governed by the negotiated synchronous timing scheme.

Figure 27:
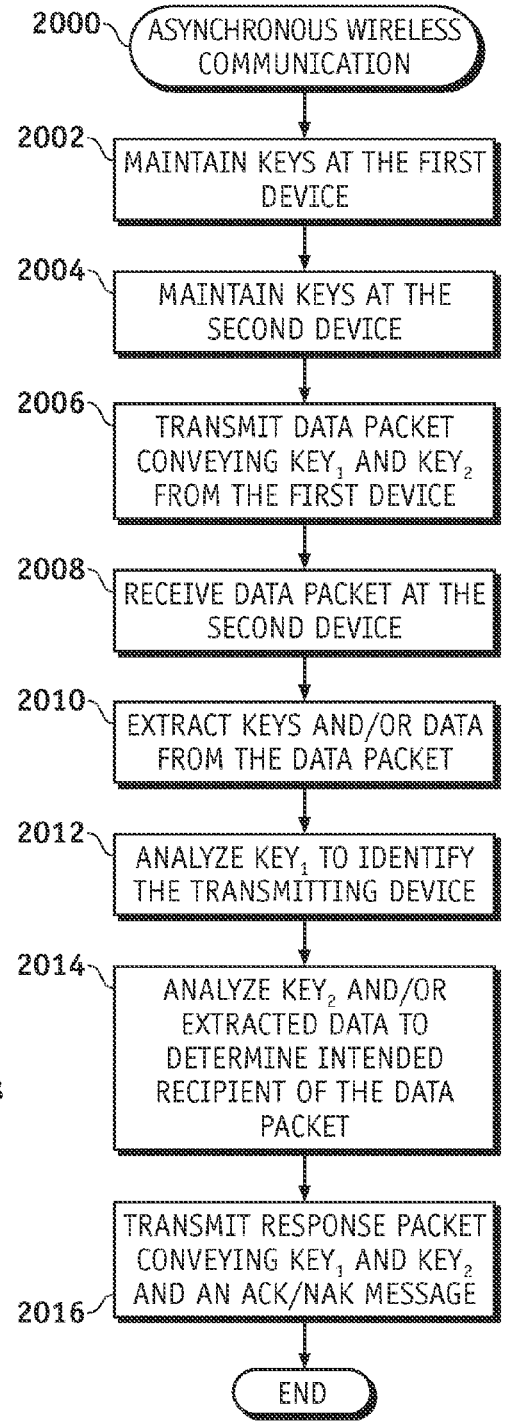
FIG. 27 is a flow chart that illustrates an asynchronous wireless communication process suitable for use in a wireless medical device network.
Figure 28:
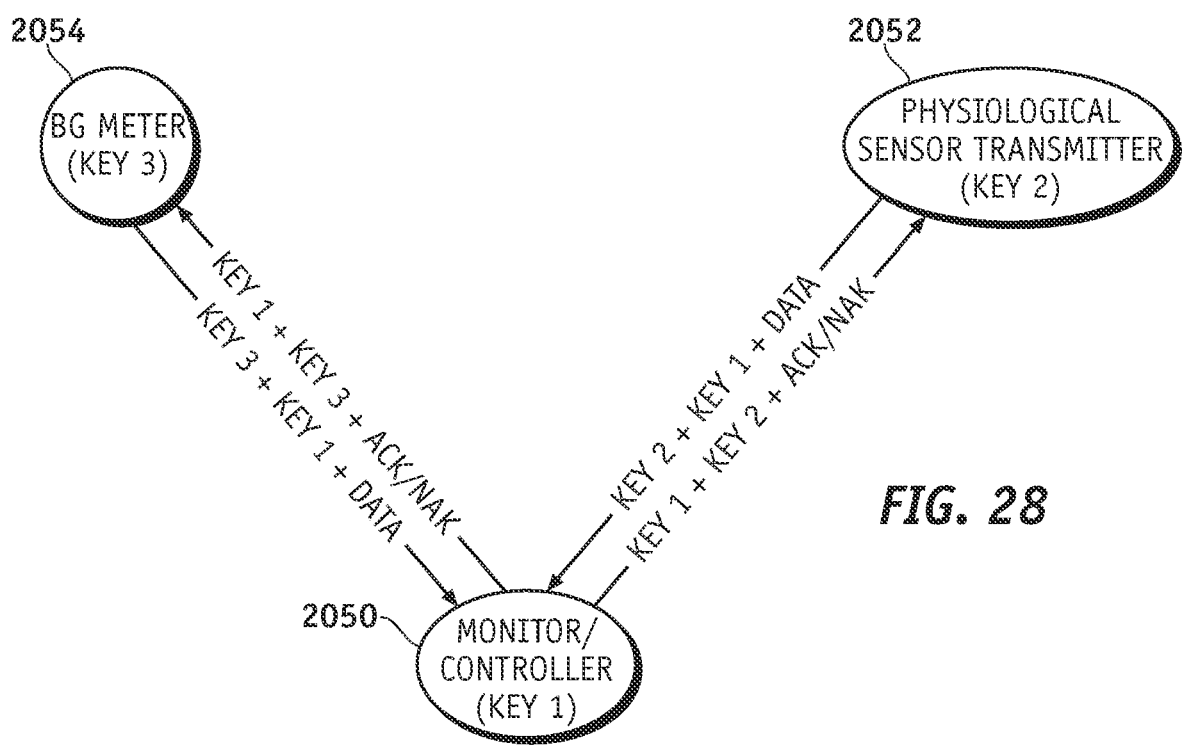
FIG. 28 is a diagram that depicts data packet exchanges in accordance with the process shown in FIG. 27.

FIG. 27 is a flow chart that illustrates an asynchronous wireless communication process 2000 suitable for use in a wireless medical device network, and FIG. 28 is a diagram that depicts data packet exchanges in accordance with process 2000. This example assumes that each wireless medical device in the network has knowledge of the keys of the other devices. Moreover, this example assumes that the devices communicate wireless data packets using an asynchronous data communication protocol. The simple example shown in FIG. 28 includes three medical devices configured to operate in a wireless network topology: a monitor/controller 2050 that is identified by KEY1; a physiological sensor transmitter 2052 that is identified by KEY2; and a BG meter 2054 that is identified by KEY3. In practice, any device may be capable of sending data to another device and, in response, receiving an acknowledgement or a negative acknowledgement. The following example has been simplified for ease of description.

In connection with asynchronous wireless communication process 2000, all of the device keys are maintained at a first device (task 2002), which serves as the transmitting device in this example, and all of the device keys are maintained at a second device (task 2004), which serves as the receiving device in this example. In practice, each data packet transmitted by a device in the network will include the key of the transmitting device and the key of the intended receiving device. Thus, the first device transmits a data packet intended for the second device (task 2006), and that data packet conveys a quantity of data along with the key for the first device, i.e., the "first key," and the key for the second device, i.e., the "second key." The quantity of data represents any non-overhead data of interest.

The data packet transmitted at task 2006 is received by the second device (task 2008), and the second device processes the received packet to extract the keys and/or to extract the non-overhead data (task 2010). The second device can then analyze the first key to identify the transmitting device (task 2012). For example, the second device may look up the extracted key in a table to determine the origin of the received packet. This may be desirable in embodiments where subsequent processing of the received packet is dependent upon the identity of the transmitting device. The second device may also analyze the extracted second key and/or the extracted non-overhead data to determine whether the data packet was intended for the second device (task 2014). If the extracted second key does not match the key of the second device, then the second device will determine that the received packet was not intended for it. If the received key is a valid key for a device in the network then the second device can ignore the message, understanding that the intended receiving device will either ACK or NAK. If, however, the received key is invalid for any device in the network, then the second device will generate a NAK. Additionally or alternatively, if the extracted non-overhead data has unexpected characteristics (as described above), then the second device will determine that the received packet was not intended for it.

Eventually, the second device can generate and transmit a suitable response packet (task 2016) intended for the first device. The response packet conveys the first key, the second key, and an ACK/NAK message. If, for example, the second device determines that the received packet was not actually intended for it, then the response packet may include a NAK.

Referring to FIG. 28, BG meter 2054 transmits a packet containing KEY3, KEY1, and a data payload to monitor/controller 2050, which then responds with a packet containing KEY1, KEY3, and an ACK or a NAK message. A similar transmit/response scheme may be followed for a data payload transmitted from physiological sensor transmitter 2052 to monitor/controller 2050. The transmission of both originating and destination keys in the above manner facilitates asynchronous packet transmission within the medical device network.

Figure 29:
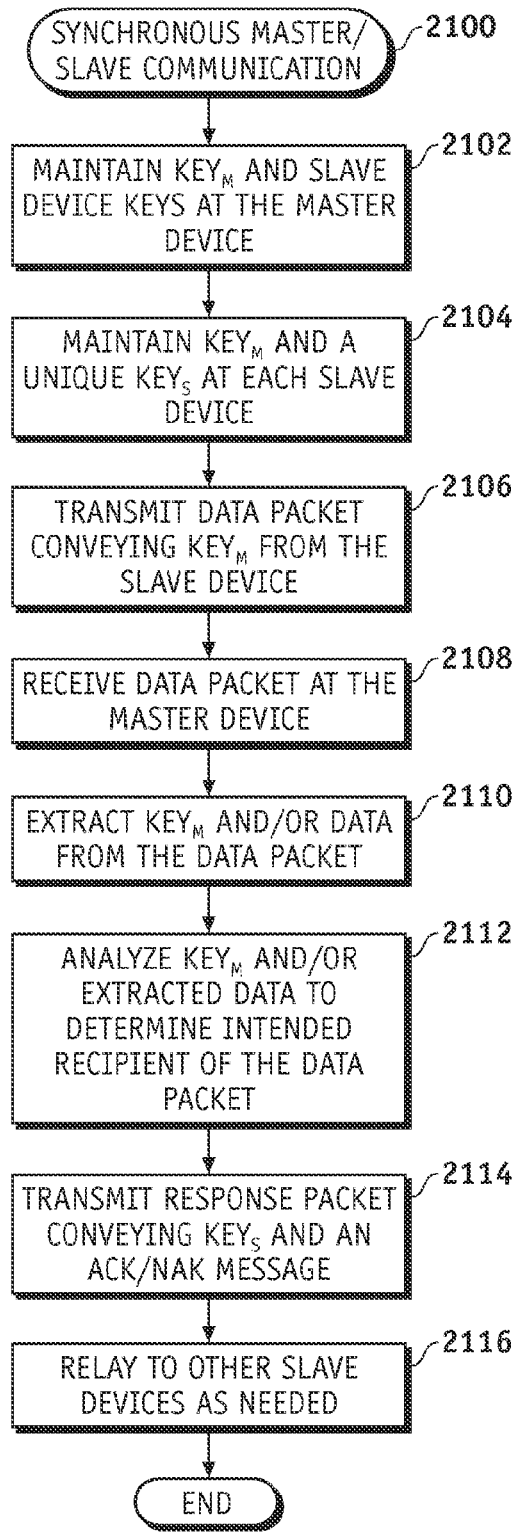
FIG. 29 is a flow chart that illustrates a synchronous master-slave wireless communication process suitable for use in a wireless medical device network.
Figure 30:
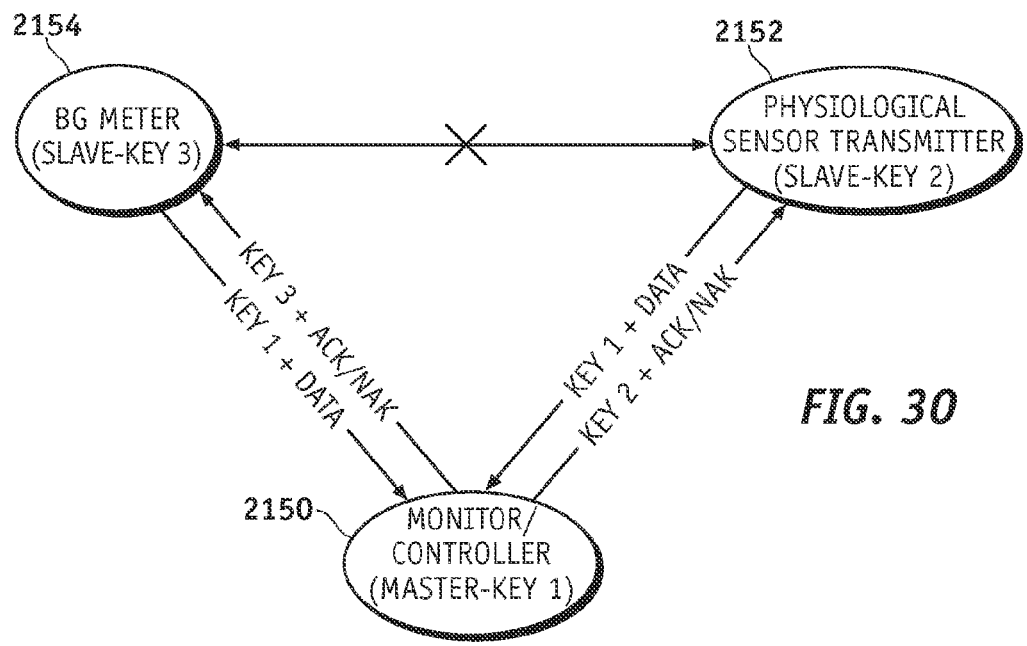
FIG. 30 is a diagram that depicts data packet exchanges in accordance with the process shown in FIG. 29.

In another embodiment of a medical device network, one device (usually the monitor/controller or the infusion pump in a fluid infusion system) is designated as the master device and all other devices are designated as slave devices. The master device has knowledge of the keys for all of the devices in the network, while each slave device has knowledge of only its own key and the key for the master device. In this regard, FIG. 29 is a flow chart that illustrates a synchronous master-slave wireless communication process 2100 suitable for use in a wireless medical device network, and FIG. 30 is a diagram that depicts data packet exchanges in accordance with process 2100. This example assumes that the devices communicate wireless data packets using a synchronized data communication protocol. The simple example shown in FIG. 30 includes three medical devices configured to operate in a wireless network topology: a monitor/controller 2150 that is identified by KEY1; a physiological sensor transmitter 2152 that is identified by KEY2; and a BG meter 2154 that is identified by KEY3. Here, monitor/controller 2150 is the master device. In practice, any device may be capable of sending data to another device and, in response, receiving an acknowledgement or a negative acknowledgement. The following example has been simplified for ease of description.

In connection with process 2100, all of the device keys, including the master device key ($KEY_M$) and each slave device key ($KEY_S$), are maintained at the master device (task 2102), which serves as the receiving device in this example. In addition, the master device key and the respective slave device key is maintained at each slave device within the medical device network (task 2104). In this example, one of the slave devices serves as the transmitting device. In practice, each data packet transmitted by a slave device in the network will include the key of the master device, and need not include any other key. Thus, the slave device transmits a data packet intended for the master device (task 2106), and that data packet conveys a quantity of data along with the key for the master device, i.e., the "master key." The quantity of data represents any non-overhead data of interest. During normal operation, the slave device will transmit packets according to a negotiated synchronous transmit schedule such that the master device will expect to receive packets from the slave device at certain designated times.

The data packet transmitted at task 2106 is received by the master device (task 2108), and the master device processes the received packet to extract the master key and/or to extract the non-overhead data (task 2110). The master device can then analyze the extracted master key and/or the extracted non-overhead data to determine whether the data packet was intended for the master device (task 2112). As mentioned above, the devices exchange data in a synchronous manner. Therefore, the master device will expect to receive data from the slave device (and possibly other devices in the network) in accordance with a designated time schedule. If the extracted master key does not match the anticipated key (KEY1 in this example), then the master device will determine that the received packet was not intended for it. Additionally or alternatively, if the extracted non-overhead data has unexpected characteristics (described above), then the master device will determine that the received packet was not intended for it.

Eventually, the master device can generate and transmit a suitable response packet (task 2114) intended for the slave device. The response packet conveys the key for the slave device and an ACK/NAK message. If, for example, the master device determines that the received packet was not actually intended for it, then the response packet may include a NAK.

The master device, which functions as a communication coordinator or a hub in this example, may relay data (after appropriate data re-formatting if required) to other slave devices as needed (task 2116). For example, BG meter 2154 can send data to monitor/controller 2150, which may then forward the data to physiological sensor transmitter 2152. Data packets transmitted by the master device may convey any type of data. For example, a data packet transmitted by the master device may convey a master clock time to which the other devices synchronize.

Referring to FIG. 30, BG meter 2154 transmits a packet containing KEY1 (the master key) and a data payload to monitor/controller 2150, which then responds with a packet containing KEY3 (the slave key for BG meter 2154) and an ACK or a NAK message. Alternatively, the response packet need not include any keys; the specific response time slot would identify the responding device to the originating device. A similar transmit/response scheme may be followed for a data payload transmitted from physiological sensor transmitter 2152 to monitor/controller 2150. Notably, under this master-slave scheme physiological sensor transmitter 2152 and BG meter 2154 are unable to directly communicate wireless data packets between one another; they communicate with each other indirectly via the master device. The timing of the transmit and response packets between the various medical devices is governed by the negotiated synchronous timing scheme.

Notably, for synchronized communications, the ACK/NAK packet need not require the key of the transmitting device. Moreover, asynchronous communication can be supported in a system embodiment where the transmitting device sends its key along with the ACK/NAK packet. In such an embodiment the transmission of the responding device key identifies the responding device to the master device in a manner that need not rely on any synchronized timing.

Figure 31:
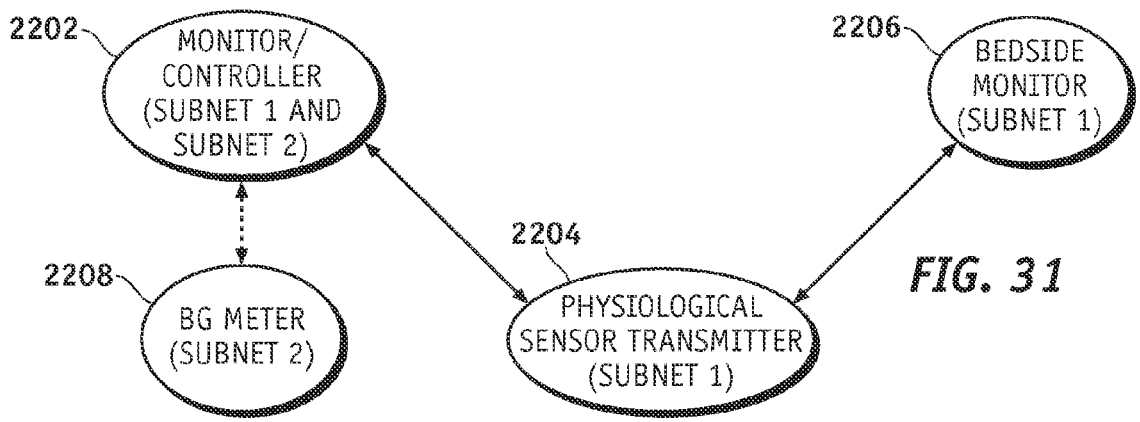
FIG. 31 is a diagram that depicts two subnetworks of wireless medical devices in a medical device network.

Depending upon the network deployment, it may not be necessary for each medical device in the network to be able to communicate with all other medical devices in the network. It may be desirable for a device to communicate with only a subset of the devices within the network. In this regard, FIG. 31 is a diagram that depicts two subnetworks of wireless medical devices in a medical device network. In this simplified example, the network includes a monitor/controller 2202, a physiological sensor transmitter 2204, a bedside monitor 2206, and a BG meter 2208. Subnetwork one includes monitor/controller 2202, physiological sensor transmitter 2204, and bedside monitor 2206, and subnetwork two includes monitor/controller 2202 and BG meter 2208. Each device may be associated with one or more codes or suitably formatted subnetwork indicators that identify the different subnetworks to which that device belongs. Thus, in this example, monitor/controller 2202 would have two different subnetwork identifiers.

In practice, different subnetworks within the medical device network may utilize different synchronized timing schemes to avoid packet collisions. In certain embodiments, the medical device network may be configured to adjust the different synchronized timing schemes to enable concurrent operation of the various subnetworks (e.g., avoid simultaneous packet transmissions for devices that are common to multiple subnetworks). To improve efficiency and to reduce unnecessary packet transmissions, medical devices in one subnetwork may be configured to avoid communication with medical devices in other subnetworks, and vice versa. This functionality can be achieved in one embodiment in the following manner. Devices in a given subnetwork maintain a list of valid device keys corresponding to other devices in the subnetwork, and maintain a list of invalid device keys corresponding to devices that are not in the subnetwork. Consequently, packets received by devices within the subnetwork must be associated with a valid device key, otherwise the received packets are discarded or ignored.

In some network deployments, it may be possible for a wireless medical device to perform a broadcast transmission of data packets for potential reception by a plurality of destination devices in the network. In this case, the receiving devices will respond (ACK/NAK) either in a specified predetermined sequence or in a pseudorandom order. In the event of a NAK or no response from one or more receiving devices, the transmitting device can re-transmit the packet to all devices and await ACK/NAK messages again. Such re-transmissions can be repeated for a predetermined number of retry attempts before alerting the user.

Figure 32:
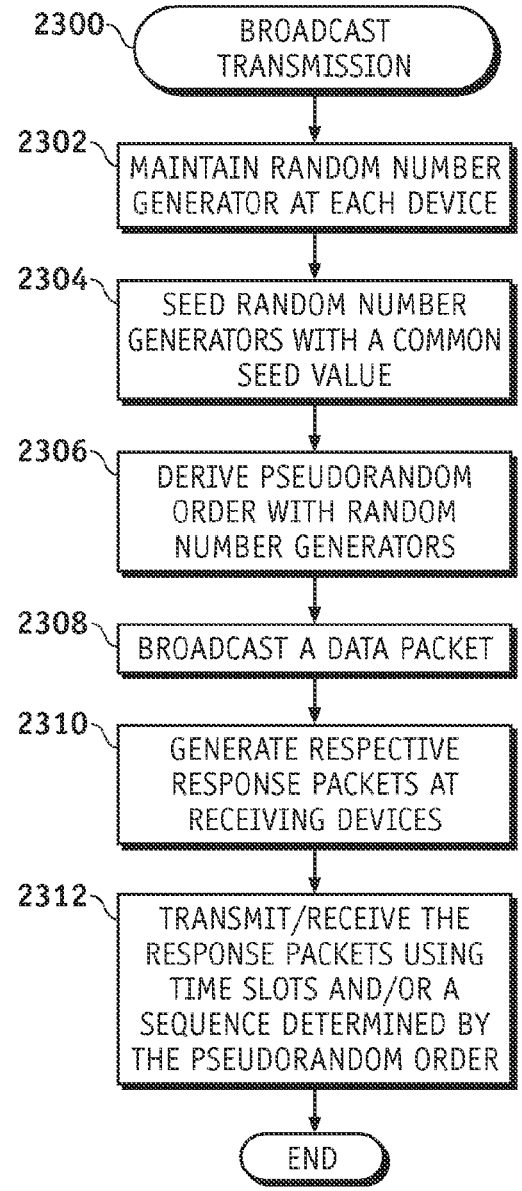
FIG. 32 is a flow chart that illustrates a broadcast transmission process suitable for use in a wireless medical device network.
Figure 33:
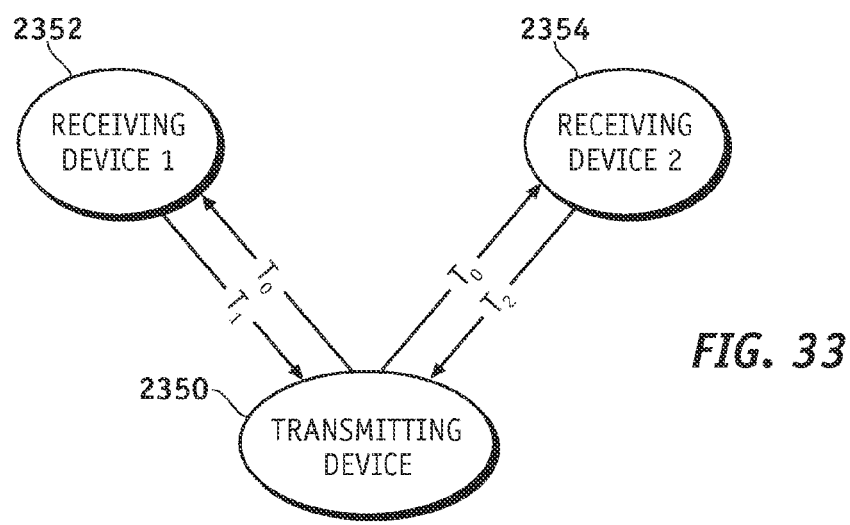
FIG. 33 is a diagram that depicts data packet exchanges in accordance with the process shown in FIG. 32.

FIG. 32 is a flow chart that illustrates a broadcast transmission process 2300 suitable for use in a wireless medical device network, and FIG. 33 is a diagram that depicts data packet exchanges in accordance with process 2300. This example assumes that the network devices are configured to communicate data in a synchronized manner using a common carrier frequency. At least the following two scenarios are also possible. First, devices within the "repeater" network can be at the same frequency but each device can communicate at a different frequency with a patient-held device. Second, devices within the network can be at different frequencies as long as at least a pair of devices are at the same frequency to allow communication. In FIG. 33, the transmitting device 2350 is configured to broadcast wireless data packets to a plurality of receiving devices, including a first receiving device 2352 and a second receiving device 2354.

In connection with broadcast transmission process 2300, an instantiation of a random number generator is maintained at each device (task 2302). Referring to FIG. 22, a random number generator may be realized in, for example, processing logic 1618 of the respective device. The "same" random number generator is operable at each device such that, if seeded with the same value, each instantiation of the random number generator will generate the same sequence of pseudorandom numbers. Accordingly, process 2300 may seed each instantiation of the random number generator with a suitable common seed value (task 2304) as an initialization step. This enables process 2300 to derive a pseudorandom order at the devices using the random number generators (task 2306), where the pseudorandom order is derived in response to the common seed value.

A transmitting device then broadcasts a data packet to a plurality of other devices in the wireless medical device network (task 2308) using an appropriate wireless data transmission protocol. FIG. 33 depicts this broadcast transmission occurring at time $T_0$. Assuming that multiple devices receive the broadcast packet, the receiving devices will generate respective response packets (task 2310) for transmission back to the transmitting device. Thereafter, the receiving devices will transmit the response packets (and the originating device will receive the response packets) using time slots and/or using a sequence that is determined by the pseudorandom order (task 2312). In one embodiment, the pseudorandom order (which will be shared with the network devices) is utilized to derive different response time slots for the receiving devices; each receiving device will have a pseudorandomly designated time slot for transmitting its response packet. In another embodiment, the pseudorandom order is utilized to derive a transmit sequence for the receiving devices; each receiving device will transmit its response packet in a designated sequential order. FIG. 33 depicts the response for first receiving device 2352 being transmitted at time $T_1$ and the response for second receiving device 2354 being transmitted at time $T_2$.

Thus, the transmitting device receives the response packets in a pseudorandom order that is based upon the common seed value for the random number generators. Since the transmitting device also maintains an instantiation of the random number generator (having the same seed value), it can correlate the received response packets to the receiving devices. In this manner, the transmitting device can resolve the identities of the receiving devices and process the respective response packets accordingly.

A wireless medical device may be suitably configured to function as a "repeater" in order to transmit messages over a longer range. In practice, such a repeater device might be realized with a relatively stationary device such as a bedside monitor or a remote annunciator. A medical device network may include any number of repeater devices configured to forward wireless messages within the network environment. In addition, this repeater device may serve as a translation device, connected via a USB link to a PC. In this case the repeater device may be capable of operating off the power provided by the USB interface when connected to a PC, or through an AC adapter providing power through the physical USB connector. Alternatively, such a repeater/translation device could be configured to directly communicate with the Internet (using any appropriate data communication technique or technology), in which case it would have its own IP address.

Figure 35A:
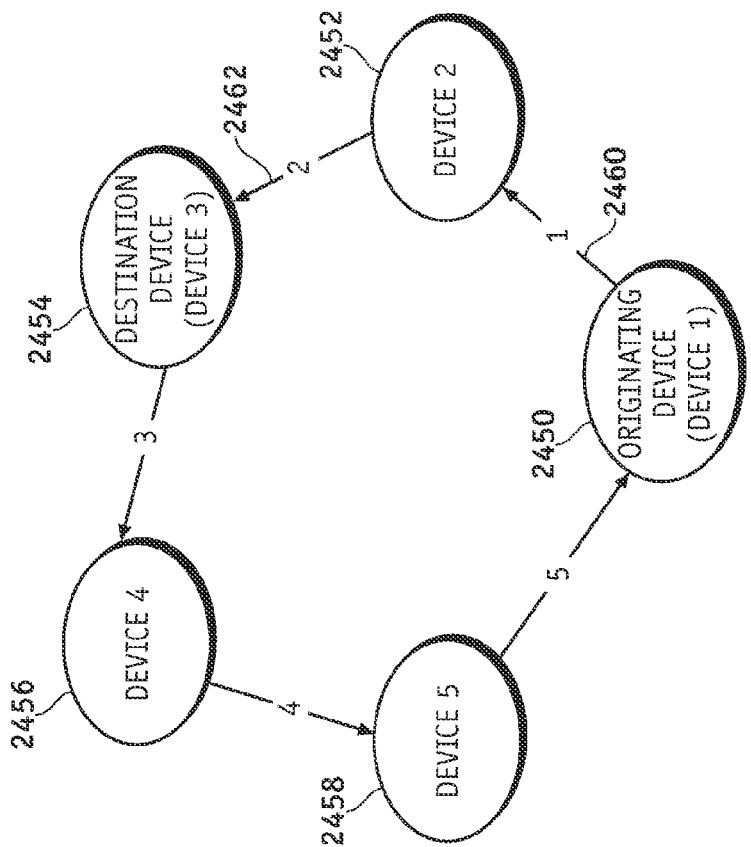
FIG. 35A is a diagram that depicts data packet exchanges in accordance with the process shown in FIG. 34.
Figure 34:
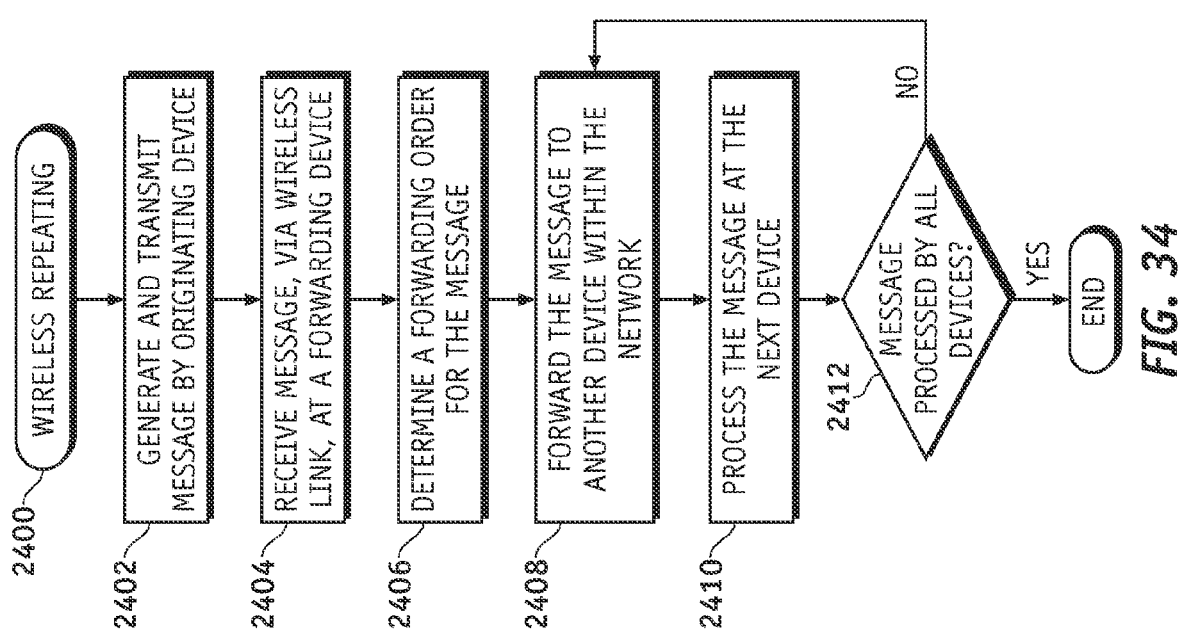
FIG. 34 is a flow chart that illustrates a wireless repeating process suitable for use in a wireless medical device network.

FIG. 34 is a flow chart that illustrates a wireless repeating process 2400 suitable for use in a wireless medical device network, and FIG. 35A is a diagram that depicts data packet exchanges in accordance with process 2400. The example depicted in FIG. 35A includes an originating device 2450 (i.e., the first device), a second device 2452, a destination device 2454 (i.e., the third device), a fourth device 2456, and a fifth device 2458. Here, originating device 2450 transmits a wireless message or data packet that is intended for destination device 2454. Process 2400, or an equivalent variant thereof, is used to forward the message to destination device 2454.

Wireless repeating process 2400 may begin with an originating device generating a message that is intended for a destination device (task 2402). In this embodiment, the message is conveyed using wireless data packets, and the originating device transmits the message using a suitable wireless data communication link. The message may include or convey any type of data, including, without limitation: alarms for the medical device network; status information; user reminders; patient data; or any of the data types described above.

The originating device may be configured to transmit messages in accordance with a predetermined ordered sequence, a pseudorandom sequence, or any suitable sequence for a plurality of devices within the medical device network. In the example shown in FIG. 35A, the ordered sequence corresponds to a "circular" path that follows the device numbers. Thus, if fourth device 2456 is the originating device, then the ordered sequence is as follows: fifth device 2458; first device 2450; second device 2452; third device 2454; fourth device 2456. If second device 2452 is the originating device, then the ordered sequence is as follows: third device 2454; fourth device 2456; fifth device 2458; first device 2450; second device 2452. The sequence of devices in the medical device network may also represent a forwarding order for wireless packets routed throughout the network. In practice, the forwarding order may take any desired path, and one or more devices in the network may be omitted from the path. Moreover, the forwarding path may return to a device in the network for the sake of redundancy.

For purposes of this example, first device 2450 is the originating device and, therefore, task 2402 transmits the message from first device 2450 to second device 2452 via a wireless data communication link 2460. Under normal operating conditions, second device 2452 will receive the message via wireless data communication link 2460. This example assumes that the message is intended for third device 2454 (i.e., the destination device). Accordingly, second device 2452 serves as a repeater/forwarding device for the message. If, however, the message is intended for second device 2452, then the message need not be forwarded within the medical device network.

The receiving device (the second device 2452 in this example) may process the message and/or overhead data associated with the message to determine the desired forwarding order for the message (task 2406). As mentioned above, the forwarding order represents a sequence of devices in the medical device network and the forwarding order may be based upon the location of the destination device within the medical device network. For example, a device may determine the forwarding order in a manner that favors paths having less "hops" between wireless devices in the network. In this embodiment, the forwarding order is fixed for a given network topology and the receiving device may consult a stored device sequence to determine the identity of the forward-to device.

The receiving device will then format the received message (if necessary) for forwarding, and forward the received message within the medical device network in an appropriate manner that is intended to reach the destination device. The receiving device will forward the message to another device in the network via a wireless data communication link (task 2408). Depending upon the network topology and the forwarding order, this other device may be the destination device itself or an intermediate device located "before" the destination device. FIG. 35A depicts an example where second device 2452 forwards its received message to third device 2454 via a wireless data communication link 2462. Here, third device 2454 is the intended destination device.

Generally, the forwarded message can be processed (task 2410) by each device as it progresses through the medical device network. If necessary, the devices can extract the payload data and process that data in an appropriate manner. Alternatively, the devices may analyze overhead data for purposes of message forwarding. In this example, wireless repeating process 2400 forwards the message within the medical device network until each of the devices has processed the message. This may occur even if the intended destination device has already received and processed the message. Accordingly, if the message has not been processed by all devices (query task 2412), then process 2400 may be re-entered at task 2408 to initiate additional forwarding of the message. Otherwise, process 2400 ends. Referring to FIG. 35A, the message may be forwarded from third device 2454 to fourth device 2456, from fourth device 2456 to fifth device 2458, and from fifth device 2458 back to first device 2450. First device 2450 may be suitably configured to recognize that it originated the message and, therefore, to disregard the message without forwarding it.

Wireless repeating process 2400 can be modified to accommodate the situation where a common message (e.g., an alarm message generated by a monitor device) is detected and forwarded by multiple devices. For instance, one of the devices in the medical device network may be a designated "broadcasting device" for a given message that is intended for a plurality of destination devices in the network. In practice, the broadcast message can be wirelessly received by one or more destination devices in the network. When this occurs, any destination device that has received the broadcast message can then wirelessly forward the message to one or more other destination devices. Notably, the common broadcast message can be concurrently forwarded using different forwarding paths within the medical device network. However, each device may have suitably configured processing logic that enables it to determine whether or not it has already received the forwarded message. If a device determines that it has already received (and forwarded) the common message, then it can choose to ignore it.

The broadcast message may convey an alarm for the medical device network. If so, then it is possible for each destination device that receives the alarm message to generate an alarm indication in response to the alarm message. This alarm indication may be an audible and/or visual indication, depending upon the desired configuration and user preferences. In certain embodiments, the wireless repeating technique described herein can also be utilized to handle alarm termination (silencing) messages. For example, an alarm termination message may be generated at a first device within the medical device network in any suitable manner (usually in response to user interaction with the device). The alarm termination message may be processed by the first device such that the alarm at the first device is terminated. In addition, the first device may wirelessly forward the alarm termination message to one or more destination devices within the network, with the goal of terminating the related alarms at the other devices. Thus, the forwarded alarm termination message can be wirelessly received at another device, which then terminates its alarm in response to the forwarded alarm termination message. The alarm termination message may be forwarded in this manner until all alarms are silenced.

A patient-held or patient-worn device may also be considered to be part of the medical device network and, therefore, subject to the message forwarding and repeating techniques described herein. For example, silencing an alarm at a repeater/annunciator device within the network may cause that device to generate (or forward) an alarm termination message for the patient device. Upon receipt of the alarm termination message, the patent device will terminate its alarm (if it is still active). Similarly, silencing an alarm at a patient device may cause the patient device to generate (or forward) an alarm termination message for one or more destination devices within the medical device network. Thereafter, the alarm termination message can be forwarded/broadcast within the network in the manner described above.

A device in the network may also be configured to not sound an alarm. This can be performed on a pre-programmed time schedule, such as night versus day, or as required at any time. In the latter scenario, to prevent accidentally silencing a device permanently, the device may be designed to switch to the pre-programmed mode at the prescribed time.

Figure 35B:
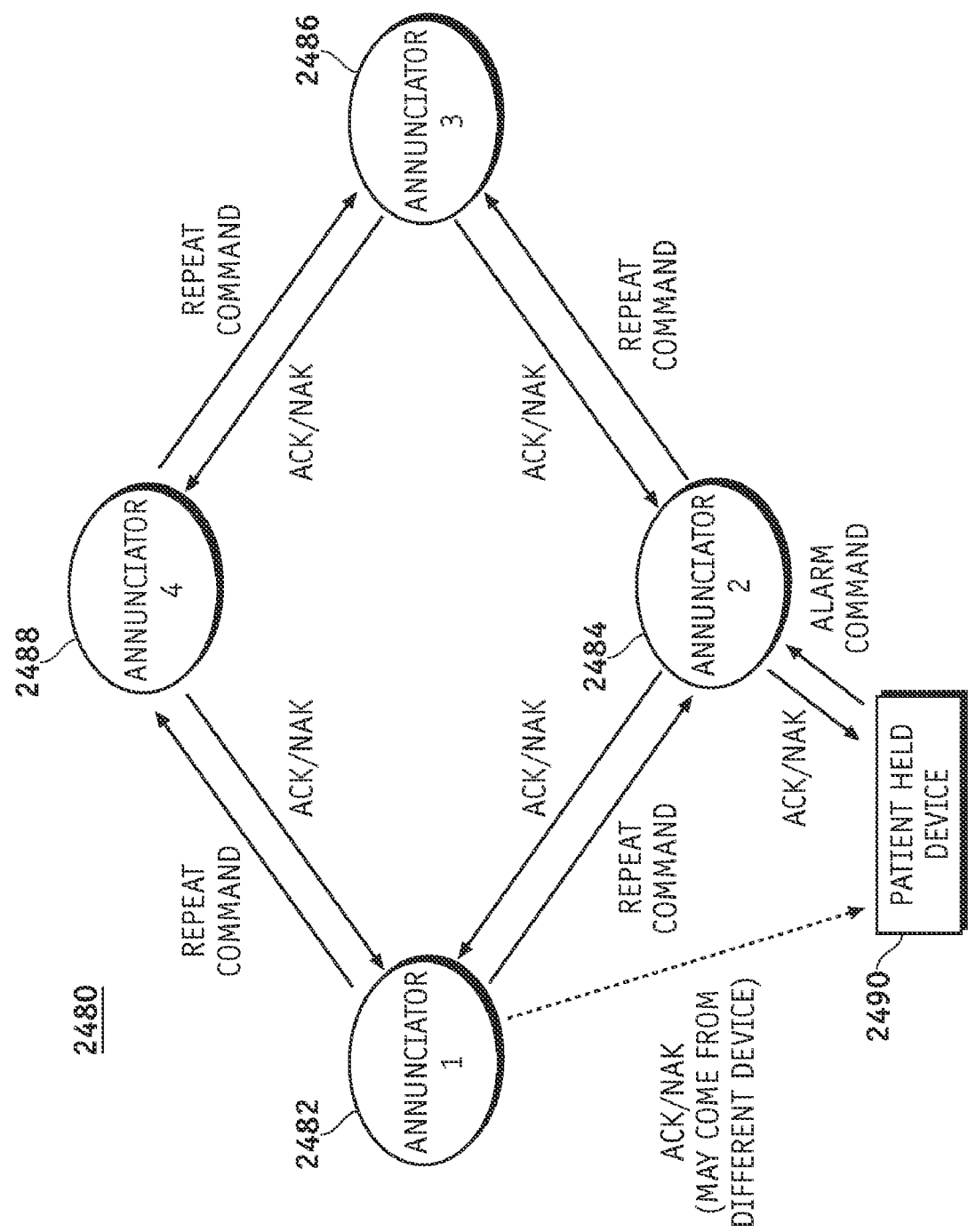
FIG. 35B is a diagram that represents a wireless annunciating and repeating process and system.

FIG. 35B is a diagram that illustrates a wireless annunciating and repeating system 2480, which may be realized in the context of a wireless medical device network. Process 2400 described above may be modified in an appropriate manner to support the operation of system 2480. Here, system 2480 includes four annunciator/repeater devices (identified by reference numbers 2482, 2484, 2486, and 2488). A given annunciator/repeater may be a full function device such as a bedside monitor, or a reduced function device with or without a user interface. Any number of these devices can be used in a wireless repeater network. The example depicted in FIG. 35B includes a patient-held device 2490 that transmits a message, typically an alarm or alert, that is received by annunciator/repeater 2484. Note that one or more of the annunciator/repeater devices can receive the message as the location of patient-held device 2490 is not known to the annunciator/repeater devices.

Here, annunciator/repeater 2484 forwards (repeats) the message to the next device in the link, and so on. Each annunciator/repeater device can sound the appropriate alarm/alert as the location of the caregiver is unknown. The receiving annunciator/repeater device may respond with an ACK or NAK to the transmitting annunciator/repeater device. The patient-held device 2490 will be capable of listening for, and responding to ACK/NAK commands. Moreover, patient-held device may not be in the same location during the period that the messages are being transmitted and, therefore, it is preferably configured to be able to communicate with each annunciator/repeater device in the chain. In FIG. 35B, patient-held device 2490 receives the ACK/NAK message annunciator/repeater 2482. The alarm can be silenced (temporarily or permanently) at the annunciator/repeater device. In this regard, a silence message will be transmitted by each annunciator/repeater device to the next one in the chain. In addition, patient-held device 2490 will be capable of listening for, and responding to, the alarm silence command by temporarily halting the alarm until the alarm-causing condition is addressed on patient-held device 2490.

The repeating/forwarding function can be served by a proprietary protocol or by a commercially available protocol such as ZigBee, Bluetooth, WiFi, and the like. Further, the protocol for the network of annunciator/repeater devices can be designed to be self-healing, allowing the networked annunciator/repeater devices to maintain connectivity if any annunciator/repeater device malfunctions, as is the case in a self-healing mesh network. Furthermore, the network protocol will be capable of determining which device malfunctioned and will be configured to sound an alarm via one of the other annunciator/repeater devices. The annunciator/repeater devices may also be equipped with another communication protocol such as Bluetooth, WiFi, or cellular, to forward a message to a device not inherently part of the repeater network or patient-held device 2490. One suitable example is when a patient-held device transmits a message via a first telemetry to the annunciator/repeater network, which uses a second telemetry to forward that message within the annunciator/repeater network, and one designated annunciator/repeater also forwards the message via a third telemetry (which may be the same as the second or first telemetry) to another device such as a cell phone.

In the repeater network, even though the location of the patient-held device is unknown, it is possible to determine which repeater in the chain is closest to the patient-held device by virtue of the signal strength received. The device that has the highest signal strength would initiate the forwarding of the message to the next repeater in the chain. This would mean that the repeater network devices are in regular communication with each other, which would be the case regardless to ensure a device in the chain has not failed.

Alternatively, message forwarding may be triggered if a device in the chain obtains a received signal strength measurement that exceeds a preset threshold. In this regard, if a device receives a message having at least the threshold signal strength, then the device can initiate the forwarding of the message. If two or more devices all receive a message with the same signal strength, then the forwarding scheme could switch to one of the schemes described above.

A device for a medical device network may be suitably configured in a manner that combines the functionality of a wireless repeater/annunciator and a data communication translation device (see FIGS. 18-20 and related description). Such a device may be powered by a USB connection when coupled to a computer, by a conventional household AC supply, or by an AC or DC adapter having a USB connector. This device may be configured as a full-featured component (e.g., a bedside or hospital monitor as described above), or as a reduced-featured component having a minimal or no user interface. For example, a minimal user interface may include an alarm silence/termination button and perhaps a volume control element for audio alarms. In practice, such a combined device could be programmable via a personal computer or other suitable computing device (using, for example, a USB connection).

An embodiment of a wireless medical device as described herein can be configured to support both reliable wireless links (where missing or unacknowledged packets result in the generation of alarms) and unreliable wireless links (where missing or unacknowledged packets do not result in the generation of alarms) in a dynamically switching manner and in response to various criteria. In practice, unreliable links may be associated with a "best effort" quality of service. One example of a dynamically switchable wireless link is the wireless link between an infusion pump and a bedside monitor for the pump. Although this link may be a reliable link while the patient is asleep and in close proximity to the bedside monitor, during the day the link could switch to a best effort link to accommodate periods of time when the patient might be outside of the reliable range of the bedside monitor. When the patient (and the infusion pump) returns within range of the bedside monitor, the link can switch back to a reliable link and accumulated patient data can be transferred in a batch mode.

Figure 36:
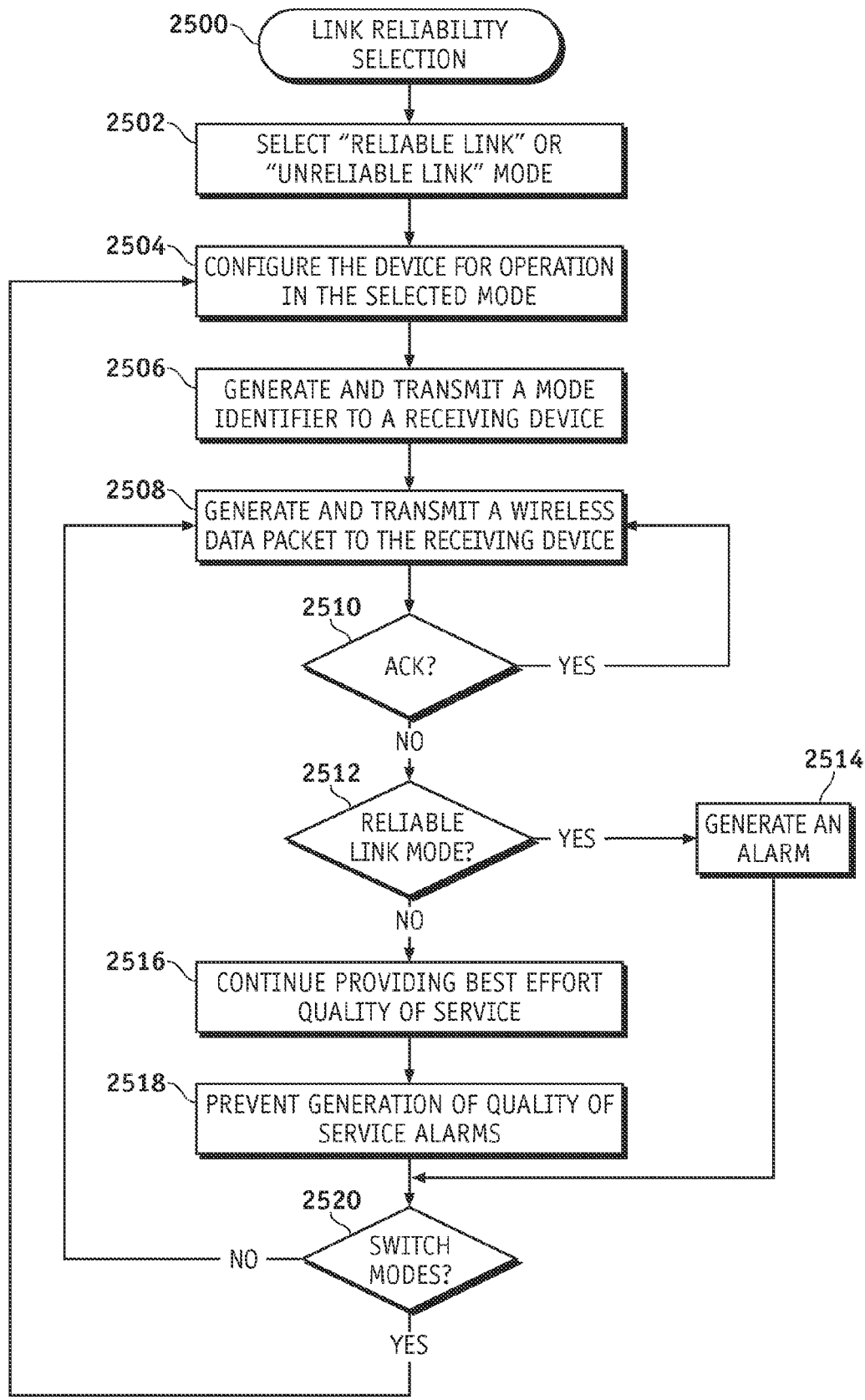
FIG. 36 is a flow chart that illustrates a link reliability selection process suitable for use in a wireless medical device network.

For example, FIG. 36 is a flow chart that illustrates a link reliability selection process 2500 suitable for use in a wireless medical device network. Process 2500 may be performed by wireless medical devices that are configured to support both reliable links and unreliable links. Process 2500 may begin by selecting the "reliable link" mode or the "unreliable link" mode (task 2502). Task 2502 may be responsive to a selection made by a user of the medical device system, the selection may be automatically initiated by the medical device in response to current operating conditions, or the selection may be made by another device in the system and communicated to the transmitting device. For example, the particular wireless data communication mode may be selected in response to: (1) a priority associated with data to be transferred between the devices; (2) a data type category associated with data to be transferred between the devices; (3) a predetermined schedule; (4) transmit power criteria; and/or (5) a quality of service measurement for a wireless data communication session between the devices. Regarding item (1), the reliable link mode can be selected for data marked with a relatively high priority, while the unreliable link mode can be selected for data marked with a relatively low priority. Regarding item (2), the reliable link mode can be selected for urgent or time-sensitive items such as alarms and event markers, while the unreliable link mode can be selected for background or device status information. Regarding item (3), the reliable link mode can be selected during normal sleeping hours, while the unreliable link mode can be selected during normal working hours. Regarding item (4), the reliable link mode can be selected for relatively high power transmissions, while the unreliable link mode can be selected for relatively low power transmissions. Regarding item (5), the reliable link mode can be selected when the wireless channel between the devices is of relatively high quality, while the unreliable link mode can be selected when the wireless channel between the devices is of relatively low quality. Of course, the dynamic selection of the wireless data communication mode need not be restricted to these examples, and an embodiment of the medical device system may utilize different criteria that governs the selection made during task 2502.

After the link reliability mode has been selected, the transmitting device is configured to support operation in the selected mode (task 2504). In this regard, the transmitting device is configured to support either of the dynamically selectable modes (the reliable link mode or the unreliable link mode in this example). Link reliability selection process 2500 may also generate and transmit a mode identifier to the receiving device (task 2506). The mode identifier designates or identifies the selected wireless data communication mode, and the mode identifier prompts the receiving device to configure itself to support the selected mode (as designated by the mode identifier). In this example where only two different link reliability modes are available, the mode identifier can simply be a one-bit flag that is transmitted in an appropriate format. The mode identifier may be transmitted as overhead in a data packet or transmitted in at least one initial bonding packet (packets that are sent at the beginning of a wireless data communication session).

Once the wireless medical devices are operating in the selected link reliability mode, a transmitting device can generate and transmit a wireless data packet to a receiving device (task 2508). If the transmitting device receives an acknowledgement (ACK) of the transmitted data packet (query task 2510), then task 2508 may be re-entered to enable the continued transmission of additional wireless data packets using the selected mode. If the transmitting device does not receive an ACK message for the transmitted data packet, then it may check to determine whether the reliable link mode is currently active (query task 2512). If the devices are currently operating in the reliable link mode, then an appropriate alarm is generated (task 2514) to notify the user that a wireless data packet may have been missed or that the wireless link has become unreliable. In practice, task 2514 may be delayed until a specified number of data packets have been transmitted without acknowledgment.

If query task 2512 determines that the unreliable link mode is currently active, then the devices will continue providing a best effort quality of service (task 2516) regardless of the wireless data packet acknowledgement status. In other words, the unreliable link mode tolerates unacknowledged packets and the devices need not take any special action in response to unacknowledged packets. Indeed, the devices might be suitably configured to prevent the generation of quality of service alarms (task 2518) while operating in the unreliable link mode. This feature ensures that alarms are not generated for low priority data items.

In this example, the devices are capable of dynamically switching between the different wireless data communication modes, and such dynamic switching may occur during a wireless data communication session between the devices. Accordingly, if one or both of the devices decide to switch modes (query task 2520), then link reliability process 2500 may be re-entered at task 2504 to reconfigure a transmitting device for operation in the newly selected mode. If the current mode is not switched, then process 2500 may be re-entered at task 2508.

Figure 37:
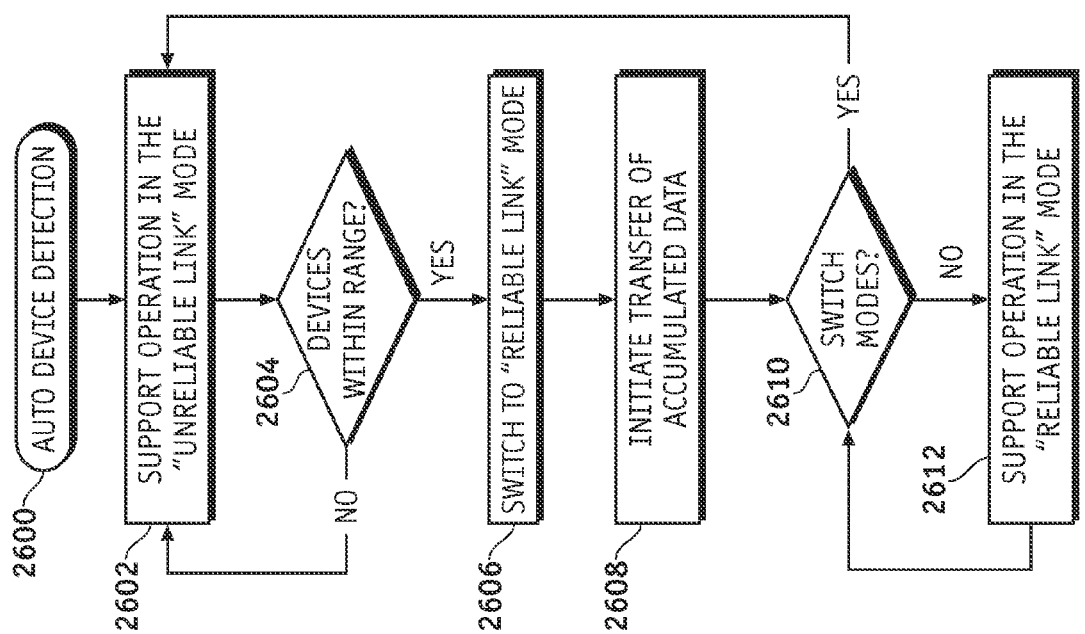
FIG. 37 is a flow chart that illustrates an auto device detection process suitable for use in a wireless medical device network.

Wireless medical devices in the system may be configured to automatically switch from the unreliable link mode to the reliable link mode when they become within a certain range of each other. For example, FIG. 37 is a flow chart that illustrates an auto device detection process 2600 suitable for use in a wireless medical device network. Process 2600 assumes that the devices are already supporting operation in the unreliable link mode (task 2602). If one (or both) of the devices automatically detects that the devices are within range for the reliable link mode (query task 2604), then the devices can switch to the reliable link mode (task 2606). Otherwise, the devices can continue operating in the unreliable link mode.

Upon switching from the unreliable link mode to the reliable link mode, auto device detection process 2600 may initiate the transfer of accumulated data (task 2608), which may have collected at one or both devices. This enables the devices to be updated with "fill-in" data that may have been missed while the devices were operating in the unreliable link mode. As described above in the context of link reliability selection process 2500, the wireless medical devices may be configured to dynamically switch between the reliable link mode and the unreliable link mode. Accordingly, if the current mode is switched (query task 2610), then process 2600 may be re-entered at task 2602 to support operation in the unreliable link mode. Otherwise, process 2600 can continue to support operation in the reliable link mode (task 2612) until the wireless data communication session ends or until the mode is switched.

Figure 38:
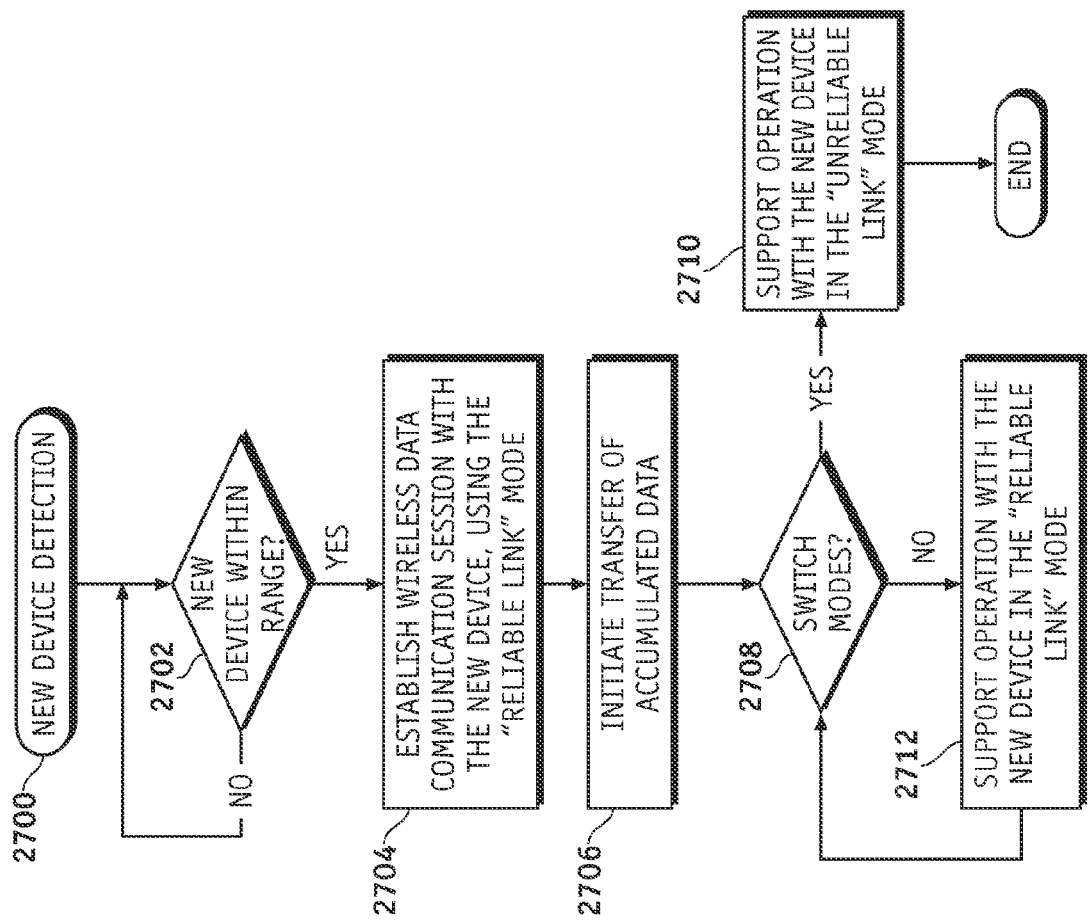
FIG. 38 is a flow chart that illustrates a new device detection process suitable for use in a wireless medical device network.

A wireless medical device in the system may also be configured to automatically detect the presence of new compatible devices when they are within a certain range of the existing device. For example, FIG. 38 is a flow chart that illustrates a new device detection process 2700 suitable for use in a wireless medical device network. Process 2700 assumes that a first device is already active in the medical device network. If the first device automatically detects that a new device is within range for the reliable link mode (query task 2702), then process 2700 establishes a wireless data communication session between the first device and the new device (task 2704); the wireless data communication session uses the reliable link mode for wireless data transfer between the two devices.

After detecting and connecting with the new device, new device detection process 2700 may initiate the transfer of accumulated data (task 2706), which may be stored at the new device. This enables the first device to be updated with "fill-in" data for the new device. As described above in the context of link reliability selection process 2500, the wireless medical devices may be configured to dynamically switch between the reliable link mode and the unreliable link mode. Accordingly, if the current mode is switched (query task 2708), then process 2700 may cause the devices to be reconfigured to support operation in the unreliable link mode (task 2710) until the wireless data communication session ends or until the mode is again switched. Otherwise, process 2700 can continue to support operation in the reliable link mode (task 2712) until the wireless data communication session ends or until the mode is switched.

A wireless medical device in the system may also be configured to select between a synchronous wireless data communication mode or an asynchronous wireless data communication mode for a given data communication session with another device. In the asynchronous mode, wireless data packets can be transmitted at arbitrary times; in the synchronous mode, wireless data packets are sent and received in accordance with a specified synchronization scheme.

Figure 39:
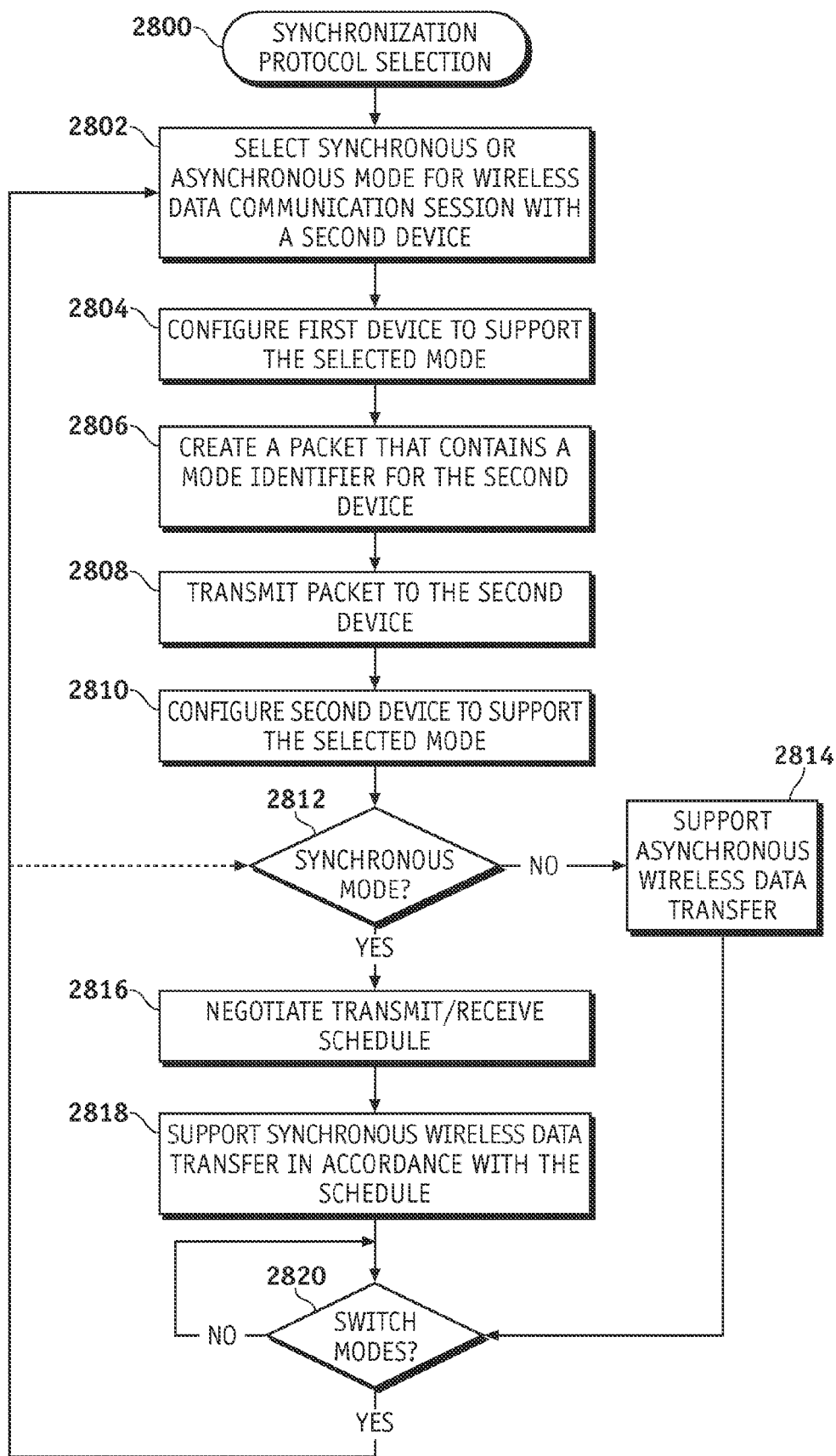
FIG. 39 is a flow chart that illustrates a synchronization protocol selection process suitable for use in a wireless medical device network.

FIG. 39 is a flow chart that illustrates a synchronization protocol selection process 2800 suitable for use in a wireless medical device network. Process 2800 may be performed by wireless medical devices that are configured to support both synchronous and asynchronous data communication protocols. Process 2800 may begin by selecting the synchronous mode or the asynchronous mode for a wireless data communication session with a device (task 2802). Task 2802 may be responsive to a selection made by a user of the medical device system, the selection may be automatically initiated by the transmitting medical device in response to current operating conditions, or the selection may be made by another device in the system and communicated to the transmitting medical device. For example, the particular wireless data communication mode may be selected in response to: (1) a priority associated with data to be transferred between the devices; (2) a data type category associated with data to be transferred between the devices; (3) a predetermined schedule; (4) transmit power criteria; and/or (5) a quality of service measurement for a wireless data communication session between the devices. These items were described above in the context of link reliability selection process 2500. The selection of the wireless data communication mode need not be restricted to these examples, and an embodiment of the medical device system may utilize different criteria that governs the selection made during task 2802.

After the synchronize mode has been selected, the transmitting device is configured to support operation in the selected mode (task 2804). In this regard, the transmitting device is configured to support either of the dynamically selectable modes (the synchronous mode or the asynchronous mode in this example). Synchronization protocol selection process 2800 may also create a packet that contains a mode identifier for processing by the receiving device (task 2806). The mode identifier designates or identifies the synchronous mode or the asynchronous mode, and the mode identifier prompts the receiving device to configure itself to support the selected mode (as designated by the mode identifier). In this example where only two different synchronize settings are available, the mode identifier can simply be a one-bit flag that is transmitted in an appropriate format. The transmitting device transmits the packet with the mode identifier to the receiving device (task 2808). In practice, the mode identifier may be transmitted as overhead in a data packet or transmitted in at least one initial bonding packet. Upon receipt of this packet, the receiving device is configured to support the selected mode (task 2810).

If the selected mode is the asynchronous mode (the "NO" branch of query task 2812), then the wireless medical devices will operate in a manner that supports asynchronous wireless data transfer (task 2814). Otherwise, if the selected mode is the synchronous mode, then the devices may negotiate or select a suitable transmit/receive schedule for data transferred between the devices (task 2816). In addition, the wireless medical devices will operate in a manner that supports synchronous wireless data transfer in accordance with the negotiated transmit/receive schedule (task 2818). This schedule may designate specific transmit and receive time slots for the two devices such that each device will know when to transmit a packet to the other device, and when to expect to receive a packet from the other device.

In this example, the devices are capable of dynamically switching between the synchronous and asynchronous modes, and such dynamic switching may occur during a wireless data communication session between the devices. Accordingly, if one or both of the devices decide to switch modes (query task 2820), then synchronization protocol selection process 2800 may be re-entered at task 2802 (or possibly task 2812) to reconfigure the devices to support the new mode. Otherwise, query task 2820 may be re-entered so that process 2800 can continue monitoring for a mode switching instruction.

A wireless medical device in the system may also be configured to select a frequency allocation scheme for a given wireless data communication session with another device. This feature allows for flexibility in the complexity of the devices in the medical device network. An embodiment may be configured to support any number of different frequency allocation schemes and to choose one of the schemes for use with any given wireless data communication link. As one non-limiting example, the device can select from the following options: a single frequency/channel mode; a five frequency/channel, low power mode; and a fifty frequency/channel, high power mode. In connection with an infusion system, the wireless link between a physiological sensor transmitter and an infusion pump may utilize the five frequency/channel mode to conserve battery power, however, during times of increased packet loss or collision, the devices may switch to the fifty frequency/channel mode to achieve increased transmit power.

Figure 40:
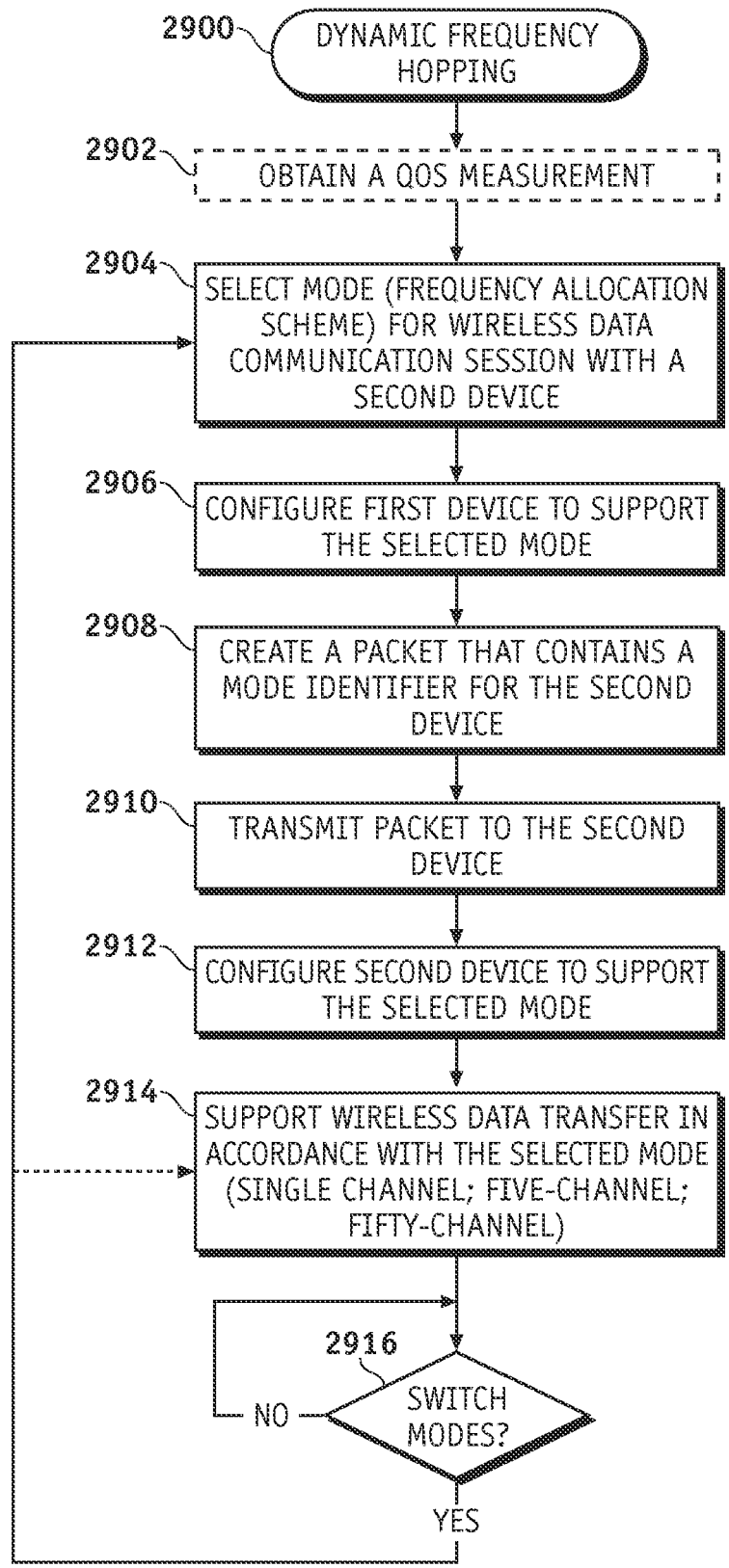
FIG. 40 is a flow chart that illustrates a dynamic frequency hopping process suitable for use in a wireless medical device network.

FIG. 40 is a flow chart that illustrates a dynamic frequency hopping process 2900 suitable for use in a wireless medical device network. Process 2900 may be performed by wireless medical devices that are configured to support a plurality of different frequency allocation (e.g., frequency hopping) schemes. In connection with process 2900, the wireless medical device may obtain a quality of service measurement for a current wireless data communication session with another device (task 2902). Task 2902 is depicted in dashed lines to indicate its optional nature; the quality of service measurement represents an optional parameter that can be utilized to govern the selection of the frequency allocation scheme.

Dynamic frequency hopping process 2900 is utilized to select (task 2904) a desired wireless data communication mode from a plurality of supported modes, where each supported mode corresponds to a different frequency allocation scheme. Task 2904 may be responsive to a selection made by a user of the medical device system, the selection may be automatically initiated by the transmitting medical device in response to current operating conditions, or the selection may be made by another device in the system and communicated to the transmitting medical device. For example, the particular frequency allocation scheme may be selected in response to: (1) a priority associated with data to be transferred between the devices; (2) a data type category associated with data to be transferred between the devices; (3) a predetermined schedule; (4) transmit power criteria; and/or (5) a quality of service measurement for a wireless data communication session between the devices. These items were described above in the context of link reliability selection process 2500. The selection of the frequency allocation scheme need not be restricted to these examples, and an embodiment of the medical device system may utilize different criteria that governs the selection made during task 2904.

After the frequency allocation scheme has been selected, the transmitting device is configured (setup) to support operation in the selected mode (task 2906). In this regard, the transmitting device is able to support any of a plurality of frequency allocation schemes in a dynamically selectable manner—the single frequency/channel mode, the five frequency/channel mode, or the fifty frequency/channel mode in this example. Dynamic frequency hopping process 2900 may also create a packet that contains a mode identifier for processing by the receiving device (task 2908). The mode identifier designates or identifies the selected operating mode, and the mode identifier prompts the receiving device to configure itself to support the selected mode (as designated by the mode identifier). In this example where three different frequency allocation schemes are available, the mode identifier can be a two-bit flag that is transmitted in an appropriate format. The transmitting device transmits the packet containing the mode identifier to the receiving device (task 2910). In practice, the mode identifier may be transmitted as overhead in a data packet or transmitted in at least one initial bonding packet. Upon receipt of this packet, the receiving device is configured (setup) to support the selected mode (task 2912).

Eventually, both devices are setup to support wireless data transfer in accordance with the selected wireless data communication mode and in accordance with the designated frequency allocation scheme (task 2914). In this example, the devices are capable of dynamically switching between the different modes, and such dynamic switching may occur during a wireless data communication session between the devices. Accordingly, if one or both of the devices decide to switch modes (query task 2916), then dynamic frequency hopping process 2900 may be re-entered at task 2904 (or possibly task 2914) to reconfigure the devices to support the new mode. Otherwise, query task 2916 may be re-entered so that process 2900 can continue monitoring for a mode switching instruction.

In practice, synchronous wireless links operate with a designated transmission periodicity (e.g., sixty seconds per packet). The transmitting device can retransmit (retry) a packet if that packet was missed or unacknowledged. Moreover, the two devices may follow a particular retry synchronization scheme where retry packets are sent with a designated retry periodicity (e.g., twenty seconds per retry packet). In this regard, a wireless medical device as described herein may also be configured to adjust its packet retransmission (retry) settings for synchronous links. For example, the device can select a particular retry periodicity based upon current operating conditions and/or characteristics of the data to be transferred. The selection may be governed by various criteria such as data transmission reliability, power saving, available bandwidth, or the like. Moreover, both devices can adapt their frequency hopping scheme in a negotiated manner (for example, as described above in the context of dynamic frequency hopping process 2900) for retry packets and, once the nominal quality of service is resumed for the wireless link, revert back to the baseline frequency hopping scheme.

Figure 41:
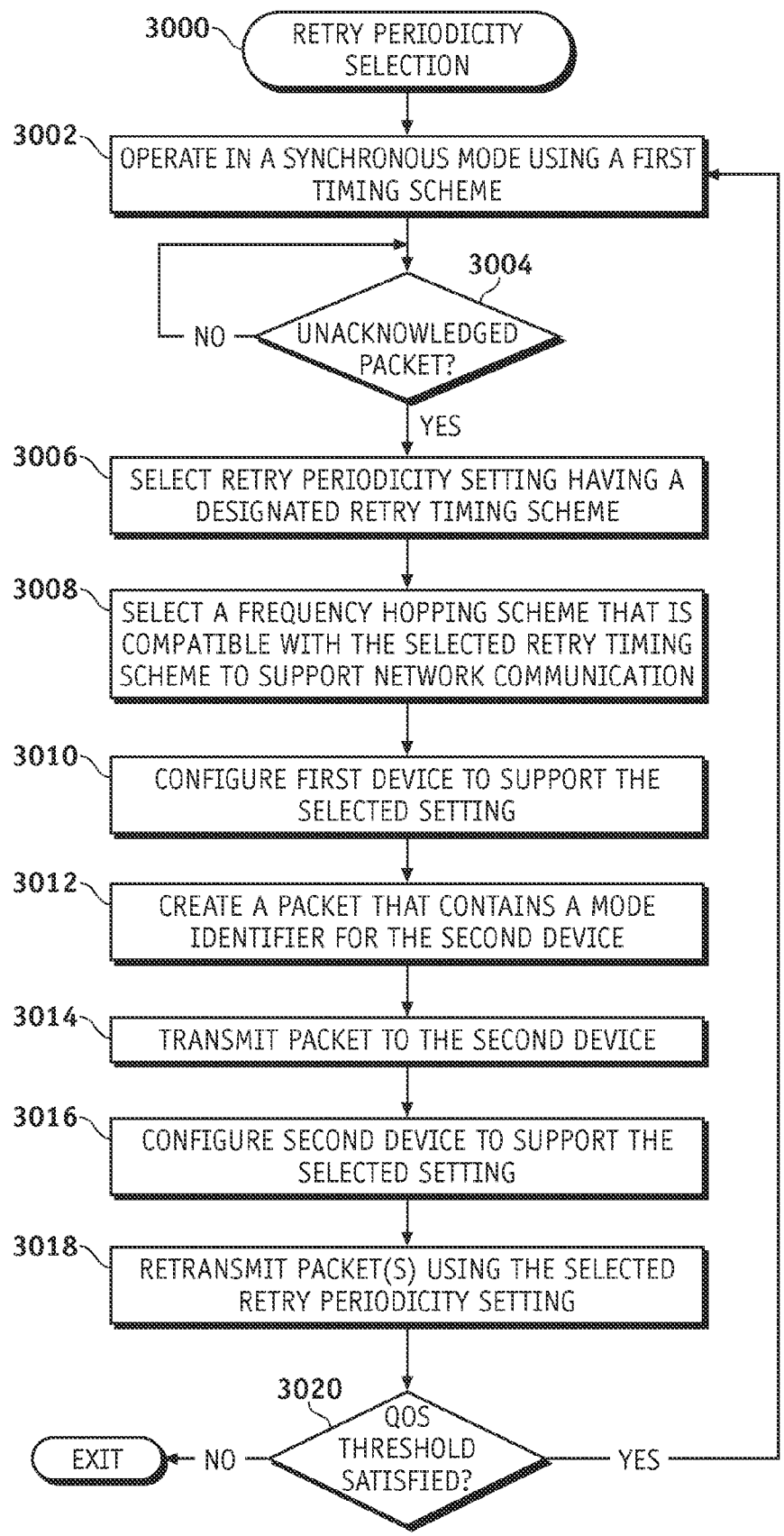
FIG. 41 is a flow chart that illustrates a retry periodicity selection process suitable for use in a wireless medical device network.

FIG. 41 is a flow chart that illustrates a retry periodicity selection process 3000 suitable for use in a wireless medical device network. Process 3000 may be performed by wireless medical devices that are configured to support a plurality of different retry periodicity settings. Process 3000 begins with the devices operating in a synchronous wireless data communication mode (task 3002) during which wireless data packets are exchanged in accordance with a first timing scheme. For this example, the first timing scheme represents the normal packet transmission periodicity associated with normal operating conditions and at least a nominal quality of service for the wireless link utilized by the devices. Thus, the first timing scheme corresponds to a first transmit/receive period for the devices. This normal operating mode is maintained until the occurrence of an unacknowledged data packet (query task 3004). In this regard, the transmitting device may receive a NAK message that indicates an unacknowledged data packet, the transmitting device may receive a retry request from the receiving device, or the transmitting device may assume that a transmitted data packet was not received if the transmitting device does not receive some type of response message within a certain time period.

If a data packet remains unacknowledged (query task 3004), then retry periodicity selection process 3000 selects (task 3006) a desired retry periodicity setting from a plurality of supported settings, where each supported setting corresponds to a respective retry timing scheme that is different than the first (normal) transmission timing scheme. In practical embodiments, each retry periodicity setting corresponds to a different transmit/receive period that is shorter than the first transmit/receive period utilized for packet transmissions under normal conditions. Task 3006 may be responsive to a selection made by a user of the medical device system, the selection may be automatically initiated by the transmitting medical device in response to current operating conditions, or the selection may be made by another device in the system and communicated to the transmitting medical device. For example, the particular retry periodicity setting may be selected in response to: (1) a priority associated with data to be transferred between the devices; (2) a data type category associated with data to be transferred between the devices; (3) a predetermined schedule; (4) transmit power criteria; and/or (5) a quality of service measurement for a wireless data communication session between the devices. These items were described above in the context of link reliability selection process 2500. Alternatively, the retry periodicity setting may be selected in response to the number of retry attempts that have been performed for the data packet. For example, the length of the retry period may decrease in proportion to the number of failed packet transmission attempts such that the frequency of retry packet transmissions increases until one has been acknowledged or until the transmitter decides to no longer make any retry attempts. The selection of the retry periodicity setting need not be restricted to these examples, and an embodiment of the medical device system may utilize different criteria that governs the selection made during task 3006.

Assuming that the devices are communicating using a synchronous wireless data communication protocol, it may be necessary to select an appropriate frequency hopping scheme (from a plurality of supported frequency hopping schemes) that is compatible with the selected retry timing scheme (task 3008). For example, dynamic frequency hopping process 2900, or a suitable variant thereof, can be utilized in connection with task 3008. The selection of an appropriate frequency allocation scheme enables the devices to support network communication using the designated retry periodicity setting.

After the retry periodicity setting and the frequency hopping scheme have been selected, the transmitting device is configured (setup) to support operation in the selected mode (task 3010). In this regard, the transmitting device is able to support any of a plurality of retry timing schemes in a dynamically selectable manner. Retry periodicity selection process 3000 may also create a packet that contains a mode identifier for processing by the receiving device (task 3012). The mode identifier designates or identifies the selected retry periodicity setting, and the mode identifier prompts the receiving device to configure itself to support the selected mode (as designated by the mode identifier). The transmitting device transmits the packet containing the mode identifier to the receiving device (task 3014). In practice, the mode identifier may be transmitted as overhead in a data packet or transmitted in a packet that conveys dynamic link parameters without any payload data. Upon receipt of this packet, the receiving device is configured (setup) to support the selected mode (task 3016).

Eventually, both devices are setup to support the designated retry timing scheme. Accordingly, the transmitting device can retransmit at least one wireless data packet using the designated retry periodicity setting (task 3018). In this example, if one or both devices detect an operating condition that satisfies a quality of service threshold (query task 3020), then retry periodicity selection process 3000 may be re-entered at task 3002 such that the normal timing scheme and the baseline retry timing scheme are again utilized for subsequently transmitted data packets. In other words, the system switches back to the first timing scheme and switches back to its nominal retry periodicity setting. If the threshold quality of service is not satisfied (query task 3020), then process 3000 may exit or otherwise proceed in an appropriate manner. For example, query task 3004 may be re-entered to enable dynamic adjustment of the retry timing scheme. Alternatively, the current retry timing scheme may be maintained for a period of time or until the quality of service improves or degrades by a specified amount.

A wireless medical device as described herein may also be configured to provide varying time periods between transmissions based upon various criteria such as, without limitation: the particular physiological data (e.g., rising or falling trends), failure to respond to an alert, failure to notice a change in physiological parameters, or the like. The transmitted packet could provide a field for notifying the receiving device of the desired time period after which the next data packet will be transmitted. This could be implemented using a time differential or a specified time, assuming that both devices are synchronized with a common clock. Alternatively, time synchronization with a common clock may not be necessary if a time stamp is sent with the data. In that case, the resolution of the time (e.g., microseconds) needs to be the same in order to know when to expect the next data packet.

Figure 42:
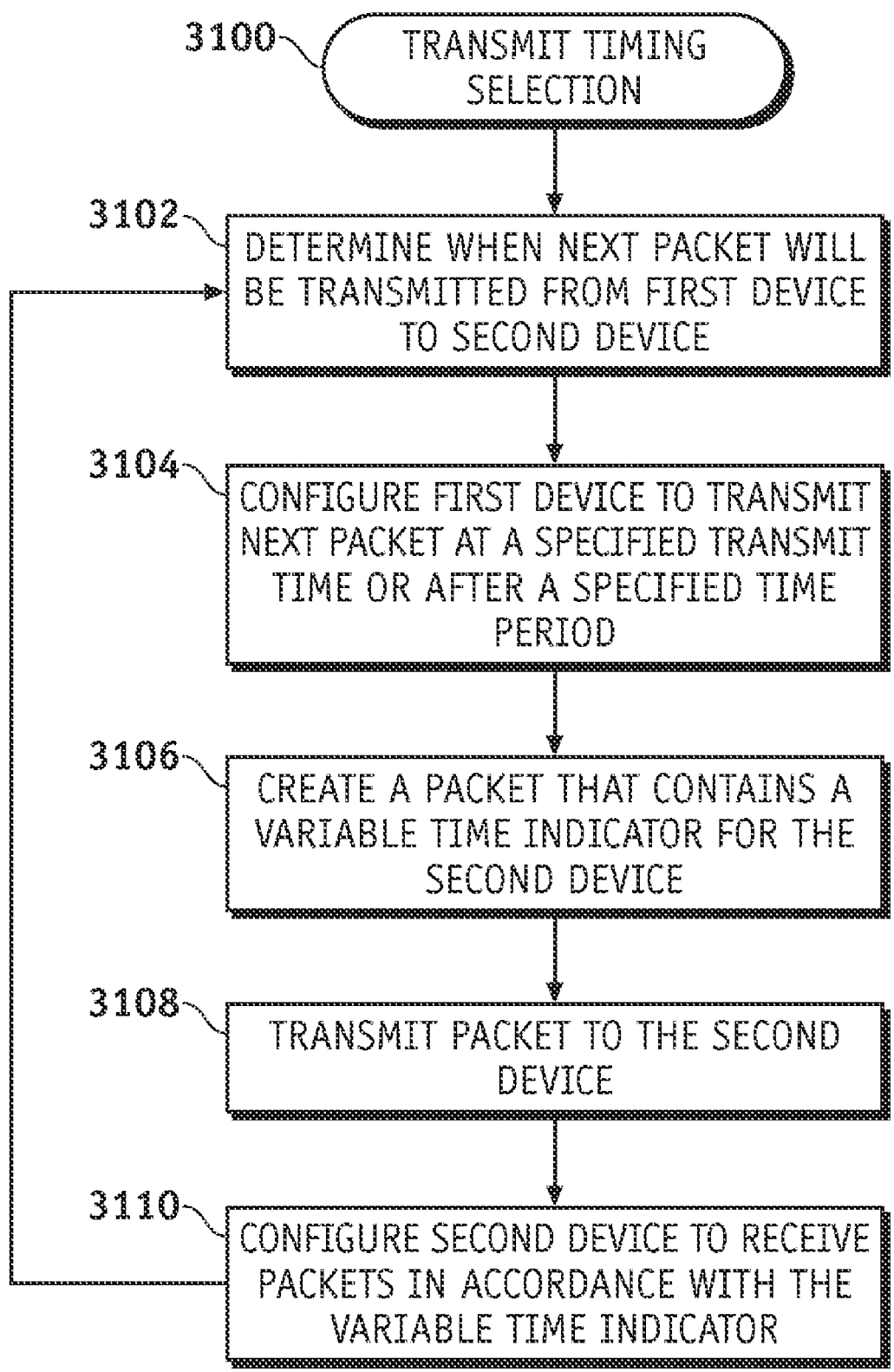
FIG. 42 is a flow chart that illustrates a transmit timing selection process suitable for use in a wireless medical device network.

For example, FIG. 42 is a flow chart that illustrates a transmit timing selection process 3100 suitable for use in a wireless medical device network. Process 3100 assumes that the wireless medical devices exchange data in a synchronous manner. Process 3100 may be performed by wireless medical devices that are configured to support a variable transmit/receive timing scheme. In connection with process 3100, the transmitting device dynamically determines when the next wireless data packet will be transmitted to the receiving device (task 3102). The transmitting device may then generate or select a variable time indicator that indicates when the next data packet will be transmitted over the wireless data communication channel. In one embodiment, the variable time indicator indicates a specific transmit time for the next packet. In another embodiment, the variable time indicator indicates a specific time period, where the next data packet will be transmitted after the specified time period.

The selection of the variable time indicator may be responsive to a selection made by a user of the medical device system, the selection may be automatically initiated by the transmitting medical device in response to current operating conditions, or the selection may be made by another device in the system and communicated to the transmitting medical device. For example, the particular variable time indicator may be selected in response to: (1) a priority associated with data to be transferred between the devices; (2) a data type category associated with data to be transferred between the devices; (3) a predetermined schedule; (4) transmit power criteria; and/or (5) a quality of service measurement for a wireless data communication session between the devices. These items were described above in the context of link reliability selection process 2500. Alternatively, the variable time indicator may be selected in response to trending characteristics in the data transferred between the devices. For example, if the trending characteristics represent a relatively high rate of change in the data transferred between the devices, the variable time indicator may indicate a relatively short time period corresponding to when the next data packet will be transmitted. On the other hand, if the trending characteristics represent a relatively low rate of change in the data transferred between the devices, the variable time indicator may indicate a relatively long time period corresponding to when the next data packet will be transmitted. Of course, the selection of the variable time indicator need not be restricted to these examples, and an embodiment of the medical device system may utilize different criteria that governs the selection of the variable time indicator. One practical benefit of this scheme is to lower the power consumption by reducing RF "on" time. Other practical benefits may also be derived from this scheme.

After the variable time indicator has been selected, the transmitting device configures itself to transmit the next data packet at the specified transmit time or after the specified time period, as designated by the variable time indicator (task 3104). Transmit timing selection process 3100 may also create a packet that contains the variable time indicator for processing by the receiving device (task 3106), and transmit that packet to the receiving device (task 3108). In practice, the variable time indicator may be transmitted as overhead in a data packet, transmitted in at least one initial bonding packet, or transmitted in a packet that conveys dynamic link parameters without any payload data. The variable time indicator prompts the receiving device to configure itself to receive the next data packet as designated by the variable time indicator. Accordingly, upon receipt of this packet, the receiving device is configured (setup) in response to the variable time indicator (task 3110).

The transmitting device can adjust the transmit time for subsequent packets in a dynamic manner. Accordingly, FIG. 42 depicts task 3110 leading back to task 3102. Notably, the timing need not be adjusted for each transmitted packet, and transmit timing selection process 3100 may preserve a selected transmit timing scheme for any number of packet transmissions before altering the current timing scheme.

In an alternate embodiment, the receiving (second) device receives data packets from the first device, performs data analysis, and, in response thereto, determines a time period or a specific time for the next data packet transmission. Thereafter, the receiving device will generate and send an ACK message back to the transmitting (first) device, with the selected time period or specific time corresponding to the next transmission. In practice, the selected time period or specific time for the next transmission may be conveyed in the ACK message itself or in a separate data packet.

Referring again to FIG. 23, one or more of the dynamic link parameters described above can be transmitted via a wireless data communication signal having data fields arranged in a suitably formatted data packet 1700. In this context, the dynamic link parameters are any of the various mode identifiers and variables that result in adjustments in the wireless data communication protocols/links used between the wireless medical devices.

Data packet 1700 may, for example, be an initial bonding packet that is used to initiate a wireless data communication session between two devices. As mentioned previously, data packet 1700 may include data or data fields corresponding to one or more of the following dynamic link parameters: a link reliability setting 1702; a synchronize setting 1704; a frequency allocation setting 1706; a retry periodicity setting 1708; a master/slave setting 1710; and/or a transmit timing indicator 1712. Depending upon the particular system application, one or more of these link parameters can be dynamically updated during a wireless data communication session.

The data contained in data packet 1700 represents a selected one of a plurality of supported wireless data communication modes, where each mode corresponds to a different set of wireless or RF link characteristics for the wireless data communication channel between the devices.

For the example described here, the data fields shown in FIG. 23 correspond to various parameters and indicators described above. Thus, link reliability setting 1702 designates either the reliable link mode or the unreliable link mode, as described in more detail above in the context of link reliability selection process 2500 (see FIG. 36). In addition, synchronize setting 1704 designates either the synchronous wireless data communication mode or the asynchronous wireless data communication mode, as described in more detail above in the context of synchronization protocol selection process 2800 (see FIG. 39). For the example described here, frequency allocation setting 1706 designates one of the plurality of supported frequency hopping schemes, as described in more detail above in the context of dynamic frequency hopping process 2900 (see FIG. 40). Moreover, retry periodicity setting 1708 designates one of the plurality of supported retry timing schemes, as described in more detail above in the context of retry periodicity selection process 3000 (see FIG. 41). For the example described here, master/slave setting 1710 designates a master device status or a slave device status for a device that originates data packet 1700, as described in more detail above in the context of master-slave communication process 2100 (see FIG. 29 and FIG. 30). In addition, transmit timing indicator 1712 designates when the next packet will be transmitted, as described in more detail above in the context of transmit timing selection process 3100 (see FIG. 42).

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

What is claimed is:

1. A communication method for a medical device network having a first device and a second device configured to wirelessly communicate data between each other using a synchronized data communication protocol, the method comprising:
the first device dynamically determining when a next data packet will be transmitted to the second device over a wireless data communication channel, wherein the next data packet conveys physiological data indicative of a measured physiological characteristic of a patient; and
the first device wirelessly transmitting a variable time indicator to the second device, wherein the variable time indicator indicates when the next data packet will be transmitted over the wireless data communication channel, and wherein the variable time indicator prompts the second device to configure itself to wirelessly receive the next data packet as designated by the variable time indicator; wherein:
if a trending characteristic of the physiological data indicates a relatively high rate of change of the measured physiological characteristic, the first device selects a first time indicator that indicates a relatively short time period corresponding to when the next data packet will be transmitted; and
if the trending characteristic of the physiological data indicates a relatively low rate of change of the measured physiological characteristic, the first device selects a second time indicator that indicates a relatively long time period corresponding to when the next data packet will be transmitted.

2. A method according to claim 1, further comprising the first device configuring itself to wirelessly transmit the next data packet as designated by the variable time indicator.

3. A method according to claim 1, further comprising the first device selecting the variable time indicator in response to a priority associated with data to be transferred between the first device and the second device.

4. A method according to claim 1, further comprising the first device selecting the variable time indicator in response to a data type category associated with data to be transferred between the first device and the second device.

5. A method according to claim 1, further comprising the first device selecting the variable time indicator in response to a transmit power criteria.

6. A method according to claim 1, further comprising the first device selecting the variable time indicator in response to a quality of service measurement.

7. The method of claim 1, wherein the measured physiological characteristic of the patient is a blood glucose level of the patient.

8. The method of claim 7, further comprising the first device receiving the blood glucose level from a continuous glucose sensor transmitter in real time.

9. The method of claim 7, wherein:
the first device is a continuous glucose sensor transmitter; and
the method further comprises the continuous glucose sensor transmitter measuring the blood glucose level in real time.

* * * * *